(12) United States Patent
Baldwin et al.

(10) Patent No.: US 10,792,067 B2
(45) Date of Patent: Oct. 6, 2020

(54) METHODS AND APPARATUSES FOR FLURO-LESS OR NEAR FLUORO-LESS PERCUTANEOUS SURGERY ACCESS

(71) Applicant: FACULTY PHYSICIANS AND SURGEONS OF LOMA LINDA UNIVERSITY SCHOOL OF MEDICINE, Loma Linda, CA (US)

(72) Inventors: Dalton Duane Baldwin, Loma Linda, CA (US); Avijit Mukherjee, Irvine, CA (US); Steven Mark Redenbaugh, Harrison, TX (US); Ronald Steven Pirucki, Coto de Caza, CA (US); James Watson, Loma Linda, CA (US)

(73) Assignee: FACULTY PHYSICIANS AND SURGEONS OF LOMA LINDA UNIVERSITY OF MEDICINE, Loma Linda, CA (US)

(*) Notice: Subject to any disclaimer, the term of this patent is extended or adjusted under 35 U.S.C. 154(b) by 230 days.

(21) Appl. No.: 15/963,542

(22) Filed: Apr. 26, 2018

(65) Prior Publication Data
US 2019/0125398 A1 May 2, 2019

Related U.S. Application Data

(63) Continuation-in-part of application No. 15/890,090, filed on Feb. 6, 2018, now abandoned, which is a
(Continued)

(51) Int. Cl.
A61B 17/34 (2006.01)
A61B 1/00 (2006.01)
(Continued)

(52) U.S. Cl.
CPC ...... *A61B 17/3415* (2013.01); *A61B 1/00147* (2013.01); *A61B 1/00154* (2013.01);
(Continued)

(58) Field of Classification Search
CPC .............. A61B 1/00059; A61B 3/0066; A61B 5/150793; A61B 2562/226;
(Continued)

(56) References Cited

U.S. PATENT DOCUMENTS 3,801,205 A * 4/1974 Eggenschwyler ... G01C 15/002
356/138
4,319,839 A * 3/1982 Durran ................. G01B 11/272
356/153
(Continued)

FOREIGN PATENT DOCUMENTS

| JP | 2002510997 | 4/2002 |
| WO | 9315683 A1 | 8/1993 |
| WO | 2014197502 A1 | 12/2014 |

OTHER PUBLICATIONS

International Search Report for PCT/US18/29550, dated Jul. 30, 2018.
(Continued)

*Primary Examiner* — Amy R Weisberg
(74) *Attorney, Agent, or Firm* — Womble Bond Dickinson (US) LLP

(57) ABSTRACT

A needle access assembly and method for obtaining percutaneous needle access with little or no fluoroscopy is disclosed. The method includes selecting a target for percutaneous access, directing a laser guide at a desired needle-insertion angle and in line with the selected target, aligning the needle access assembly with the laser, and inserting the needle into the target.

18 Claims, 34 Drawing Sheets

Related U.S. Application Data continuation of application No. 14/802,753, filed on Jul. 17, 2015, now Pat. No. 9,918,739, which is a continuation of application No. 14/295,148, filed on Jun. 3, 2014, now Pat. No. 9,095,361, application No. 15/963,542, which is a continuation-in-part of application No. 15/145,631, filed on May 3, 2016, now Pat. No. 10,085,767, which is a continuation of application No. 14/678,696, filed on Apr. 3, 2015, now Pat. No. 9,351,758, which is a continuation of application No. 14/295,224, filed on Jun. 3, 2014, now Pat. No. 8,998,943, application No. 15/963,542, which is a continuation-in-part of application No. 15/271,414, filed on Sep. 21, 2016, now Pat. No. 10,405,943.

(60) Provisional application No. 62/490,390, filed on Apr. 26, 2017, provisional application No. 61/902,090, filed on Nov. 8, 2013, provisional application No. 61/830,585, filed on Jun. 3, 2013, provisional application No. 62/222,037, filed on Sep. 22, 2015.

(51) Int. Cl.

| | | |
|---|---|---|
| *A61B 6/00* | (2006.01) | |
| *A61M 25/00* | (2006.01) | |
| *A61M 25/10* | (2013.01) | |
| *A61B 34/20* | (2016.01) | |
| *A61B 5/06* | (2006.01) | |
| *A61B 8/08* | (2006.01) | |
| *A61B 1/06* | (2006.01) | |
| *A61B 17/00* | (2006.01) | |
| *A61M 25/01* | (2006.01) | |
| *A61B 1/01* | (2006.01) | |
| *A61M 25/06* | (2006.01) | |
| *A61B 90/13* | (2016.01) | |
| *A61B 90/00* | (2016.01) | |
| *A61B 1/307* | (2006.01) | |
| *A61B 1/018* | (2006.01) | |
| *A61B 6/12* | (2006.01) | |
| *A61M 29/02* | (2006.01) | |
| *A61B 6/03* | (2006.01) | |

(52) U.S. Cl.
CPC ............... *A61B 1/01* (2013.01); *A61B 1/063* (2013.01); *A61B 1/0676* (2013.01); *A61B 5/061* (2013.01); *A61B 5/065* (2013.01); *A61B 6/485* (2013.01); *A61B 8/0841* (2013.01); *A61B 17/00234* (2013.01); *A61B 17/3403* (2013.01); *A61B 17/3423* (2013.01); *A61B 34/20* (2016.02); *A61M 25/0074* (2013.01); *A61M 25/0097* (2013.01); *A61M 25/0105* (2013.01); *A61M 25/065* (2013.01); *A61M 25/10* (2013.01); *A61B 1/018* (2013.01); *A61B 1/307* (2013.01); *A61B 6/03* (2013.01); *A61B 6/12* (2013.01); *A61B 6/487* (2013.01); *A61B 8/085* (2013.01); *A61B 8/481* (2013.01); *A61B 90/13* (2016.02); *A61B 2017/0034* (2013.01); *A61B 2017/0046* (2013.01); *A61B 2017/0092* (2013.01); *A61B 2017/00707* (2013.01); *A61B 2017/00853* (2013.01); *A61B 2017/00907* (2013.01); *A61B 2017/3413* (2013.01); *A61B 2034/2055* (2016.02); *A61B 2090/062* (2016.02); *A61B 2090/0807* (2016.02); *A61B 2090/3762* (2016.02); *A61B 2090/3925* (2016.02); *A61B 2090/3966* (2016.02); *A61M 29/02* (2013.01); *A61M 2025/0681* (2013.01); *A61M 2210/1082* (2013.01)

(58) Field of Classification Search
CPC .............. A61B 17/3403; A61B 19/201; A61B 2019/202; A61B 19/5244; A61B 19/5202; A61B 6/485; A61B 2019/5255; A61B 2017/0092; A61B 2017/0046; A61B 2090/3925; A61B 8/085; A61B 6/03; A61B 2210/1082; A61B 2090/062; A61B 6/487; A61B 90/13; A61B 2090/0807; A61B 2090/3762; A61B 2090/3966; A61B 1/307; A61B 2034/2055; A61B 2017/00907; A61B 2017/3413; A61B 2017/0034; A61B 1/018; A61B 2017/00707; A61B 6/12; A61B 2017/00853; A61B 90/40; A61M 2205/60; A61M 2205/6063; A61M 25/0097; A61M 25/10; A61M 29/02; A61M 2025/0681; A61M 2210/1082
USPC .................. 601/1; 606/1, 96, 108, 129–130, 606/167–185; 604/103.06, 116–117, 604/533–534; 600/160, 566–567, 424; 128/898; 359/385–390, 798–800; 116/202, DIG. 5

See application file for complete search history.

(56) References Cited

U.S. PATENT DOCUMENTS

| | | | |
|---|---|---|---|
| 4,651,732 A * | 3/1987 | Frederick | A61B 90/13 606/130 |
| 4,674,870 A * | 6/1987 | Cain | G01C 15/004 356/141.3 |
| 4,803,976 A | 2/1989 | Frigg | |
| 5,409,000 A | 4/1995 | Imran | |
| 5,810,841 A * | 9/1998 | McNeirney | A61B 90/13 606/130 |
| 6,021,342 A | 2/2000 | Brabrand | |
| 6,041,249 A * | 3/2000 | Regn | A61B 6/08 378/20 |
| 6,096,049 A * | 8/2000 | McNeirney | A61B 90/13 606/130 |
| 6,443,960 B1 * | 9/2002 | Brabrand | A61B 17/3403 606/130 |
| 6,605,095 B2 * | 8/2003 | Grossman | A61B 90/13 356/399 |
| 6,607,477 B1 | 8/2003 | Longton | |
| 6,689,142 B1 * | 2/2004 | Tremaglio, Jr. | A61B 17/3403 604/114 |
| 6,810,595 B2 * | 11/2004 | Chan | A61B 17/3403 33/283 |
| 7,204,826 B2 | 4/2007 | Tremaglio | |
| 7,621,868 B2 * | 11/2009 | Breidenthal | A61B 1/00188 600/166 |
| 7,766,878 B2 | 8/2010 | Tremaglio, Jr. | |
| 7,876,942 B2 | 1/2011 | Gilboa | |
| 8,162,852 B2 * | 4/2012 | Norris | A61B 8/0841 600/567 |
| 8,454,586 B2 * | 6/2013 | Anastasie | A61B 18/24 606/15 |
| 8,715,233 B2 * | 5/2014 | Brewer | A61M 25/0612 600/424 |
| 8,998,943 B2 | 4/2015 | Baldwin | |
| 9,095,361 B2 | 8/2015 | Baldwin | |
| 9,351,758 B2 | 5/2016 | Baldwin | |
| 9,918,739 B2 | 3/2018 | Baldwin | |
| 10,010,374 B2 | 7/2018 | Besser | |
| 10,085,767 B2 | 10/2018 | Baldwin | |
| 2003/0120154 A1 * | 6/2003 | Sauer | A61B 8/0833 600/459 |
| 2004/0103903 A1 | 6/2004 | Falahee | |
| 2004/0106934 A1 | 6/2004 | Grossman | |
| 2004/0122311 A1 | 6/2004 | Cosman | |

(56) References Cited

U.S. PATENT DOCUMENTS

| | | | |
|---|---|---|---|
| 2005/0256451 A1* | 11/2005 | Adams | A61M 39/0208 |
| | | | 604/93.01 |
| 2007/0100234 A1* | 5/2007 | Arenson | A61B 6/463 |
| | | | 600/429 |
| 2007/0100299 A1 | 5/2007 | Magnusson | |
| 2007/0106231 A1 | 5/2007 | Snow | |
| 2008/0146915 A1* | 6/2008 | McMorrow | A61B 5/150748 |
| | | | 600/424 |
| 2008/0146939 A1* | 6/2008 | McMorrow | G01S 7/52036 |
| | | | 600/462 |
| 2008/0200876 A1 | 8/2008 | Kukuk | |
| 2010/0099980 A1 | 4/2010 | Godara | |
| 2011/0172520 A1 | 7/2011 | Lentz | |
| 2012/0022504 A1* | 1/2012 | Epshtein | A61B 18/24 |
| | | | 604/542 |
| 2012/0022508 A1* | 1/2012 | Gross | A61B 90/13 |
| | | | 606/1 |
| 2012/0123204 A1 | 5/2012 | Wynberg | |
| 2012/0143224 A1 | 6/2012 | Chan | |
| 2012/0316500 A1 | 12/2012 | Bierman | |
| 2013/0018254 A1* | 1/2013 | Drucker | A61B 5/0077 |
| | | | 600/424 |
| 2013/0103036 A1* | 4/2013 | McGhie | A61B 17/1757 |
| | | | 606/93 |
| 2013/0267834 A1* | 10/2013 | McGee | A61M 5/46 |
| | | | 600/424 |
| 2014/0005604 A1 | 1/2014 | Murphy | |
| 2014/0107473 A1 | 4/2014 | Dumoulin | |
| 2014/0236019 A1 | 8/2014 | Rahum | |
| 2014/0301699 A1 | 10/2014 | Goldfarb | |
| 2014/0357986 A1 | 12/2014 | Baldwin | |
| 2014/0357987 A1 | 12/2014 | Baldwin | |
| 2015/0272701 A1 | 10/2015 | Baldwin | |
| 2017/0095314 A1 | 4/2017 | Baldwin | |
| 2017/0303940 A1 | 10/2017 | Sperry | |
| 2018/0368862 A1* | 12/2018 | Jain | A61B 17/3403 |

OTHER PUBLICATIONS

Office Action dated Sep. 6, 2018 for U.S. Appl. No. 15/271,414.
Sodickson, A., Baeyens, P. F., Andriole, K. P. et al., Recurrent CT, cumulative radiation exposure, and associated radiation-induced cancer risks from CT of adults. Radiology, 251: 175-184, Apr. 2009.
Supplementary European Search Report for EP14807718, dated Dec. 5, 2016.
International Search Report for PCT/US16/52755, dated Dec. 30, 2016.
European Search Report for European Application No. EP18161332, completed on Sep. 10, 2018.
Notice of Reasons for Rejection for JP2016518415, dated Apr. 9, 2018.
Decision Of Rejection for JP2016518415, dated Oct. 30, 2018.
International Search Report for PCT/US14/40744, dated Oct. 12, 2014.
International Preliminary Report on Patentability for PCT/US14/40744, dated Oct. 12, 2014.
Bilen, et al: "Laser-Assisted Fluoroscopic Puncture: A New Technique for Accessing the Kidney", Journal of Endourology, vol. 17, No. 7, Sep. 2003.
Blair, et al.: "Reduced Fluoroscopy Protocol for Percutaneous Nephrostolithotomy: Feasibility, Outcomes and Effects on Fluoroscopy Time", The Journal of Urology, vol. 190, Dec. 2013, pp. 2112-2116.
Brisbane, et al.: "Fluoro-less Ureteral Stent Placement Following Uncomplicated Ureteroscopic Stone Removal: a Feasibility Study", Urology 80 (4), 2012, pp. 766-770.
Greene, et al.: "Comparison of a Reduced Radiation Fluoroscopy Protocol to Conventional Fluoroscopy during Uncomplicated Ureteroscopy", Urology 79 (2), 2011, pp. 287-290.
Hsi, et al.: "Fluoroless Ureteroscopy: Zero-Dose Fluoroscopy During Ureteroscopic Treatment of Urinary-Tract Calculi", Journal of Endourology, vol. 27, No. 4, Apr. 2013, pp. 432-437.
Ko, et al.: "C-Arm Laser Positioning Device to Facilitate Percutaneous Renal Access", Surgeon's Workshop, Urology 70 (2), 2007.
Kokorowski, et al.: "Prospective Systematic Intervention to Reduce Patient Exposure to Radiation During Pediatric Ureteroscopy", The Journal of Urology, vol. 190, 1474-1478, Oct. 2013.
Kroes, et al.: "Assessment of Needle Guidance Devices for Their Potential to Reduce Fluoroscopy Time and Operator Hand Dose during C-Arm Cone-Beam Computed Tomography-guided Needle Interventions", J Vasc Interv Radiol, Jun. 2013; 24:901-906.
Krupp, et al.: "Fluoroscopic Organ and Tissue-Specific Radiation Exposure by Sex and Body Mass Index During Uretereoscopy", Journal of Endourology, vol. 24, No. 7, Jul. 2010, pp. 1067-1073.
Nguyen, et al.: "In Automated Fluoroscopy Settings, Does Shielding Affect Radiation Exposure to Surrounding Unshielded Tissues? ", Journal of Endourology, vol. 26, No. 11, Nov. 2012.
Shuler et al.: "Laser Targeting With C-Arm Fluoroscopy: Effect on Image Acquisition and Radiation Exposure", J Orthop Trauma, vol. 27, No. 5, May 2013. pp. e97-e102.
Smith, et al.: "Radiation Exposure During Continuous and Pulsed Fluoroscopy", Journal of Endourology, vol. 27, No. 3, Mar. 2013, pp. 384-388.
Office Action dated Dec. 31, 2015 for U.S. Appl. No. 14/802,753.
Hawkins et al. "Combined Retrograde/Antegrade Nephrostomy Technique," 1987, Journal of Endourology, vol. 1, No. 4, pp. 235-241.
Office Action dated Sep. 20, 2016 for U.S. Appl. No. 14/802,753.
Notice of Allowance dated Nov. 7, 2017 for U.S. Appl. No. 14/802,753; (pp. 1-5).
Preinterview First Office Action dated Aug. 29, 2014 for U.S. Appl. No. 14/295,148.
International Search Report and Written Opinion, re PCT App. No. PCT/US2014/040744, dated Oct. 12, 2014.
Office Action dated Jan. 16, 2015 for U.S. Appl. No. 14/295,148.
Office Action dated Sep. 27, 2017 for U.S. Appl. No. 15/145,631.
Preinterview First Office Action dated Nov. 11, 2014 for U.S. Appl. No. 14/295,224.

* cited by examiner

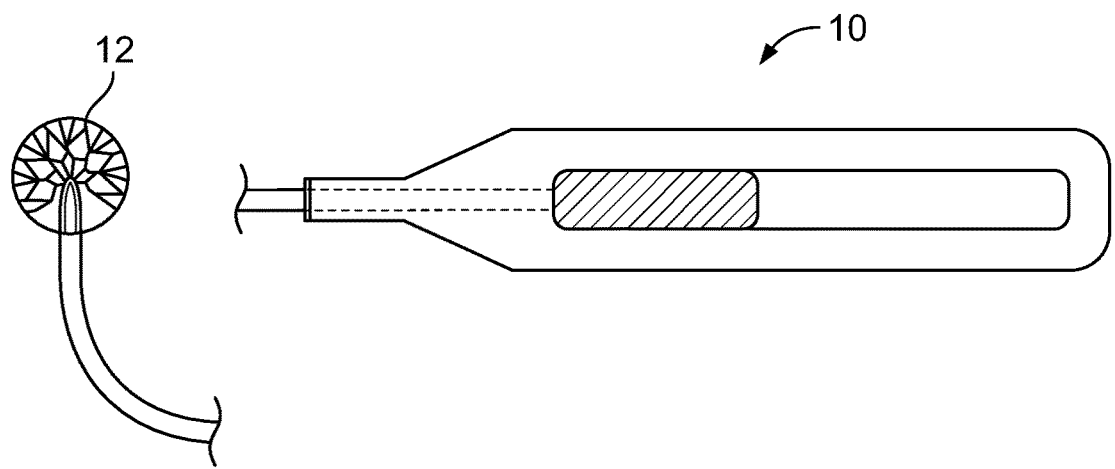
FIG. 2
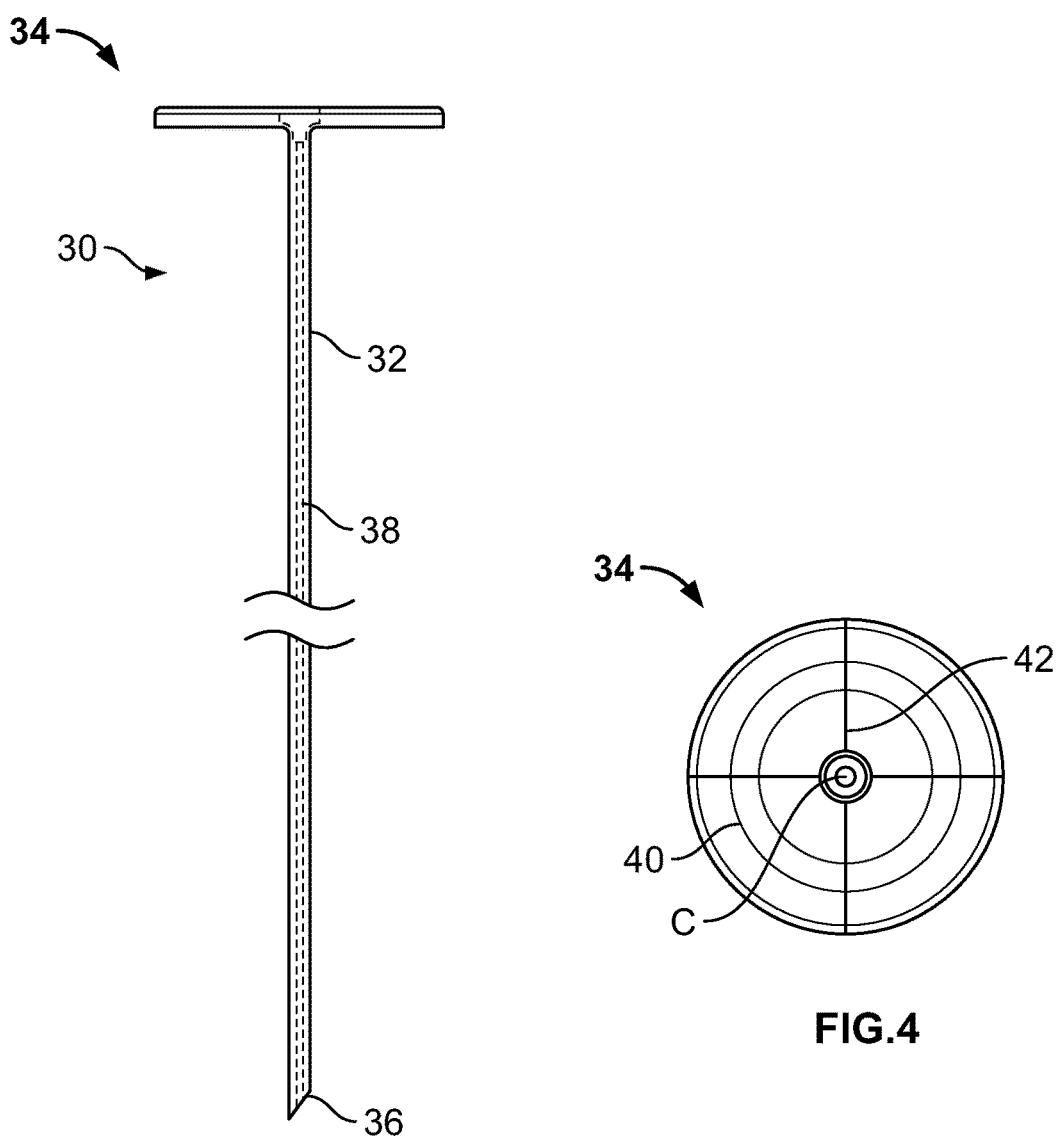
FIG.3
FIG.4

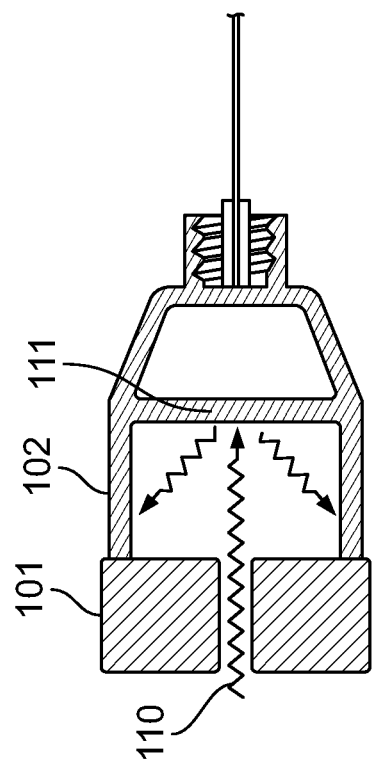
FIG. 13A
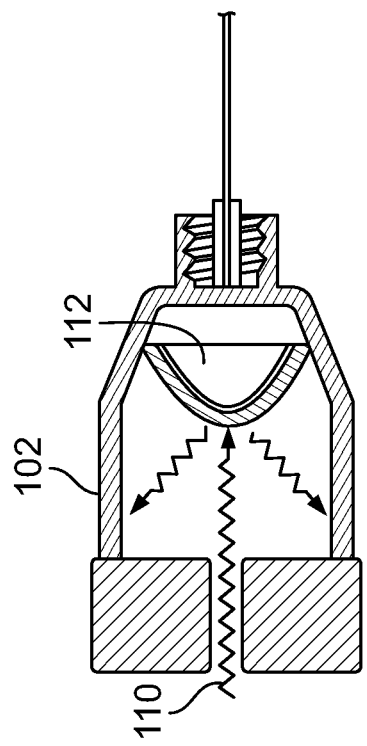
FIG. 13B
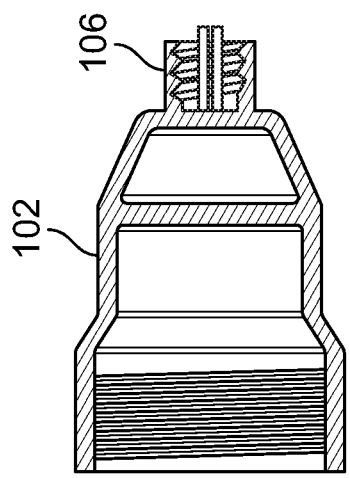
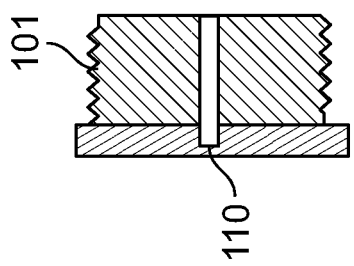
FIG. 12

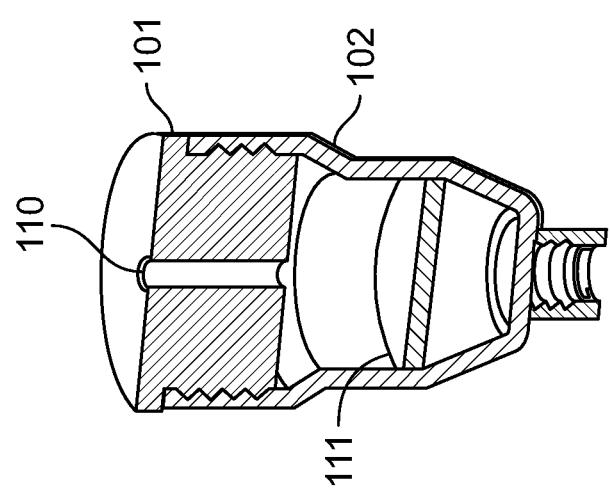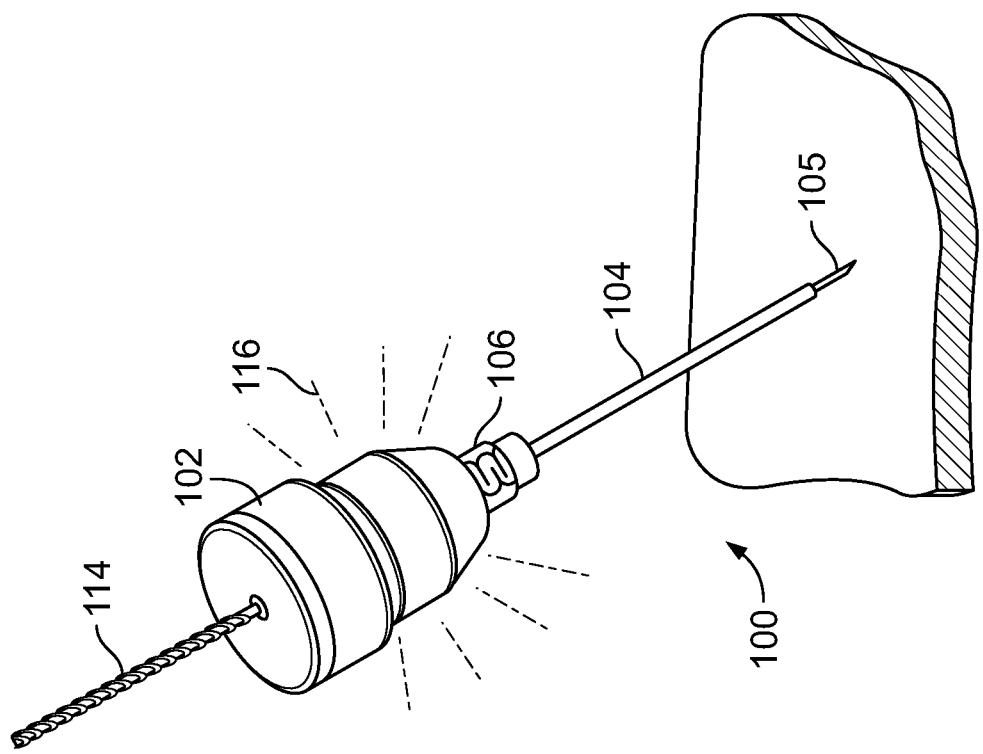

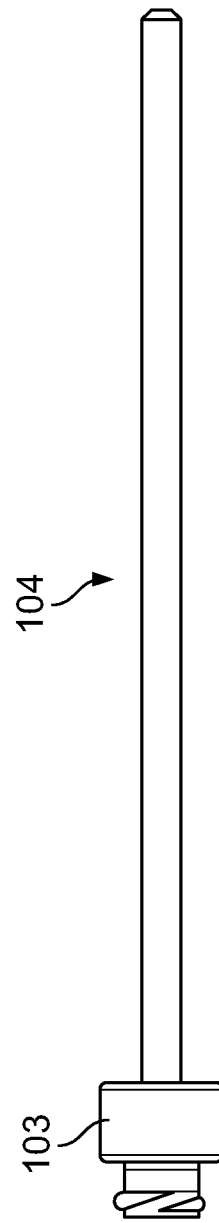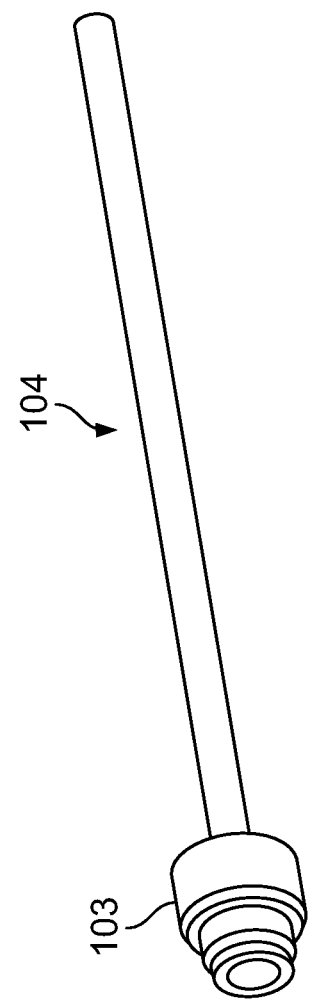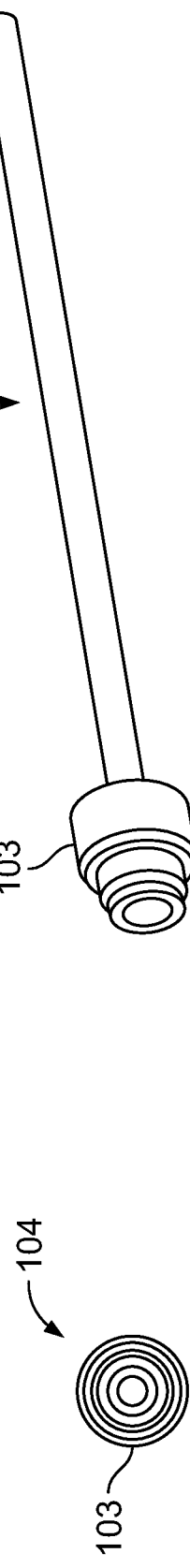

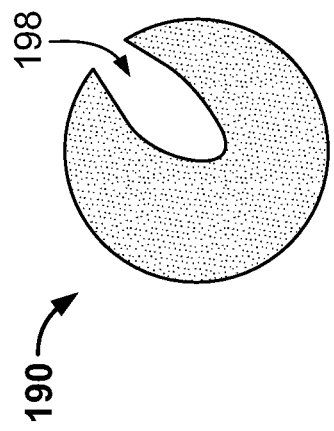
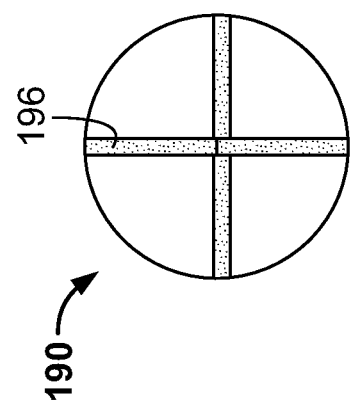
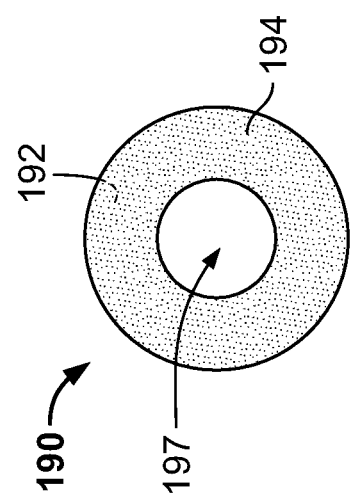
FIG. 19C
FIG. 19B
FIG. 19A

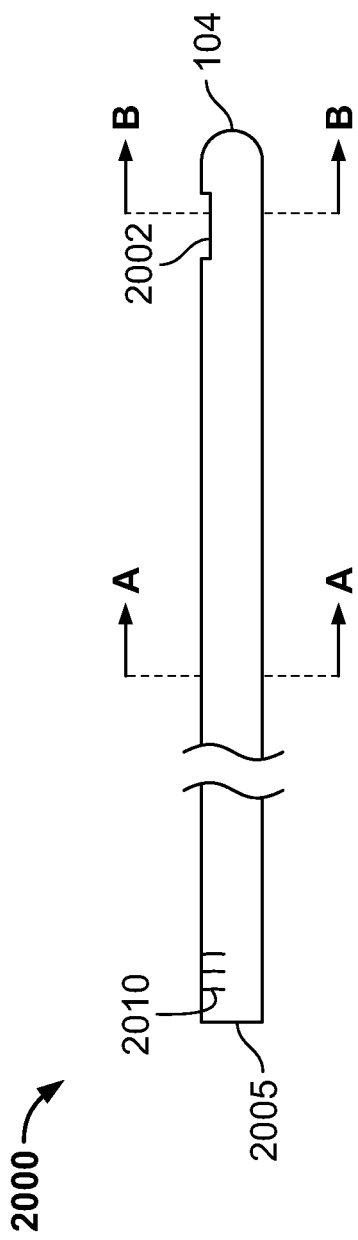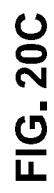
FIG. 20A
FIG. 20B
FIG. 20C

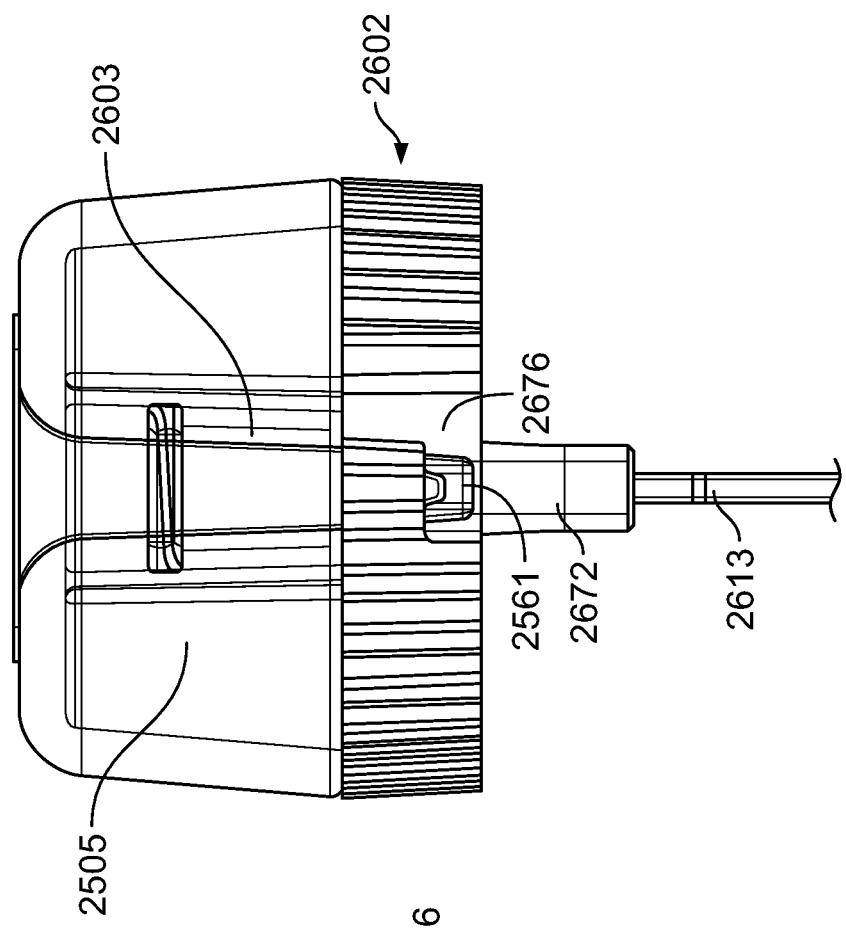
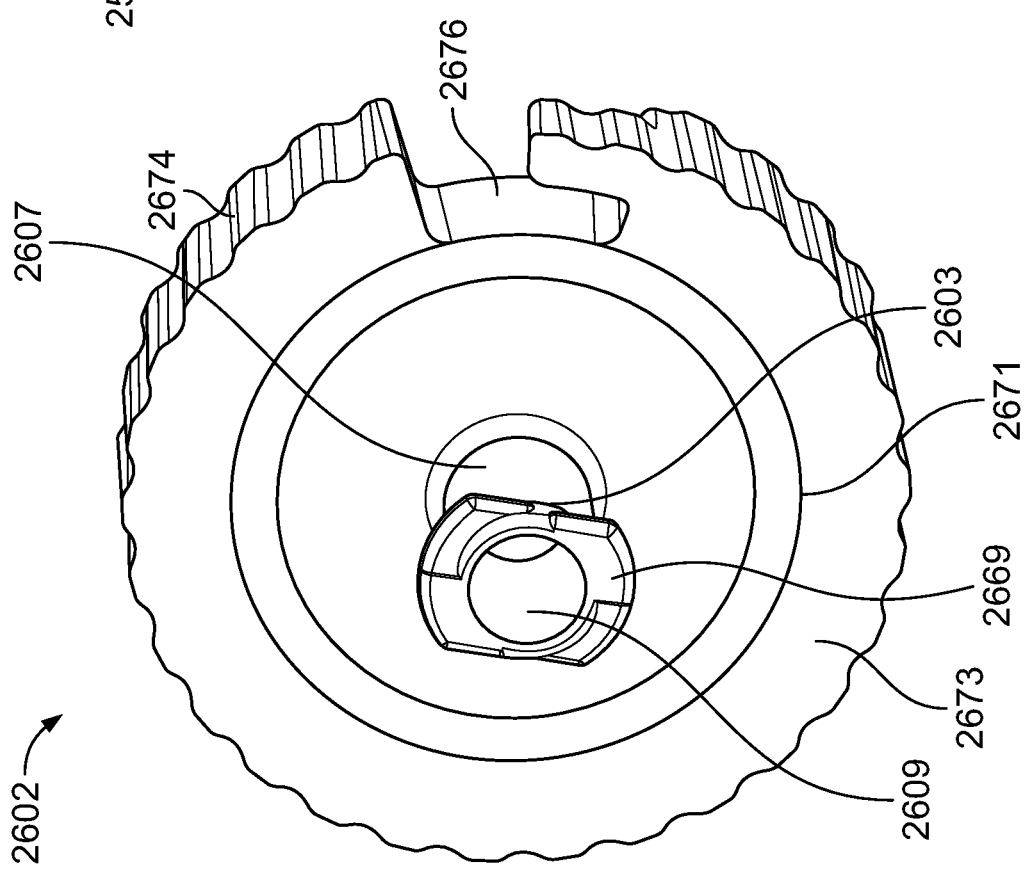
FIG. 26D
FIG. 26C

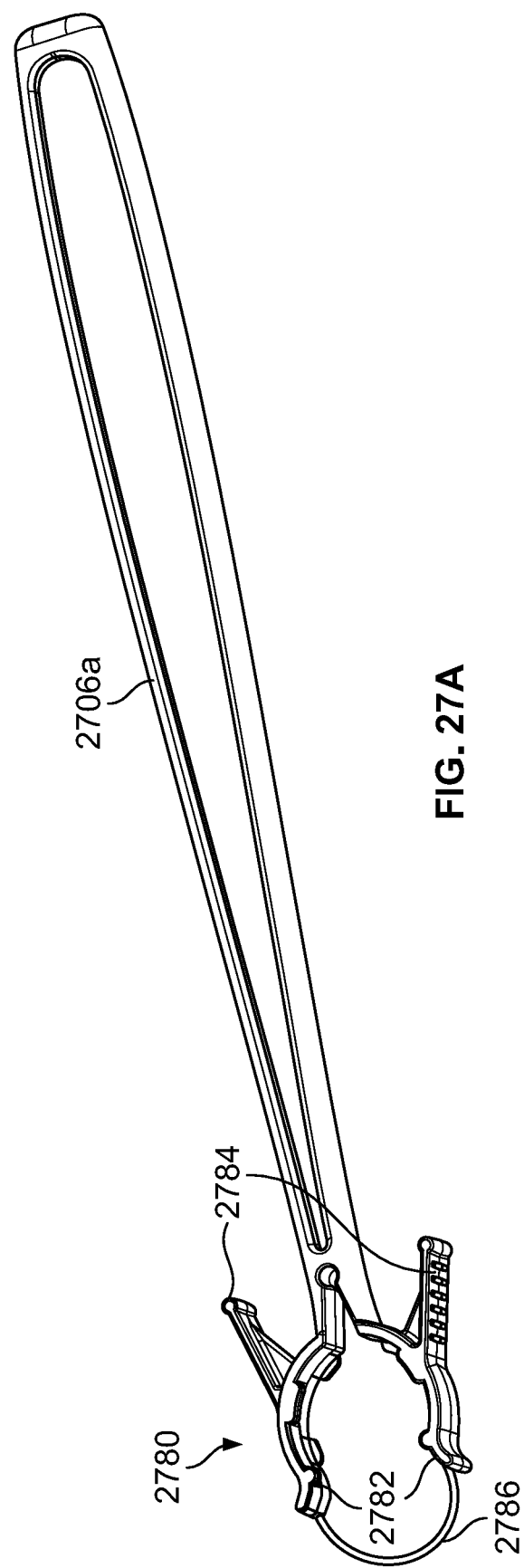

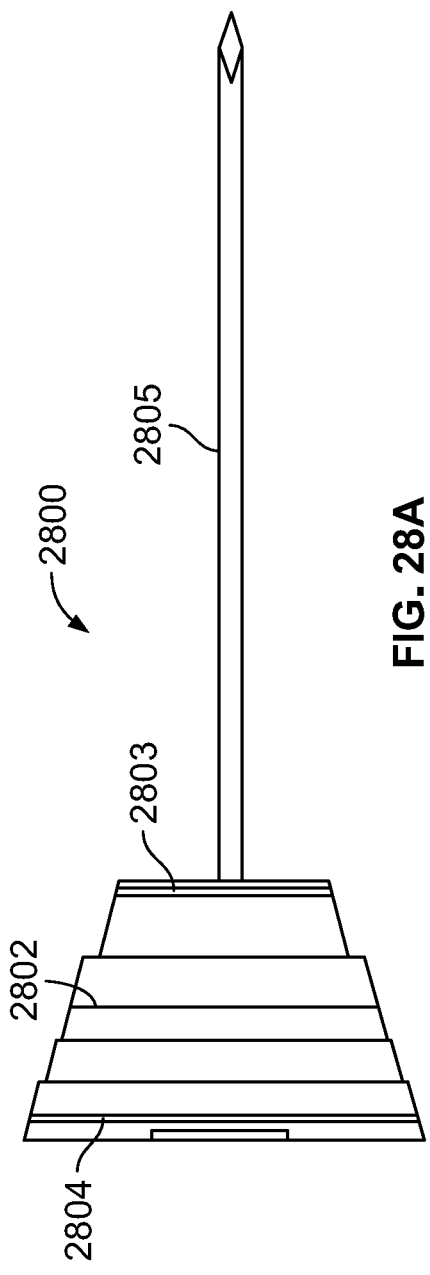
FIG. 28A
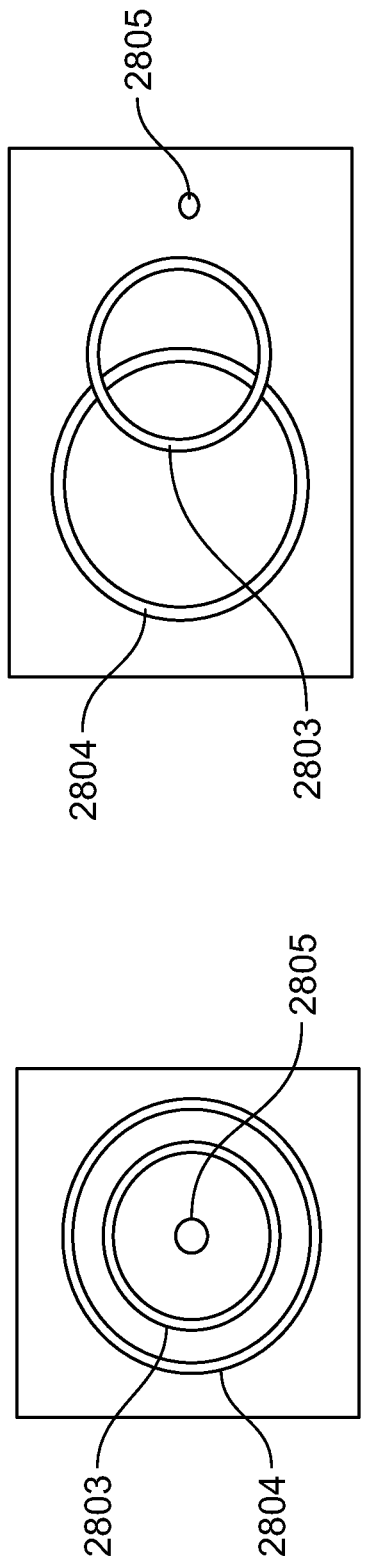
FIG. 28C
FIG. 28B

SECTION A-A
SCALE 2 : 1

DETAIL B
SCALE 8 : 1

METHODS AND APPARATUSES FOR FLUORO-LESS OR NEAR FLUORO-LESS PERCUTANEOUS SURGERY ACCESS

CROSS-REFERENCE TO RELATED APPLICATIONS

The present application relies on U.S. Patent Provisional Application No. 62/490,390, entitled "Methods and Apparatuses for Fluoro-less or Near Fluoro-less Percutaneous Surgery Access", and filed on Apr. 26, 2017, for priority.

The present application is also a continuation-in-part of U.S. patent application Ser. No. 15/890,090, entitled "Methods and Apparatuses for Fluoro-less or Near Fluoro-less Percutaneous Surgery Access", and filed on February 6, 2018, which is a continuation of U.S. Pat. No. 9,918,739, entitled "Methods and Apparatuses for Fluoro-less or Near Fluoro-less Percutaneous Surgery Access", and issued on Mar. 20, 2018, which, in turn, is a continuation of U.S. Pat. No. 9,095,361, entitled "Methods and Apparatuses for Fluoro-less or Near Fluoro-less Percutaneous Surgery Access", and issued on Aug. 4, 2015.

The present application is also a continuation-in-part of U.S. patent application Ser. No. 15/145,631 entitled "Methods and Apparatuses for Fluoro-less or Near Fluoro-less Percutaneous Surgery Access", and filed on May 3, 2016, which is a continuation of U.S. Pat. No. 9,351,758 entitled "Methods and Apparatuses for Fluoro-less or Near Fluoro-less Percutaneous Surgery Access", and filed on Apr. 3, 2015, which, in turn, is a continuation of U.S. Pat. No. 8,998,943 entitled "Methods and Apparatuses for Fluoro-less or Near Fluoro-less Percutaneous Surgery Access", and filed on Jun. 3, 2014.

The present application is also a continuation-in part of U.S. patent application Ser. No. 15/271,414, entitled "Kit and Method for Reduced Radiation Procedures", and filed on Sep. 21, 2016, which in turn, relies on U.S. Patent Provisional Application No. 62/222,037, entitled "Kit For Reduced Radiation Procedures", and filed on Sep. 22, 2015.

All of the above-mentioned applications are incorporated herein by reference in their entirety.

FIELD

The present specification relates to devices and kits for percutaneous surgery access and more specifically to needle placement procedures and devices that minimize or eliminate the use of fluoroscopy, in order to minimize radiation exposure.

BACKGROUND

Percutaneous access is a commonly used step for the treatment and the testing of a variety of diseases and conditions in a plethora of surgical and clinical procedures. An initial step in many forms of percutaneous surgery is the insertion of a wire for later access into an inner portion of a lumen, space, viscous, or organ. An example of this type of access could be placement of a needle through the skin into the kidney for access into one of the calices of the kidney for removing kidney stones, such as in a percutaneous nephrolithotomy (PCNL) procedure. This step of the percutaneous procedure is often one of the most difficult steps and often requires real-time, imaging guidance with ultrasound, CT, or fluoroscopy.

Conventional techniques for needle placement in PCNL can require the use of continuous fluoroscopy during the insertion of the needle into the collecting system. Due to the depth of the tissues surrounding the kidney and the variation of the renal position caused by ventilation the surgeon is asked to hit a small moving target positioned deep inside the body and slight imprecision in needle positioning may lead to complete failure to access the desired space. Subsequently, surgeons are required to grasp a needle using either their hands (placing their hands directly inside the fluoroscopy beam), or using a needle holder or device for holding the needle (decreasing their control and ability to perceive tactile subtle cues regarding tissue densities).

Fluoroscopy guidance accounts for a substantial percentage of the procedural radiation exposure to the patient as well as the surgical team. Every patient poses a different challenge and significant amounts of fluoroscopy can be used to navigate the trocar needle through the patient's anatomy. During needle placement, the amount of fluoroscopy required to obtain access is often several minutes and may be greater than 60 minutes of fluoroscopy time. Sixty minutes of fluoroscopy may be associated with significant radiation exposure and, depending upon the location of the fluoroscopy beam and the size of the patient, may exceed the recommended yearly occupational exposures of radiation. The deterministic effects of radiation occur quickly following exposure and may include sterility, cataracts, skin erythema, and damage to the blood production system, intestinal function, or neurologic function.

In contrast, the stochastic effects of radiation are not directly dose dependent and may occur at any time following radiation exposure and may include genetic damage, cancer, and mental effects. High levels of radiation exposure have been recognized as a potential carcinogenic risk to the patient since the high-energy radiation may cause DNA mutation. It has been shown that a few minutes of fluoroscopy time at standard settings will confer a $\frac{1}{1,000}$ risk of developing fatal cancer. For every 1000 patients exposed to even 10 mSv of radiation, one of those will develop cancer as a result. Further, fluoroscopy exposure is also known to have a cumulative effect over time, increasing the risk of stochastic effects on both the patient and the staff members, including the physician. As there is no safe lower limit (no safe threshold), below which no risk for cancer will occur and since higher the exposure the greater the risk, it is important to decrease the radiation exposure of patients during percutaneous access.

Hence, there is need for needle placement procedures and devices that minimize or eliminate the use of fluoroscopy, in order to minimize radiation exposure. There is also need for devices and methods that simplify surgical procedures and lower the costs associated therewith. Further, there is need for devices and methods of using needle placement procedures that reduce medical waste and the costs of disposal thereof during and after a surgical procedure.

SUMMARY

Certain aspects of the present disclosure are directed toward a device that, when paired with a guidance system, may it be a laser or any image guided methods of needle placement such as ultrasound, ionizing radiation (fluoroscopy, plain film x-ray), computerized tomography, or magnetic resonance imaging, can deliver accurate and precise placement of a needle. When the device is aligned between the imaging system and the target, the device provides visual confirmation of alignment to the user and "paints" the target to facilitate precise insertion of a trocar-cannula needle.

Certain aspects of the present disclosure are directed toward a method of obtaining percutaneous needle access. The method can include selecting a calix for percutaneous access; positioning a flexible ureteroscope in the selected calix; directing a laser guide at a desired needle-insertion angle and in line with a tip of the ureteroscope; aligning a needle with the laser and the ureteroscope tip; and inserting the needle into the selected calix. In certain aspects, if necessary, fluoroscopy can be applied for less than about ten seconds. In other aspects, this method and devices may allow incremental reduction in radiation exposure of 5-10%. In other aspects, this reduction might be between 5 and 99%.

The above-mentioned method can include delivering an instrument to the selected calix. The instrument can be configured to facilitate the insertion of the needle into the selected calix. In certain aspects, the instrument can be identifiable under ultrasound. In certain aspects, the instrument can be a balloon catheter. In certain aspects, the instrument can be a basket catheter.

The present specification discloses a needle access system comprising: a needle hub defined by a planar structure having a first channel therein and two opposing sides, wherein the needle hub further comprises a needle port attached to a first of the two opposing sides and having a first exterior housing and a first lumen positioned within the first exterior housing in fluid communication with the first channel and an aspiration port attached to a second of the two opposing sides and having a second exterior housing and a second lumen positioned within the second exterior housing in fluid communication with the first channel; and a hub housing configured to be attached to the needle hub, wherein the hub housing comprises a base portion, an opaque cap portion, and a non-opaque body portion positioned between the opaque cap portion and the base portion.

Optionally, said needle hub comprises a funnel shaped portion coupled to a disc shaped portion. Optionally, said disc shaped portion comprises said second of the two opposing sides of the needle hub to which the aspiration port is attached.

Optionally, said planar structure is circular and defined by a circumference. An outer surface of said circumference may comprise a plurality of grooves. The planar structure may include a recess in said circumference and said hub housing may further comprise a latching member, wherein said recess is configured to receive said latching member to removably attach said needle hub with said hub housing.

Optionally, said needle port has a hollow cylindrical or conical shape and extends in a direction opposite said aspiration port.

Optionally, the needle access system further comprises a second channel extending through the opaque cap portion, the second channel positioned such that the non-opaque body portion only illuminates when a light source is aligned within a predefined angular range with the second channel.

Optionally, the base portion of the hub housing is removably engaged with the needle hub and configured to receive the aspiration port in a cavity provided in the base portion.

Optionally, the first channel has a diameter that is less than or equal to an outer diameter of a needle configured to pass through said channel.

Optionally, the hub housing comprises a reflective surface positioned in the non-opaque body portion. The reflective surface may comprise a reflective material. The reflective surface may comprise a dome reflector.

Optionally, the needle hub further comprises a luer connector.

Optionally, the opaque cap portion is removably secured to the non-opaque body portion.

Optionally, an inner diameter of the non-opaque body portion is larger than a diameter of the first channel.

The present specification also discloses a method of using a needle access system comprising: providing a needle access system comprising; a needle hub defined by a planar structure having a first channel therein and two opposing sides, wherein the needle hub further comprises a needle port attached to a first of the two opposing sides and having a first exterior housing and a first lumen positioned within the first exterior housing in fluid communication with the first channel and an aspiration port attached to a second of the two opposing sides and having a second exterior housing and a second lumen positioned within the second exterior housing in fluid communication with the first channel; and a hub housing configured to be attached to the needle hub, wherein the hub housing comprises a base portion and an opaque cap portion, and a non-opaque body portion positioned between the opaque cap portion and the base portion; inserting a needle through said first channel and first and second lumens such that said needle extends distally from said needle port; passing a laser light through said opaque cap portion and into said non-opaque body of said hub housing; and maneuvering said needle until said non-opaque body illuminates, thereby indicating that the needle is properly aligned.

Optionally, a maximum angle by which said needle may deviate from an axis of a source of the laser light and still produce illumination of the non-opaque body ranges between 0.1 and 10 degrees.

Optionally, said needle access system further includes a handle configured to be coupled to said needle hub or said hub housing and said method further includes using said handle to manipulate said needle hub or hub housing. The handle may comprise an extension arm having a pair of jaws at one end for grasping said needle hub or said hub housing.

Optionally, the method further comprises: inserting said needle percutaneously into a target tissue of a patient; removing said hub housing to reveal said aspiration port of said needle hub; and connecting a syringe or drainage tube to said aspiration port. The method may further comprise creating negative pressure at said aspiration port to remove fluid from said target tissue.

The present specification also discloses a needle access device configured for insertion into a patient with reduced fluoroscopy, the device comprising: a needle connected to a needle hub; an aspiration port coupled to the needle hub and protruding from a top portion of said needle hub wherein said aspiration port is used for draining out fluids from a body; and, an illumination hub comprising a base portion, an opaque cap portion; a non-opaque body portion positioned between the opaque cap portion and the base portion; and a channel extending through the opaque cap portion, the channel positioned such that the non-opaque body portion only illuminates when a light source is aligned with the channel, wherein the base portion of said illumination hub is removably engaged with said needle hub and is configured to receive the aspiration port in a cavity provided in said base portion.

Optionally, the needle hub comprises a funnel shaped portion coupled to a disc shaped portion. The disc shaped portion may comprise the top portion of the needle hub through which the aspiration port protrudes out.

Optionally, the aspiration port is cylindrical in shape.

Optionally, the aspiration port comprises a threaded outside surface which aids in engaging the aspiration port with a surgical drain/tube or syringe for draining out the fluids.

Optionally, the aspiration port comprises a smooth interior surface which aids in engaging the aspiration port with a smooth tip syringe or surgical drain/tube.

Optionally, an extension arm is coupled to said illumination hub or said needle hub which helps in handing the needle access device from a distance. The diameter of the extension arm may be approximately 5 mm and the length of the extension arm may vary between 5 cm and 15 cm.

Optionally, the illumination hub is threadably secured to the needle hub.

Optionally, the channel has a diameter that is less than or equal to an outer diameter of the needle.

Optionally, the illumination hub comprises a reflective surface positioned in the non-opaque body portion. The reflective surface may comprise a reflective material. The reflective surface may comprise a dome reflector.

Optionally, the needle hub further comprises a luer connector configured to connect to a cannula.

Optionally, the opaque cap portion is removably secured to the non-opaque body portion.

Optionally, the opaque cap portion is threadably secured to the non-opaque body portion.

Optionally, an inner diameter of the non-opaque body portion is larger than a diameter of the channel.

Optionally, the non-opaque body portion is transparent.

Optionally, the non-opaque body portion is translucent.

The present specification also discloses a needle access device configured for insertion into a patient with reduced fluoroscopy, the device comprising: a needle connected to a first hub; an aspiration port coupled to said first hub and protruding from a top portion of said first hub wherein said aspiration port is used for draining out fluids from the body; and, a second hub comprising a base portion, an opaque cap portion; a non-opaque body portion positioned between the opaque cap portion and said base portion; and a channel extending through the opaque cap portion, the channel positioned such that the non-opaque body portion only illuminates when a light source is aligned with the channel, wherein the base portion of said second hub is removably engaged with said first hub and is configured to receive the aspiration port in a cavity provided in said base portion.

Any component in any embodiment can be combined or used with any other component in another embodiment, unless otherwise stated.

The aforementioned and other embodiments of the present specification shall be described in greater depth in the drawings and detailed description provided below.

BRIEF DESCRIPTION OF THE DRAWINGS

These and other features and advantages of the present specification will be appreciated, as they become better understood by reference to the following detailed description when considered in connection with the accompanying drawings:

FIG. 2 illustrates an exemplary basket catheter that can be used with the methods described in accordance with embodiments of the present specification;

FIG. 3 illustrates an exemplary embodiment of a needle in accordance with an embodiment of the present specification;

FIG. 4 illustrates a top view of the needle shown in FIG. 3 having concentric rings to provide a target for laser guidance in accordance with an embodiment of the present specification;

FIG. 12 illustrates a cross-sectional view of a cap and a proximal portion of an embodiment of a trocar needle;

FIG. 13A illustrates a cross-sectional view of an embodiment of a trocar needle having a reflective coating plate;

FIG. 13B illustrates a cross-sectional view of an embodiment of a trocar needle having a dome reflector;

FIG. 15D illustrates a partial cross-section of a proximal portion of the trocar needle shown in FIG. 15A in accordance with an embodiment of the present specification;

FIG. 16 illustrates a perspective view of an exemplary embodiment of the assembly indicating that the assembly is properly aligned;

FIG. 18A illustrates a side view of an exemplary embodiment of a cannula;

FIG. 18B illustrates an end view of the cannula shown in FIG. 18A in accordance with an embodiment of the present specification;

FIG. 18C illustrates a perspective view of the cannula shown in FIG. 18A in accordance with an embodiment of the present specification;

FIG. 19A illustrates an exemplary sticker provided in a reduced radiation kit, in accordance with an embodiment of the present specification;

FIG. 19B illustrates the exemplary sticker having a marking on a display face, in accordance with an embodiment of the present specification;

FIG. 19C illustrates the exemplary sticker having a recess adapted to allow needle access to a patient's skin, in accordance with an embodiment of the present specification;

FIG. 20A illustrates a side view of an exemplary guidewire provided in the reduced radiation kit, in accordance with an embodiment of the present specification;

FIG. 20B is the transverse cross-sectional view of the guidewire along the line A-A indicated in FIG. 20A;

FIG. 20C is the transverse cross-sectional view of the guidewire along the line B-B indicated in FIG. 20B;

FIG. 26C illustrates a top perspective view of the needle hub shown in FIG. 26A;

FIG. 26D illustrates a side view of a needle hub engaged with a hub housing;

FIG. 27A illustrates an extension arm for handling a needle assembly in accordance with an embodiment of the present specification;

FIG. 28A is a schematic diagram illustrating a needle assembly comprising radiopaque markers for needle alignment in accordance with an embodiment of the present specification;

FIG. 28B is a schematic diagram illustrating a central lumen and metal rings of a needle assembly observed under fluoroscopic radiation when the needle assembly is properly aligned in accordance with an embodiment of the present specification;

FIG. 28C is a schematic diagram illustrating a central lumen and metal rings of a needle assembly observed under fluoroscopic radiation when the needle assembly is not properly aligned in accordance with an embodiment of the present specification;

DETAILED DESCRIPTION

Figure 1:
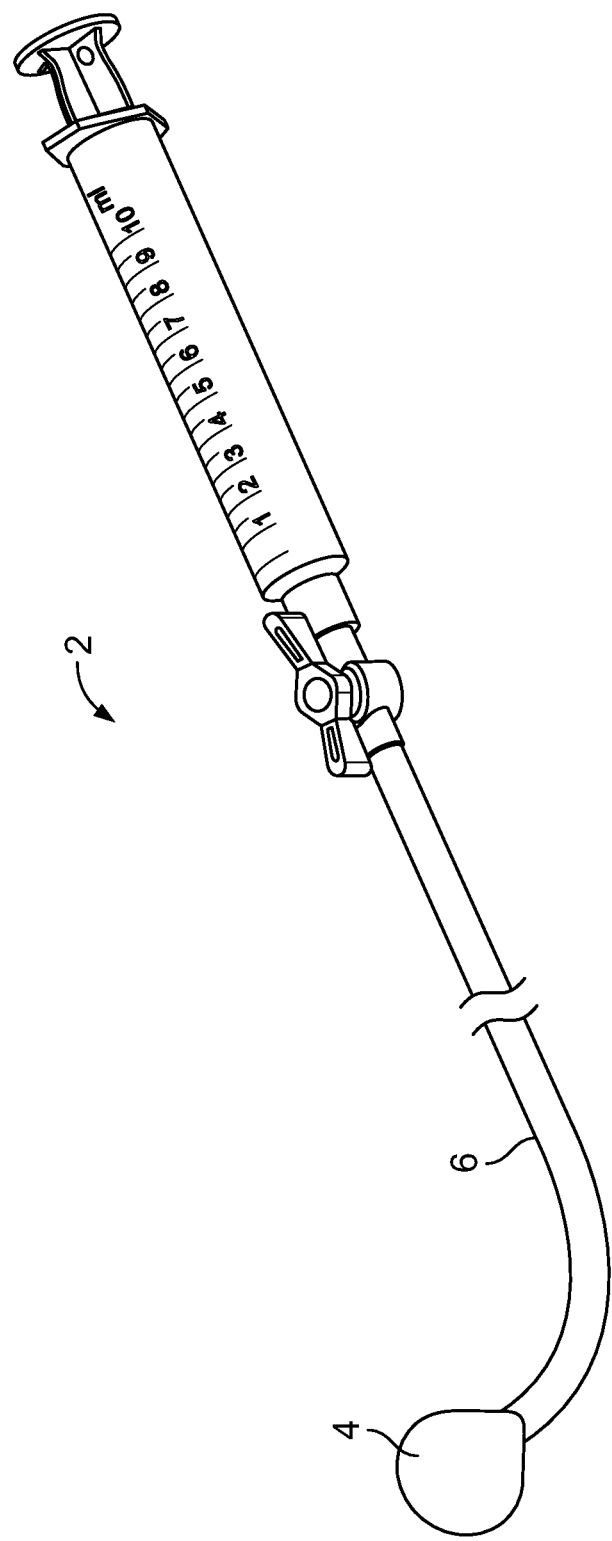
FIG. 1 illustrates an exemplary balloon catheter that can be used with the methods described in accordance with embodiments of the present specification.

The present specification relates to devices and kits for percutaneous surgery access and more specifically to needle placement procedures and devices that minimize or eliminate the use of fluoroscopy, in order to minimize radiation exposure.

The present specification is directed towards multiple embodiments. The following disclosure is provided in order to enable a person having ordinary skill in the art to practice the specification. Language used in this specification should not be interpreted as a general disavowal of any one specific embodiment or used to limit the claims beyond the meaning of the terms used therein. The general principles defined herein may be applied to other embodiments and applications without departing from the spirit and scope of the specification. Also, the terminology and phraseology used is for the purpose of describing exemplary embodiments and should not be considered limiting. Thus, the present specification is to be accorded the widest scope encompassing numerous alternatives, modifications and equivalents consistent with the principles and features disclosed. For purpose of clarity, details relating to technical material that is known in the technical fields related to the specification have not been described in detail so as not to unnecessarily obscure the present specification.

In the description and claims of the application, each of the words "comprise" "include" and "have", and forms thereof, are not necessarily limited to members in a list with which the words may be associated. It should be noted herein that any feature or component described in association with a specific embodiment may be used and implemented with any other embodiment unless clearly indicated otherwise.

Any feature, structure, or step disclosed herein can be replaced with or combined with any other feature, structure, or step disclosed herein, or omitted. Further, for purposes of summarizing the disclosure, certain aspects, advantages, and features of the inventions have been described herein. It is to be understood that not necessarily any or all such advantages are achieved in accordance with any particular embodiment of the inventions disclosed herein. No aspects of this disclosure are essential or indispensable.

Given the risks associated with fluoroscopy exposure described above, there is a need to reduce procedural ionizing radiation. One such solution is to reduce fluoroscopy use during percutaneous access to tissue, while simultaneously maintaining accurate needle placement. As such, there is a need for a device that will allow precision and accuracy without continuous fluoroscopy use for recurrent visualization.

In embodiments, the present specification is directed towards a needle that allows for facile orientation and direction of a trajectory when used in conjunction with reduced fluoroscopy settings.

The devices and methods described herein are designed to simplify procedures for percutaneous access and significantly reduce radiation exposure to the surgeon, patient, and staff members. Although the disclosure below is discussed in connection with the kidneys, the methods and devices described herein can be used to obtain access to other structures, lumens, organs, and spaces.

Method of Inserting an Ureteroscope without Image Guidance

Placing a needle into the kidney for renal access for stone surgery will be used as an example of this technique. However, similar concepts and principles would also apply to other procedures, such as placing probes into the kidney to treat a renal cancer, placing access into an infected fluid collection for drainage of an abscess, placing tubes into any space to serve as a drain, (i.e., pleural space, peritoneal drain, cholecystectomy drain, bladder drain, lymphocele drain, pericardial space, etc.).

In describing the percutaneous access into the kidney as an example, the patient is positioned into a prone and split-legged position to allow simultaneous access into the kidney and the urethra. Using a flexible cystoscope, a surgeon can place a guide wire into the kidney to allow later insertion of an ureteroscope into the kidney. After positioning a first guide wire, the surgeon can optionally position a dual lumen type catheter in the kidney to allow the placement of a second guide wire, so there are both a working wire and a safety wire positioned in the kidney. In certain aspects, the guide wires are placed into the kidney in a retrograde fashion using no image guidance at all. The two guide wire lengths are compared to confirm that both wires were correctly positioned in the kidney.

The working and/or safety guide wires comprise one or more of the following features. In certain aspects, the guide wire is an angle-tipped guide wire that has a lubricious coating to allow it to slip easily above any ureteral obstruction. In certain aspects, the guide wire includes one or more features to facilitate visualization. For example, in an embodiment, the guide wire is designed to produce a highly echogenic profile allowing it to be easily visualized using ultrasound. In an embodiment, a shaft of the guidewire is rounded at the tip to allow easier insertion but has a flattened shape proximal to the tip (e.g., about 1 to 5 cm proximal to the tip of the wire) to allow the wire to be more easily seen under ultrasound guidance. In embodiments, the flattened surface of the wire reflects the acoustic beams back at a similar angle because of which the wire is easily seen under ultrasound. In embodiments, the above described wire can also be easily seen under very low dose fluoroscopy levels. In another embodiment, the guide wire comprises one or more radiopaque markers to enhance fluoroscopic visualization. In an embodiment, the guide wire comprises interval marks (e.g., placed every one cm) to allow insertion of these wires under endoscopic visualization. For example, the wire might be black with white markings identifying the distances. In an embodiment, the wire is of white color with blue markings identifying the length marks. The colors could be any color that would allow easy identification endoscopically and externally. In some embodiments, the guide wire includes a nitinol core and/or a PTFE coating. In some embodiments, the guide wire includes a lubricious coating to allow easy insertion. In some embodiments, the guidewire comprises a retractable square outer sheath through which the guide wire is placed into a kidney to allow appropriate placement and then an acoustically dense sheath is passed over the wire to allow even the tip to be seen easily under ultrasound. In certain aspects, the guide wire is etched with an acoustically dense surface to allow the wire to be seen easily under ultrasound guidance. In an embodiment, the guide wire comprises an Amplatz extra stiff type wire that is floppy at both ends and therefore allows the insertion of a flexible ureteroscope into the kidney without any trauma. In some embodiments, the guide wire comprises a standard 0.035 or 0.038 Teflon-coated guide wire or a lubriciously coated guide wire.

The surgeon can advance a flexible ureteroscope over a working wire into the ureter using a fluoro-less technique. The technique for insertion of the ureteroscope is particularly important to prevent a migration of ureteral stones outside of the ureter, and to facilitate correct positioning of the ureteroscope. In general, if recent imaging shows that there are no stones present inside the ureter, the ureteroscope is placed over the working wire and advanced until the ureteroscope tip is in the proximal ureter a distance of 15 to 20 cm in a female and 30-35 cm in a male with normal sized phallus. If recent imaging shows a mid-ureteral stone, the flexible ureteroscope is advanced only into the distal ureter. If recent imaging shows only a distal ureteral stone, the flexible ureteroscope is advanced just through the ureteral orifice.

The actual passage of the ureteroscope may occur in several ways. In an embodiment, the surgeon advances the ureteroscope tip over the wire while an assistant holds a handle of the ureteroscope and the wire in a steady and fixed position. This allows the surgeon to delicately feel the tactile feedback from the points of resistance as the ureteroscope is advanced over the wire including the urethral sphincter, bladder neck, and ureteral orifice. If resistance is met at an appropriate depth for the ureteral orifice (and the ureteroscope does not progress), the ureteroscope is pulled 2-3 cm back and rotated 90 degrees and another attempt at advancement is made. If this is not successful, the ureteroscope can be pulled back another 2-3 cm and rotated in the same direction another 90 degrees before another attempt is made. This is repeated until the ureteroscope has returned back to the original starting position. If the ureteroscope has rotated 360 degrees and there has been no passage through the ureteral orifice a Foley is inserted into the bladder in order to empty the bladder and the process is repeated in its entirety.

In another method, the ureteroscope may be passed with a light cord and camera connected so that some subtle visual details may be obtained as the ureteroscope is advanced up the ureter.

In a third method the ureteroscope is advanced using a "bare naked" technique up the ureter without the use of a safety wire and the ureteroscope is used as the safety channel itself In this technique normal saline or any other irrigation fluids are injected under pressure to provide visualization of the important anatomic structures. If the ureteroscope has difficulty engaging the ureteral orifice a guide wire is inserted into the ureteral orifice to help engage the ureteroscope tip into the ureter and the ureteroscope could then be advanced into the ureter under direct vision.

With all the techniques, once the ureteroscope is positioned in the ureter it is slowly advanced up the ureter in a retrograde fashion from the point of insertion under direct vision. The flexible ureteroscope is advanced slowly in a retrograde fashion from the point of insertion either until a stone is encountered or until the renal calices are identified.

The next step in an ureteroscopic-assisted form of the Laser DARRT technique is for the surgeon under direct endoscopic vision to select a desired calix for percutaneous access of a collecting system. After selecting the ideal calix for puncture, the surgeon can determine an optimal access tract using CT, ultrasound, or fluoroscopic guidance.

Fluoroscopy can optionally be performed with a single pulse or a pulse rate of one pulse per second to visualize a tip of an ureteroscope. The ureteroscope is very dense and can be seen easily at even very low mA and kVp settings. One pulse per second is significantly lower than the conventional pulse rate, which can be about 25 to about 30 pulses per second.

In embodiments, after the calix that provides a best access to the kidney has been selected ureteroscopically, ultrasound can be used to map out the pleura, lung, and intra-abdominal organs. Assuming that there are no organs in the way and that the lung is a safe distance away from the puncture site, the needle can be inserted directly under ultrasound guidance into the desired calyx. In an embodiment, the needle is between 14 and 25 gauge, e.g., between about 18 gauge and 20 gauge. In an embodiment, the needle is passed into the desired calyx using a "free hand" approach or the needle is directed using a guide that directs the needle into the desired calyx and is attached to an US probe, CT scanner, or MRI scanner. For example, in an embodiment, a special instrument is used to provide an acoustically dense image to simplify targeting under US guidance. As shown in FIG. 1, in an embodiment, the acoustically dense structure is a balloon catheter 2 configured for identification under ultrasound. The balloon 4 is inflated with air or ultrasonic contrast material or alternatively with saline to provide a fluid filled target.

In an embodiment, the balloon catheter 2 is configured for insertion through a flexible ureteroscope channel. In an embodiment, the balloon catheter shaft 6 is between about 0.5 Fr and about 3.3 Fr. In some embodiments, the shaft is about 2.2 Fr. In some embodiments, the shaft has marks at 1 cm distance from its distal end and 1 cm from its proximal end, and every 1 cm interval, along its length. In embodiments, the balloon is made of a strong and expandable polymer, such as silicone, latex, vinyl, Gore-tex®, or any other expandable coverings. In embodiments, the balloon material is acoustically similar to saline or is acoustically dense to provide a dense target. Once the needle is inserted into the calyx, the balloon is deflated and removed through the ureteroscope. In some embodiments, a ureteral access sheath is placed and the balloon is removed with the ureteroscope through the ureteral access sheath.

In an embodiment, the acoustically dense instrument is a basket catheter. FIG. 2 illustrates an exemplary basket catheter 10 designed to create an acoustic interface. In embodiments, the basket 12 is formed from an acoustically dense material or metal, such as Nitinol. In an expanded configuration, the basket 12 forms, for example, a large open sphere having an expanded diameter between about 1 mm and about 20 mm. In some embodiments, the expanded diameter is about 10 mm. In some embodiments of this device, a small gauge wire is inserted percutaneously, directly into the basket 12 under ultrasound guidance and then the basket 12 is closed over the wire to allow the wire to be pulled into the proximal ureter. Once the small wire is in the proximal ureter, past the stone, a sheath is inserted over the wire to allow conversion to a larger 0.035 or 0.038 guide wire for subsequent dilation.

In embodiments, the respiration is paused by the anesthesiologist after a period of hyperventilation. For example, the respiration is routinely paused during end expiration to move the lungs as far away as possible from the site of needle access. In an embodiment, the respiration is held during other parts of the respiratory cycle, for example, during inspiration to move the kidney below the rib.

In another embodiment, fluoroscopy is used to help direct a needle into the desired calyx instead of using Ultrasound. In an embodiment, an external instrument is used to provide an obvious target to assist in targeting the correct calyx. In an embodiment, the external instrument is positioned on the skin in the path of the fluoroscopy beam so that the beam is aligned with the instrument on the skin and the desired calyx for puncture.

In an embodiment, using a C-arm placed at about 0 to about 45 degrees of oblique rotation, or between about 15 degrees and about 30 degrees of oblique rotation, such as about 30 degrees, the surgeon uses a heavy clamp to determine the skin site that leads to the desired trajectory for PCNL insertion. For example, after using the C-arm to generate an x-ray image and identifying the target location based on the image, the surgeon marks the target using a clamp or other dense, metal instrument. Use of the instrument to mark the target access position is optional. In some cases, figuring out where the needle is can be challenging, for example, if the access is lateral and the clamp set on the patient may slip off of the patient. Therefore, in some embodiments, the needle is provided with a metal target that is configured to be rested on the patient. In some embodiments, the metal target comprises concentric rings held together on the edges of adjacent rings and having a 2 mm, 3 mm or 4 mm hole in the center to make determining the location for the needle deployment more easy to identify. The ring structure may have a handle to make it easier to place. In alternative embodiments, the metal rings are replaced by a sticky series of radio-opaque grids that have an adherent surface which is placed upon the patient and sticks to the surface of the patient's body. The grids are visible under fluoroscopy and allow a surgeon to determine an angle of entry into the kidney (or any other organ) using the sticky grid that was attached to the patient.

Figure 8A:
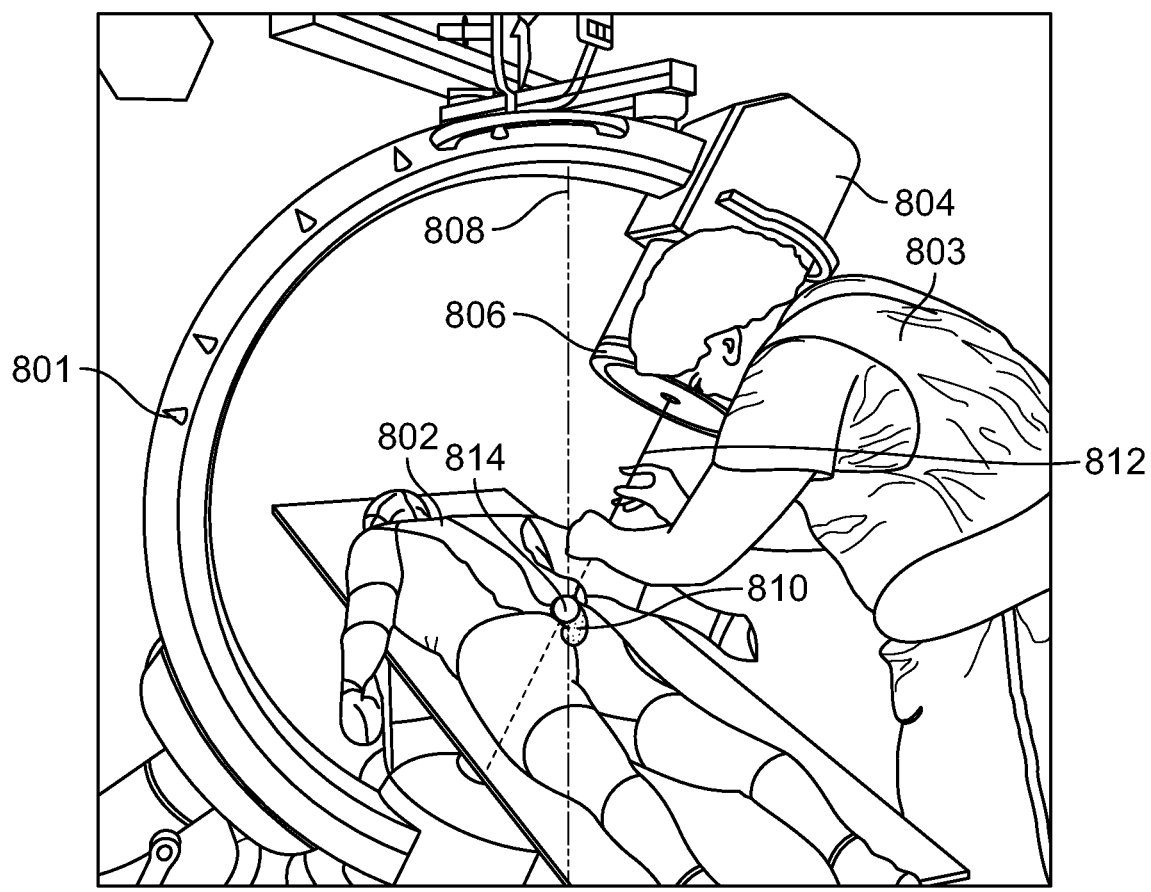
FIG. 8A illustrates a method for laser-guided percutaneous access in accordance with an embodiment of the present specification.
Figure 8B:
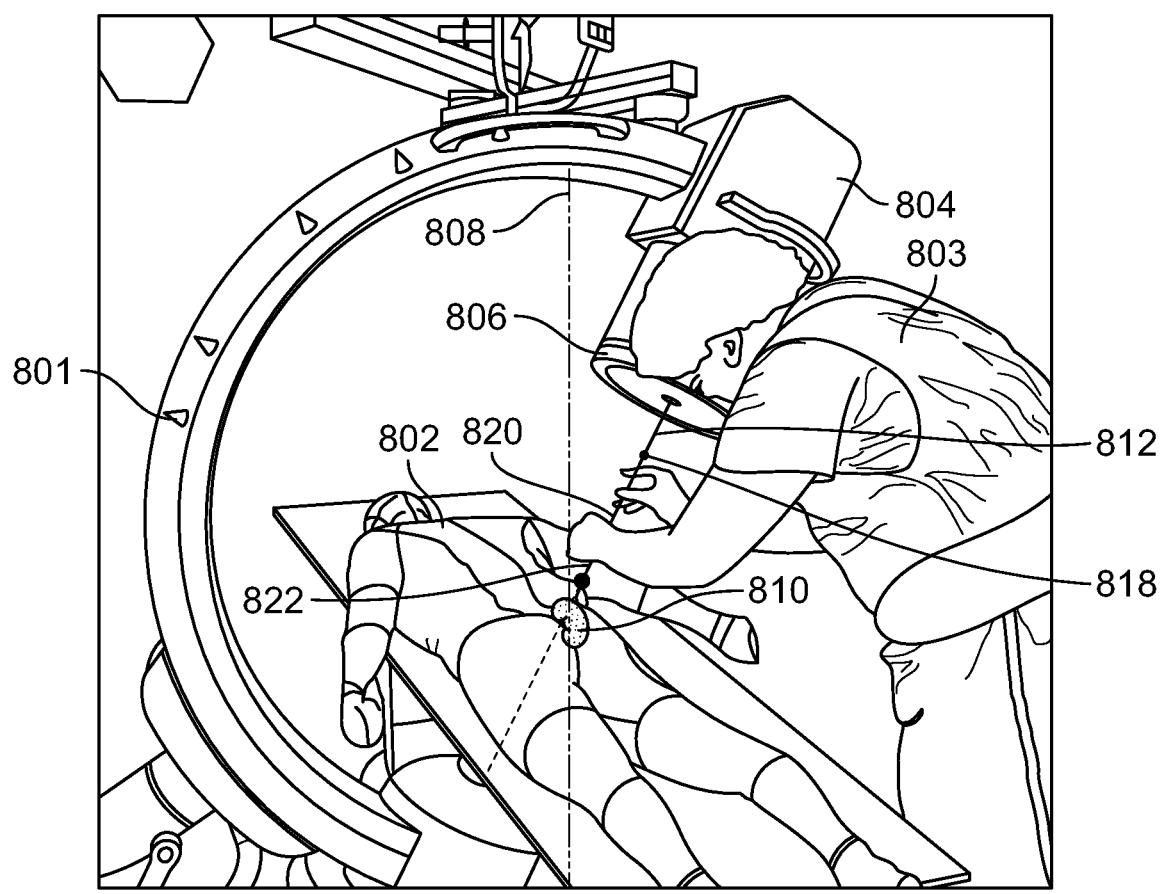
FIG. 8B illustrates a method for laser-guided percutaneous access in accordance with an embodiment of the present specification.

FIG. 8A through FIG. 8D illustrate a method of laser-guided percutaneous access in accordance with an embodiment of the present specification. For example, as shown in FIG. 8A, a percutaneous needle access procedure is being performed by a surgeon 803 by using a C-arm 801 comprising a head 804 coupled with a laser guide 806. The laser guide 806 is configured to facilitate the alignment and insertion of a needle 820 (shown in FIGS. 8B-8D) without fluoroscopy or with decreased fluoroscopy and without other image guidance. The laser guide 806 is directed at a desired needle-insertion angle, for example, in line with a tip of a clamp or marker 814 placed on the body of a patient 802, and a ureteroscope (not shown) placed inside a desired calyx of the patient's 802 kidney 810 that is selected for puncture. In an embodiment, the desired needle-insertion angle is zero degrees and/or less than or equal to about 45 degrees relative to a vertical axis 808. In an embodiment, the insertion angle ranges from 0 degrees to 30 degrees. In another embodiment, the insertion angle ranges from 15 degrees to 45 degrees, and is approximately 30 degrees.

After the laser guide 806 is directed at the desired access location and angle, a needle hub 818 (shown in FIG. 8B) is aligned with the laser beam 812 that is emitted from the laser guide 806. Once the needle hub 818 is aligned with the laser beam 812 and the needle hub 818, needle tip 822 (shown in FIG. 8C), and ureteroscope tip (not shown) within the patient's 802 kidney 810 form a single point trajectory on the C-arm 801 (shown in FIG. 8C), the surgeon may insert the needle 820 without any fluoroscopy activation or with greatly minimized fluoroscopy exposure used only to adjust for slight variations in respiratory excursion (shown in FIG. 8D).

Figure 8C:
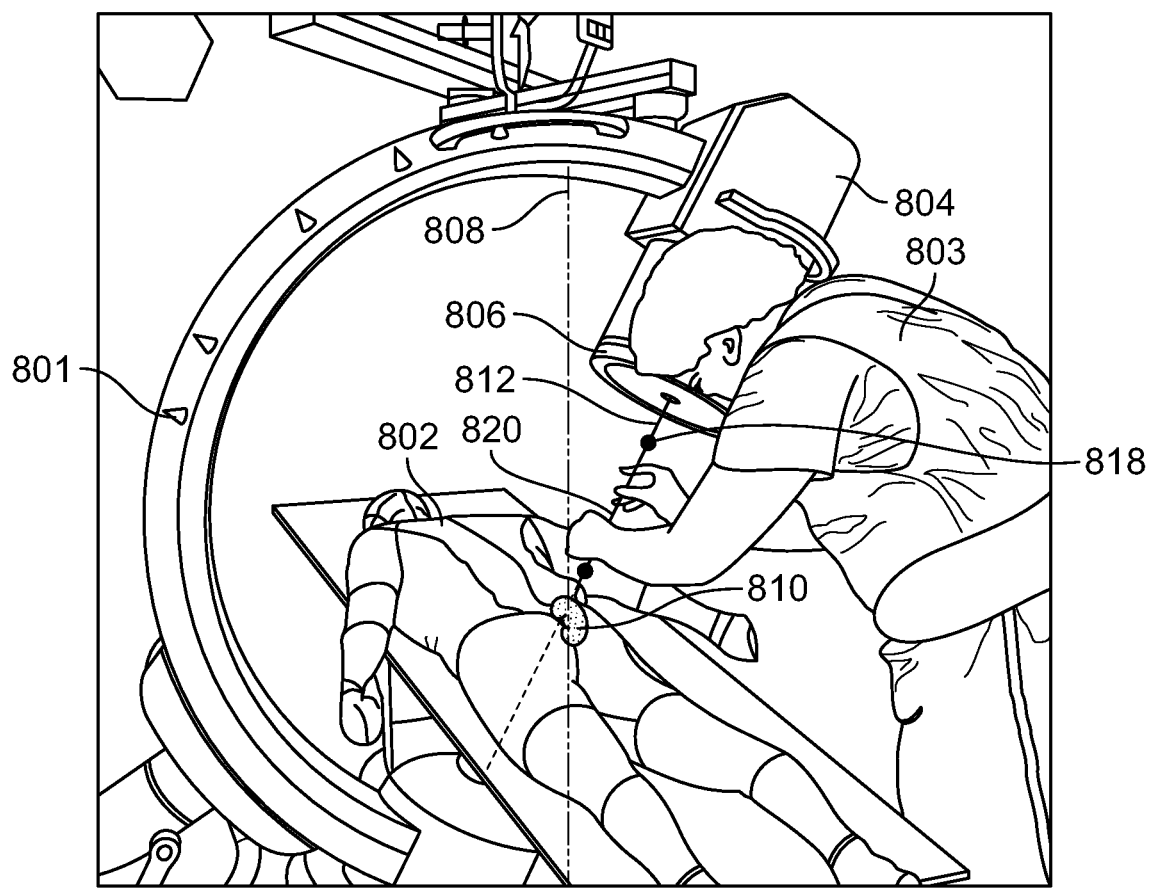
FIG. 8C illustrates a method for laser-guided percutaneous access in accordance with an embodiment of the present specification.
Figure 8D:
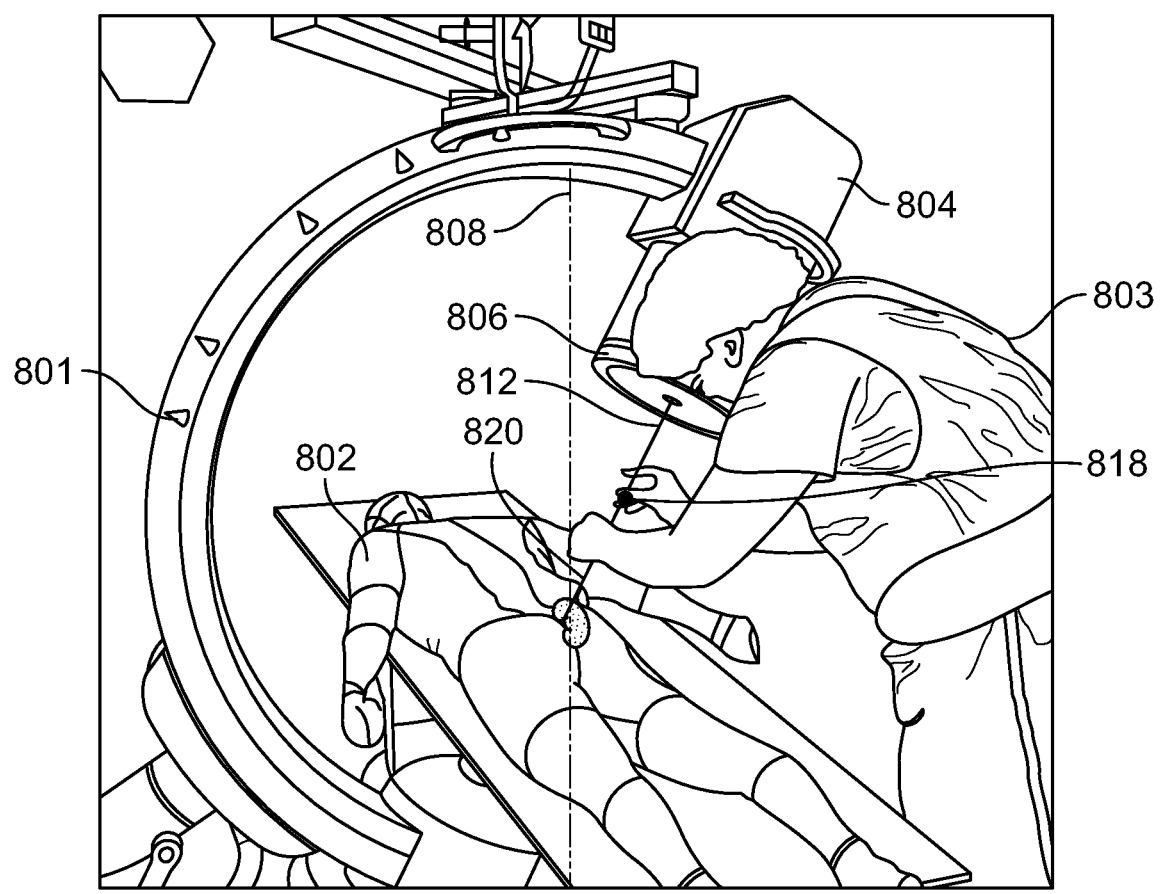
FIG. 8D illustrates a method for laser-guided percutaneous access in accordance with an embodiment of the present specification.

As shown in FIG. 8C, the laser beam 812 is centered on the hub 818 of the needle 820, such that the hub 818 is illuminated, ensuring that the needle 820 is inserted at a predefined trajectory. The depth of insertion can be determined based on a pre-operative CT scan or ultrasound measurements where the depth from the skin to the desired calyx was measured. Alternatively, the desired depth of insertion is marked on the needle 820 based on the initial images of the target using a mark or removable clip, tape or bracket. The bracket is attached to the needle 820 reversibly so that the needle would be inserted at the desired depth, on the desired trajectory as directed by the laser beam 812. Once at the desired depth, the bracket is removed.

Once the needle 820 has been inserted, the C-arm 801 is rotated and activated with a single pulse to confirm the depth of the needle 820. The C-arm 801 is rotated to an angle that is on the opposite side of the vertical axis 808 from the needle insertion angle. The angle can be equal to the needle insertion angle. For example, if the desired insertion angle is about 30 degrees, the C-arm 801 is rotated 60 degrees, such that the C-arm 801 is positioned 30 degrees relative to the vertical axis 808 opposite the needle insertion angle. Usually, if the C-arm 801 is rotated 30 degrees toward the surgeon, the depth of the needle 820 within the kidney 810 is checked by rotating the C-arm 801 to 30 degrees away from the surgeon. Additionally or alternatively, the surgeon can judge the depth of the needle 820 within the kidney 810 by watching the ureteroscope's image to determine under direct vision when the needle 820 enters a collecting system.

With the needle 820 in place, a wire is passed from the insertion needle 820 into the collecting system. The direct endoscopic vision of the internal tip 822 of the needle 820 facilitates placement of a guidewire.

In an embodiment, an end of the guidewire is grasped with a basket passed in a retrograde fashion through the ureteroscope and used to grasp the guidewire as described above. This basket is used to pull the wire down the patient's 802 ureter (not shown) to establish through and through access out the patient's 802 urethra, or alternatively to establish access only into the proximal ureter beyond the level of any stone or obstruction.

In an embodiment, a ureteral access sheath is placed in a retrograde fashion using a completely fluoro-less or minimal fluoroscopy technique. This ureteral access sheath allows the ureteroscope to be re-inserted into the kidney multiple times.

After positioning the guidewire, the guidewire is converted to a conventional or stiff wire for subsequent dilation of the tract from the skin into the collecting system of the kidney 810. The patient's 802 skin is incised with a scalpel to a desired size depending on the size of a sheath being employed for dilation. Next, a dilating balloon or serial dilation device is placed at a desired depth using the ureteroscope under direct vision to avoid the use of fluoroscopy.

In embodiments, the ureteroscope is used to watch the tip of the balloon catheter to enter the collecting system of the kidney 810 and then to position the dilating balloon or serial dilator so that the maximal dilation occurs just inside the edge of the kidney's 810 caliceal collecting system. The desired depth may be determined on a first of a serial dilator, if serial dilation is to be performed. The determined depth is used to insert the subsequent dilators using a bracket, using preplaced markings placed upon the dilators or a mark placed upon the dilators during surgery. If a balloon is used for dilation, the balloon is inflated to the appropriate pressure for full dilation, and the sheath is placed into the kidney under direct ureteroscopic visualization. Alternatively, fluoroscopy could be used to position the sheath in a conventional manner or using a reduced fluoroscopic technique.

With the correct position of the sheath confirmed ureteroscopically, the procedure to remove one or more stones from the kidney 810 may be performed in a conventional fashion. In embodiments, flexible and rigid nephroscopy accompanied by use of ultrasound, laser, and/or basketing are used to remove the stone fragments. At the conclusion of the procedure, the kidney 810 is evaluated by flexible nephroscopy and ureteroscopy to confirm the absence of residual fragments. Intra operative ultrasound can also be used to look for residual stones.

After the removal of all stones, a single pulse of conventional fluoroscopy is used to ensure complete fragment removal. This step is omitted if the surgeon 803 is sure there are no residual fragments following endoscopic renal mapping. Alternatively, renal ultrasound could be used to look for residual fragments.

If a tubeless technique is desired, the surgeon 803 removes all the tubes at the conclusion of the procedure. Alternatively, the surgeon places an 8 or 10 Fr nephrostomy, or a 16, 18, or 22 Fr council-tipped catheter with a 5 Fr re-entry catheter inside the patient's 802 renal tract to allow for renal drainage and reentry at a later time if desired. These tubes are placed entirely without image guidance using direct vision by the ureteroscope or with minimal use of single pulse fluoroscopy. In another embodiment, the ureteral catheter is placed into the kidney 810 from above while monitoring the position of a proximal end of the catheter using a flexible nephroscope placed through the percutaneous access site.

In some embodiments, a ureteral stent (e.g., a multi-length stent having a length ranging from 22 cms to 32 cm and/or a diameter of approximately 6 Fr) is passed over a guidewire that was placed into the bladder using an angle tipped guidewire and a 4 Fr glide catheter. In another configuration, the 0.038 guidewire is used to insert the stent. In an embodiment, the length of the stent is calculated using a novel technique determining the ureteral length using the Pythagorean Theorem where ureter length is calculated by measuring the known coronal ureter length, left to right length, and anterior/posterior length. Alternatively, the length is estimated by counting the number of axial slices on a CT scan and multiplying by the slice reconstruction and adding 20%. In this technique, the fixed length stent is placed into the ureter from above and the stent is advanced until the markings showing the location for the UPJ are identified. The distal stent coil in the bladder is confirmed when the ureteroscope is pulled down into the bladder.

In an embodiment, an end-hole catheter is placed cystoscopically into the ureter and used to inject diluted contrast into the collecting system of the kidney ranging from 1-99% dilution depending upon the desired density of the contrast. The desired calyx is selected using fluoroscopy and any of the previously described techniques mentioned in the preceding description could be used for establishing access into the kidney. For example, in an embodiment, the C-arm 801 is rotated laterally between 20 and 30 degrees. The C-arm 801, sticker 190, and desired calyx are aligned, and the laser guide 806 is placed in the center of the needle hub 818 and used to insert the needle 820 in a steady controlled fashion. Using this technique, the surgeon can use his hands with no concern of radiation exposure since the laser guide 806 is used to direct the needle 820. Aspiration of fluid or air is used to confirm appropriate positioning in the calyx. Thereafter, a lubricious wire is fed down the ureter using minimal use of low-dose pulsed or conventional fluoroscopy.

In an embodiment, an ultrasound machine is used to select percutaneously the appropriate desired posterior calyx for access. The laser guide 806 is positioned in line with the access of the ultrasound guide. Alternatively, a separate laser guide is lined up with the axis of the ultrasound guide for insertion of the probe.

In an embodiment, a laser guide 806 is placed on a CT scanner or a CT fluoroscopy machine and the axis of the needle tract is positioned in line with the laser guide 806 as directed by the CT scanner. In another embodiment, the laser guide 806 is placed on a CT scanner and a special non-ferromagnetic needle is used for placement using CT fluoroscopy.

At various points of the procedure, fluoroscopy is performed either with a single pulse or a pulse rate of one pulse per second to visualize the tip of the ureteroscope, needle 820, and/or the guidewire. This pulse rate is lower than the conventional pulse rate, which ranges from 25 to 30 pulses per second. The method of the present specification enables a surgeon to reduce the fluoroscopy time from an average of approximately 6 to 7 minutes per procedure to less than about one minute per procedure. In certain aspects, the total fluoroscopy time is less than or equal to ten seconds, less than or equal to three seconds, or less than or equal to 1 second, thus reducing the risk of cancer for the patient, surgeon and staff by reducing the radiation exposure.

Needle

FIGS. 3-4 illustrate an exemplary embodiment of a needle assembly 30 configured for use with the methods described above. In some embodiments, a needle 32 is manufactured using a biocompatible material. In one embodiment, the needle 32 is made from 304 stainless steel. In embodiments, the needle 32 has sufficient column strength/rigidity to resist buckling/collapsing under an axially compressive load applied during a procedure. In embodiments, the needle has sufficient hardness to resist deformation/dimpling during handling and a procedure. The Rockwell hardness test determines the hardness of any material by measuring the depth of penetration of an indenter under a large load compared to the depth of penetration by a smaller preload. Different scales denoted by a single letter (A, B, C, D) refer to different loads of indenters. The 304 stainless steel needle has a hardness range between 70 to 180 Rockwell B. In some embodiments, higher hardness is obtained by cold working. In embodiments, the needle 32 has an ultimate strength between 495 and 550 Megapascal (MPa), which is approximately 72 to 80 kilopound per square inch (ksi). In embodiments, the needle's 32 modulus of elasticity is between 195 and 200 Gigapascal (GPa), which is approximately 28,300 to 29,000 ksi.

The needle 32 defines a lumen through which a stylet 38 optionally extends. In embodiments, the stylet 38 has a length equal to the length of the needle 32 plus an additional 5 mm to 5 cm, depending on the depth of a needle hub. In some embodiments, the lumen has a smooth tapered inner surface so that the stylet 38 seamlessly mates with the needle 32. The smooth tapered inner surface enables ease of replacing the stylet 38. The stylet 38 comprises a sharpened distal end to facilitate percutaneous access. The needle 32 comprises a blunt distal tip 36 to avoid inadvertent injury after removal of the stylet 38. In some embodiments, a distal tip of the needle 36 is sharpened. In some embodiments, the distal tip 36 of needle is shaped like a sharpened pencil tip to prevent migration off the trajectory. In different embodiments, the tip 36 is shaped like a pyramid, is a standard tapered tip which can be positioned to direct the needle 32 in the desired direction, or any other shape.

During a side-by-side evaluation of tissue biopsy needles having a Bevel Tip (BT) design, a Diamond Tip (DT) design, and a Conical Tip (CT) design, in biological tissue phantom (chicken breast, pork loin, and bovine liver) and simulated tissue phantom (gelatin, poly vinyl chloride (PVC)) mediums), it was observed that needle insertion (penetration into the medium) force was the least for the BT design, followed by the DT design. The CT design exhibited the highest needle insertion force of the three designs. Further, it was observed that needle deflection was the least for the DT needle upon penetration in the phantom mediums. Therefore, in some embodiments, the needle tip 36 is of either a diamond or bevel design. In embodiments, a length of the needle tip 36 with either a diamond or bevel design ranges from 0.1 mm to 2 cm from the tip. In embodiments, the tip configuration/design is selected to allow the surgeon to aim the needle with accuracy. In an embodiment, when the tip 36 has a bevel design, the bevel angle is between 20 degrees and 25 degrees, and the bevel length is between 0.20 millimeters (mm) to 0.25 mm. In some embodiments where the tip 36 has a diamond design, the tip angle is between 10 degrees and 15 degrees on each side, and the tip length is between 0.20 mm and 0.30 mm.

Optionally, the tip 36 of the needle 32 and/or stylet 38 is etched to create a prominent acoustic signal on ultrasound. In one embodiment, etching or texturing a needle tip surface (creating a diffused, coarse surface) increases echogenic properties under ultrasound imaging, and aids in needle tip visualization under ultrasound guidance. In other embodiments, dimpling, scoring, roughening, and creating a serrated surface on the needle tip also aids in needle tip visualization under ultrasound guidance. In some embodiments, at least a portion of the needle 32 proximal to the tip 36 comprises a square shape to increase the acoustic prominence of the needle (not shown). In an embodiment, approximately 1 centimeter (cm) length of the tip 36 of the needle 32 is echogenic in order to provide visibility under ultrasound. In some embodiments, the length of 1 cm may provide a minimum threshold of the distal tip portion 36 to confirm visibility of the needle 32 during an ultrasound-guided procedure. In some embodiments, a length in the range of 1 cm to 2 cm is provided with echogenic treatment. In an embodiment, the tip 36 of the needle 32 comprises a polymeric coating wherein the coating is configured to enhance echogenicity. In another embodiment, high purity alumina (Al2O3) powder dispersed in a matrix epoxy resin (a thermosetting polymer) is deposited on a metallic surface of the needle tip 36 using a spin coating process for increasing the visibility under ultrasound guidance.

Figure 29A:
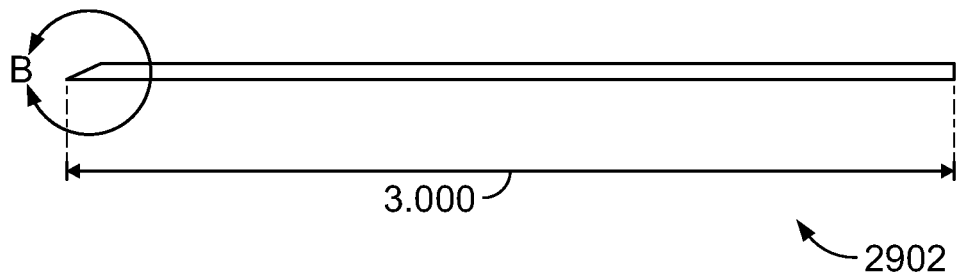
FIG. 29A illustrates a cross-sectional view of a needle, in accordance with some embodiments of the present specification.
Figure 29B:
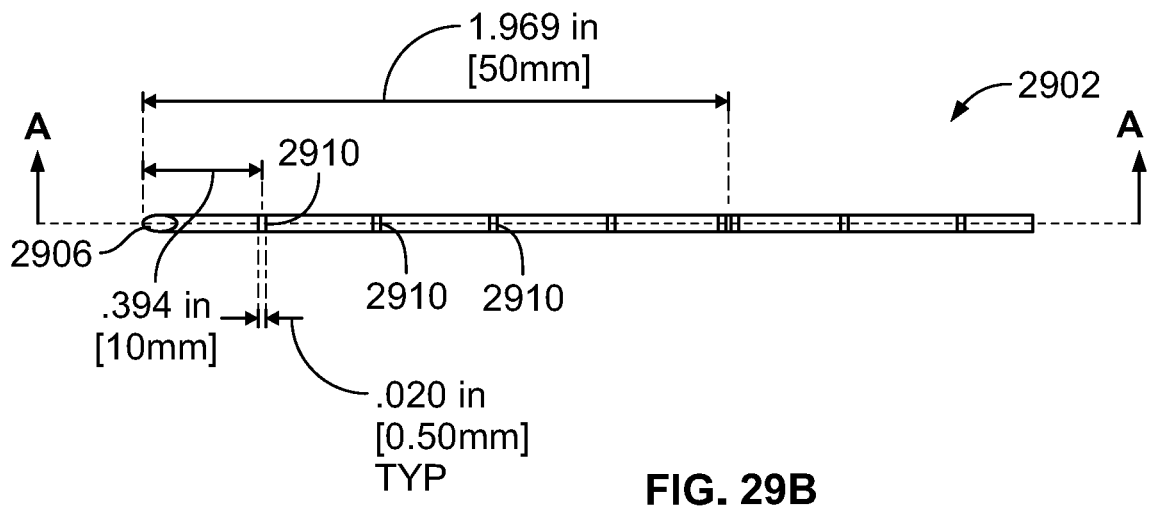
FIG. 29B illustrates a side view of the needle of FIG. 29A, in accordance with some embodiments of the present specification.
Figure 29C:
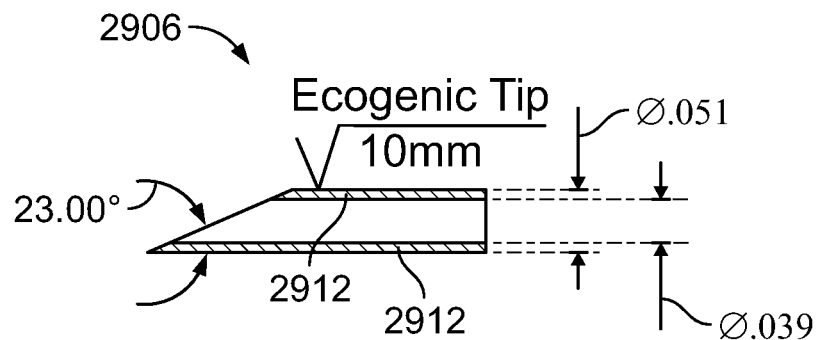
FIG. 29C illustrates a cross-sectional view of the tip of needle of FIG. 29A, showing the echogenic-treated portions near the tip, in accordance with some embodiments of the present specification.
Figure 29D:
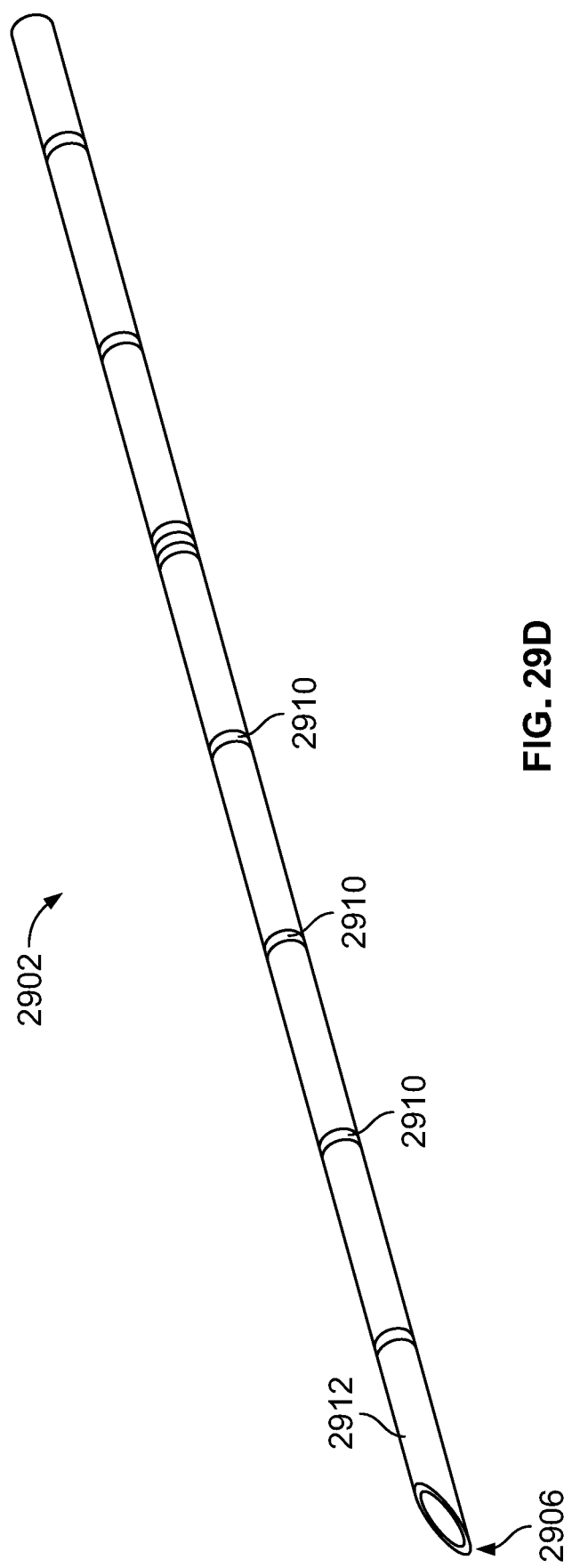
FIG. 29D illustrates a three-dimensional view of the needle of FIG. 29A, in accordance with some embodiments of the present specification.

Referring to FIG. 29A, a cross-sectional view of a needle 2902 is illustrated. In various embodiments, the needle has a length ranging from 2.50 to 3.50 inches. In one embodiment, the length of the needle 2902 is approximately 3 inches. In another embodiment, the length of the needle 2902 is approximately 3.43 inches. FIG. 29B illustrates a side view of the needle 2902. In one embodiment, approximately a length of approximately 1 cm from a tip 2906 of the needle 2902 is echogenic. In various embodiments, the length of the echogenic portion varies. In one embodiment, the entire needle is echogenic. Additionally, color marks 2910, which comprise colored strips of approximately 0.5 mm thickness, are marked on the circumference of the needle 2902 at regular intervals. In an embodiment, the marks 2910 are provided at a distance of 1 cm across the complete length of the needle 2902. In some embodiments, unique marks are additionally provided at regular intervals of 5 cm, or any other distance. The marks help surgeons to know how deep the needle 2902 is. FIG. 29C illustrates a cross-sectional view of the tip 2906 of needle 2902, showing the echogenic-treated portions 2912 near tip 2906. In one embodiment, the diameter of the echogenic-treated portion near the tip 2906 is approximately 0.051 mm over and around the circumference of the needle 2902. In one embodiment, the diameter of the remaining portion of the needle 2902 is approximately 0.039 mm. In another embodiment, the diameter of the remaining portion of the needle 2902 is approximately 0.035 mm. In one embodiment, the tip 2906 is shaped like a sharpened pencil tip to prevent migration off the trajectory. FIG. 29D illustrates a three-dimensional view of the needle 2902. The figure shows the echogenic portion 2912 near the tip 2906 and the marks 2910 along the length of the needle 2902.

Referring again to FIGS. 3 and 4, depending on the requirements of the procedure, in some embodiments, the length of the needle 32 ranges between 5 cm and 20 cm, e.g., 10 cm, 15 cm, or 20 cm. In some embodiments, the diameter of the needle 32 is 12 gauge and/or less than or equal to 25 gauge, such as approximately 18 gauge. The needle 32 comprises a lumen configured to allow the passage of a wire having a diameter ranging between 0.18 gauge and 0.38 gauge, such as approximately 0.25 gauge.

In some embodiments, the needle 32 is docked into a sheath to keep its tip 36 protected when the needle 32 is not in use. A user can slide the needle out of its sheath when ready for use. The protective sheath prevents the sharp tip 36 of the needle 32 from rupturing its sterile packaging material during storage and handling. In some embodiments, the sheath is manufactured from plastic, metal, or any other material suitable for storing a surgical needle. Dimensions of the sheath may depend on the dimension of the needle that it is configured to store. The sheath may be slightly larger to accommodate and hold the needle until the needle is pulled out by a user.

A proximal portion of the stylet 38 comprises a hub 34. In some embodiments, the needle 32 has a serrated portion at its proximal end that enables locking and unlocking of the hub 34. In some embodiments, a friction locking mechanism allows the hub 34 to remain coupled to the needle 32 when inserted during a surgical procedure. In embodiments, the hub 34 can be attached to different needles and therefore can be re-used for different procedures. In some embodiments, the hub 34 is made using a material that glows in the dark to make it easier to see with naked eyes in low light conditions. In one embodiment, a multiplane mirror that reflects light is used to achieve a glowing effect in low light. In other embodiments, a mirror configured like a disco ball is used, a piece of plastic that reflects light is used, a piece of reflecting metal is used, or any other shiny or reflective material is used to provide the glow-effect. Additionally, in one embodiment, the entire side of the needle hub 34 glows with the light. In another embodiment, a thin area on the side of the hub 34 glows to reflect the light. In another embodiment, there is a tiny disco ball in the center of the hub 34 and the laser light coming into the hub 34 hits the ball and is transmitted to multiple points on the clear sides of the needle hub 34. In another embodiment, the light is channeled to four points on the hub 34 separated by 90 degrees. In yet other embodiments, there are three points of illumination separated by 120 degrees, or two points of illumination separated by 180 degrees.

In an embodiment, the hub 34 is disc-shaped (as shown in FIG. 3). In one embodiment, the hub 34 has a diameter of approximately 1 inch. In other embodiments, the hub 34 is of a diameter that enables it to fit comfortably into a surgeon's hand and allow easy manipulation. As shown in FIG. 4, an upper surface of the hub 34 comprises a plurality of concentric rings 40 (e.g. two, three, or more) to help the surgeon accurately position a light guide source (e.g. laser). In some embodiments, at least a portion of the hub 34 (e.g. an outer portion of the hub 34 or the entire hub 34) is formed from a non-opaque material (e.g. transparent or translucent material). For example, an outer portion of the hub 34 is formed from a transparent material and a central portion of the hub 34 is formed from an opaque material to help center the laser. In various embodiments, the top portion or surface of the hub 34 is opaque, white, translucent white, clear white, black, green, or any other color that would make it easy to see the laser position or see the laser beam travel through the center of the hub 34. In some embodiments, the hub 34 has a diameter ranging between 5 mm to 5 cm. In an embodiment, the diameter of the hub 34 is approximately 2 cm.

In an embodiment, the distance between each ring 40 placed on the surface of the needle hub 34 is at least about 1 mm and/or less than or equal to about 10 mm, e.g., about 5 mm. The distance between each ring is substantially the same or may vary in embodiments.

As shown in FIG. 4, the hub 34 comprises a crosshatch 42 to help a user identify the central axis of the needle assembly 30. In some embodiments, the distance between the central axis C and an end of the crosshatch 42 ranges between 0.5 mm and 5.0 mm, or between 1.0 mm and 2.0 mm. In some embodiments, the distance between the central axis C and an end of the crosshatch 42 is one of 2 mm, and 1.5 mm.

In embodiments, the hub 34 is transparent or translucent and comprises an opaque channel (not shown). In an embodiment, the opaque channel is centrally disposed in the hub 34. An upper surface of the hub 34 comprises an opening that allows the passage of the light source through the opaque channel when the opaque channel is aligned with the light source. In one embodiment, the light source is a laser light source. In alternative embodiments, the light source comprises white light, or any other wavelength of visible light. In some embodiments, a width of the opaque channel ranges between 0.01 mm and 5 mm. In some embodiments, the opaque channel has a length ranging between 1 mm and 10 cm. The length to width ratio of the opaque channel is such that the angle that the needle 32 deviates from the axis of the light source and still produces the illumination of the glowing hub portion 34 of the needle 32 is very small, e.g. between 0.1 and 10 degrees, such as 2 degrees, and preferably less than 1 degree. In some embodiments, the opaque channel is narrow to increase the precision of the needle targeting. For example, in an embodiment, the channel is 1 mm wide and 15 mm long so that the light would not get through the channel unless the targeting was perfect.

In some embodiments, the opaque channel is lined with one or more reflectors. These reflectors are constructed from metal, glass, mirrors or any reflective material that can reflect light toward the light source when the light source is not aligned with the opaque channel so that no light enters the transparent or translucent portion of the hub 34. If the surgeon visualizes the feedback of the light reflected back out of the opaque channel, the surgeon would recognize that the orientation of the needle 32 is not correct. In some embodiments, a core of the channel is lined with a wound metal spring that reflects back the light when the light source is not correctly aligned as described above.

In some embodiments, the entire channel is translucent so that a laser light coming from the light source shines down through the needle hub 34 all the way to the skin so that one could see the laser through the needle 32 and at the tip 36 and know that the laser is aligned by looking at the skin. In some embodiments, the entire channels is transparent or clear. In alternative embodiments, there is a translucent/transparent circle in the hub 34. In some other embodiments, the laser light is diffracted a slight distance to make a circle visible on the skin such that one could keep lined up with the needle tip 36 inside the laser ring visible on the skin. In embodiments, the diffraction mechanism uses glass, plastic, Plexiglas, or any other transparent or translucent material that enables diffraction of the light. In some embodiments, the diffraction mechanism is configured so as to split the incoming beam slightly so that the needle tip is at the center of the circle created on the skin by the light. In some embodiments, the circle is created by a continuous line of light, or by dots of light. In addition, a laser source may be specially developed to produce light in a ring form which would shine through the opening in the needle hub 34 and be seen on the skin when correctly aligned.

In some embodiments, the needle assembly 30 does not include the stylet 38. In an embodiment, the distal end 36 of the needle 32 comprises a sharpened end, and the hub 34 described above is coupled to a proximal end of the needle 32.

Figure 9A:
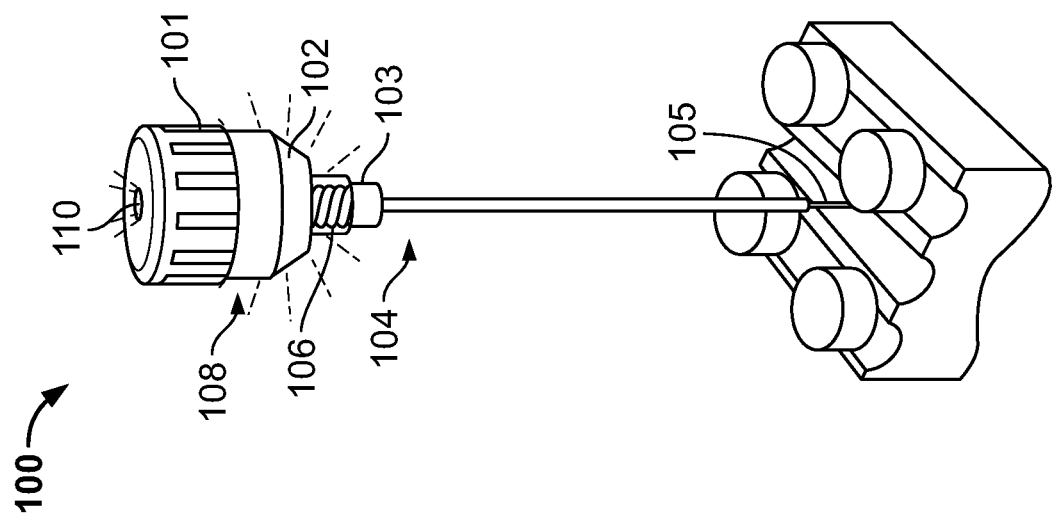
FIG. 9A illustrates the needle assembly shown in FIG. 9 in an illuminated configuration in accordance with an embodiment of the present specification.
Figure 9:
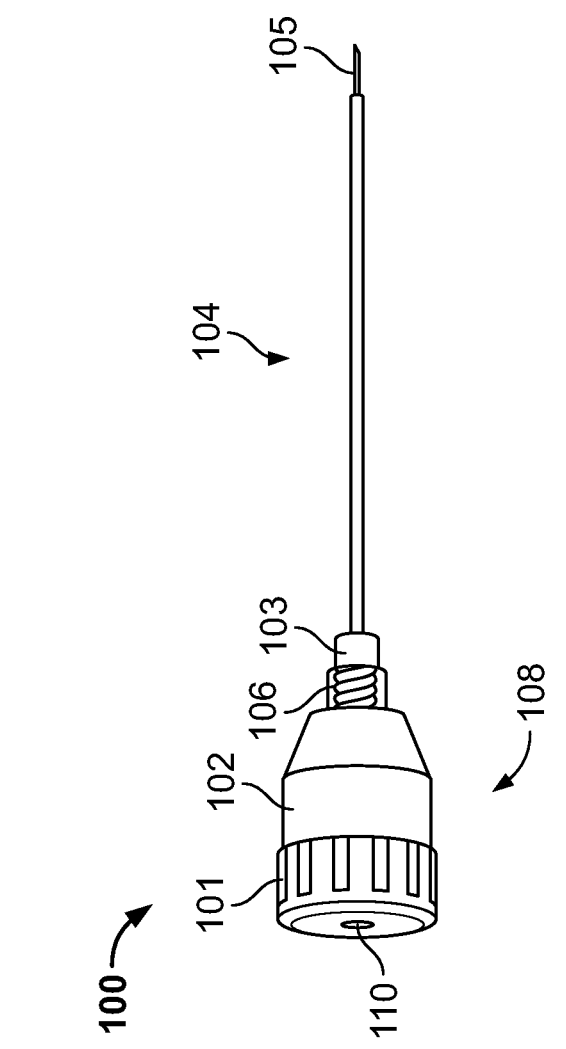
FIG. 9 illustrates a profile view of exemplary embodiment of a needle assembly that can be used with the methods described herein.

FIG. 9 and FIG. 9A illustrate an exemplary embodiment of a percutaneous access needle assembly 100 that can be used with the methods described above. As described above, a laser can facilitate insertion and removal of the needle assembly 100 at the correct position and correct angle. In embodiments, when the needle assembly 100 is positioned correctly, a main housing 102 of the needle assembly 100 lights up to indicate proper alignment with a light source (as shown in FIG. 9). In an embodiment, the light source, such as for example a laser light, exposed to the needle assembly 100 activates a chemical which creates a luminescent 'glow in the dark' phenomenon when targeting is accurate, or creates a chemical reaction that causes a certain change in color. In one embodiment, the chemical that creates the luminescent effect is coated inside the hub's surface. In embodiments, the chemical used for this effect may include, but is not limited to, fluoride. In an alternative embodiment, the needle activates a music box type action, which enables an audio indication, such as music, to be activated when the needle is aligned with the light source. In one embodiment, this is achieved by a sensor placed within the hub that communicates wirelessly with a speaker remote from the needle assembly. Use of the light source and needle assembly 100 to position the needle reduces the total amount of fluoroscopy time by at least 50%.

Figure 10:
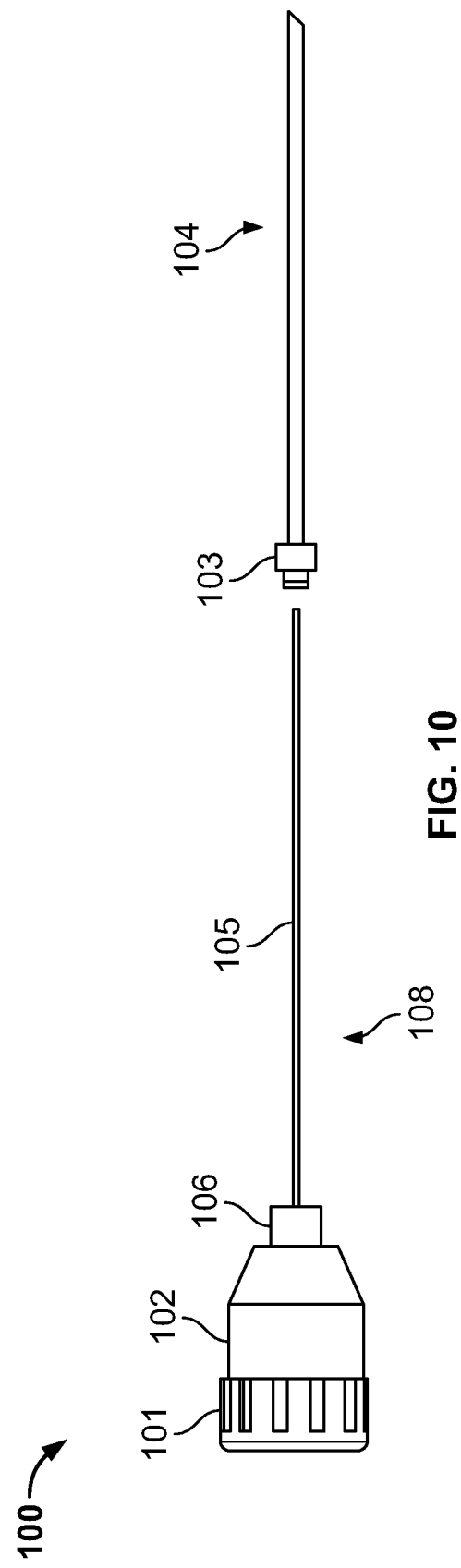
FIG. 10 illustrates a side view of the trocar needle and a cannula of the needle assembly shown in FIG. 9 in accordance with an embodiment of the present specification.
Figure 11:
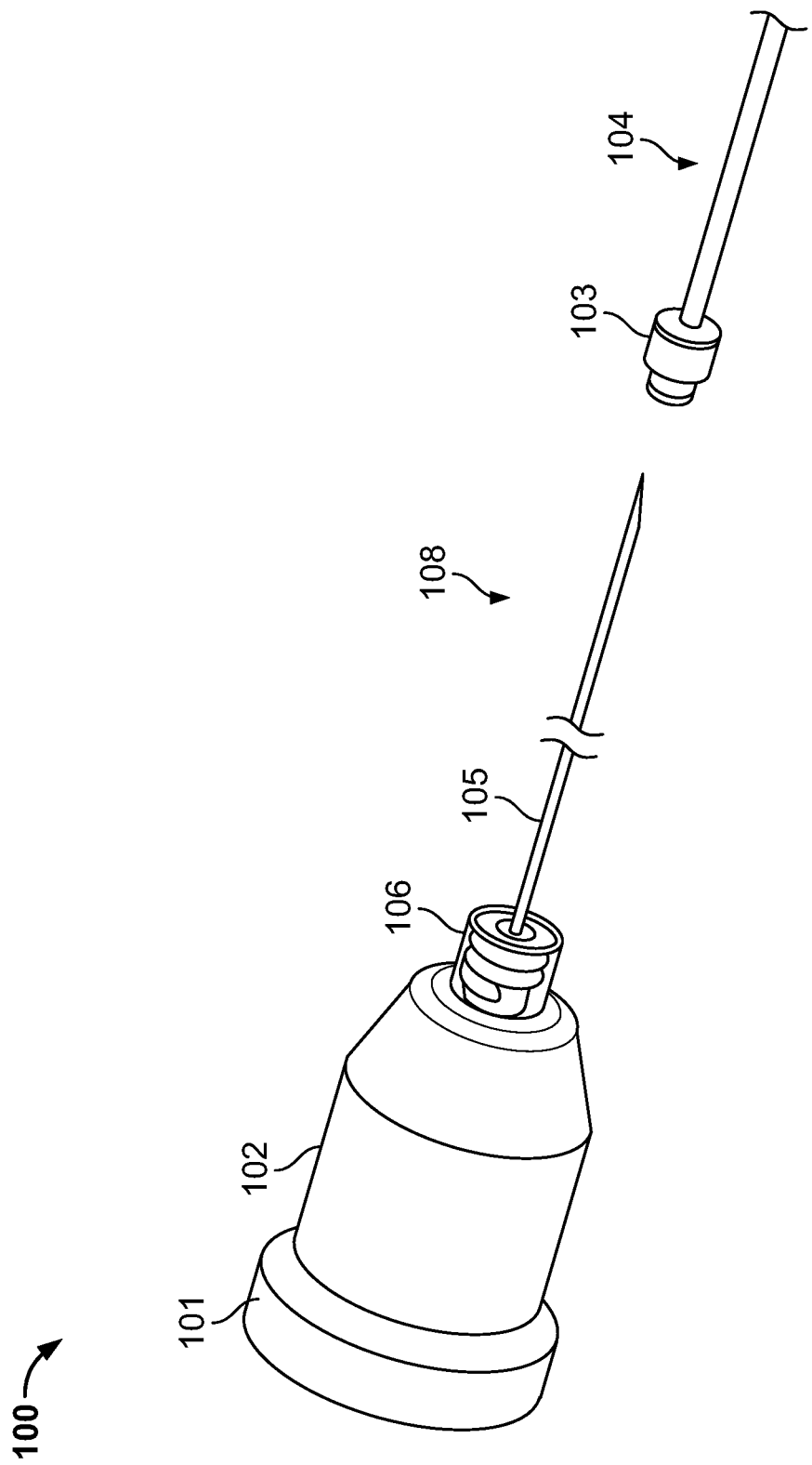
FIG. 11 illustrates a perspective view of the trocar needle and the cannula shown in FIG. 10 in accordance with an embodiment of the present specification.

As shown in FIG. 10 and FIG. 11, in embodiments, the needle access assembly 100 includes a trocar needle 108 axially movable through a cannula 104 (as shown in FIG. 18A-18C). In embodiments, the trocar needle 108 includes a main housing 102 and a needle 105 extending from the main housing 102. In some embodiments, the needle 105, which is sharpened to allow for easy insertion, can optionally be detached from the trocar needle 108. For example, the needle 105 can connect directly or indirectly to the main housing 102 using a snap fit, friction fit, screw fit, adhesive, or other suitable connection. Further, in embodiments, the trocar 108 optionally includes an engagement feature 106 (as shown in FIG. 10 and FIG. 11) that can removably engage a corresponding engagement feature 103 of the blunt hollow needle cannula 104. For example, in an embodiment, the needle assembly 100 includes a luer connector 106 at a distal end of the main body 102 which engages a corresponding luer connector positioned at a proximal end of the cannula 104. Other connections are also imaginable, such as screw fit, a friction fit, a snap fit, or otherwise.

As shown in FIG. 12, in an embodiment, the trocar 108 includes a cap 101 through which a laser or other light source is shined through an opening 110 to provide guidance for percutaneous access. In an embodiment, the cap 101 is opaque and comprises a narrow, centrally disposed opening 110 extending through the cap 101. In an embodiment, the opening 110 has a diameter that is less than a diameter of the main body 102 (e.g., less than about 50%, less than about 40%, less than about 30%, less than about 20%, less than about 10%, or values in between). In some embodiments, the opening 110 is optionally filled with a transparent material. In some embodiments, the cap 101 optionally includes a concentric circle pattern similar to the pattern described in connection with FIG. 4 to facilitate the positioning of the laser.

In embodiments, to facilitate visualization of the illuminated main body 102, the main body 102 includes a diameter of at least about 1 inch or at least about 2 inches, or preferably at least about 3 inches. In some embodiments, the main body 102 is constructed from an opaque material, and the user relies on alignment between the light source and opening 110 for visual indication of proper alignment. In some embodiments, the main body 102 is constructed from a transparent or translucent material so that users visualize the light source shining through the main body 102. Since the cap 101 is opaque, the main body 102 only illuminates if the laser is aligned with the opening 110. This ensures that that the main body 102 is not illuminated when the laser enters the main body 102 at an incorrect angle.

Figure 14A:
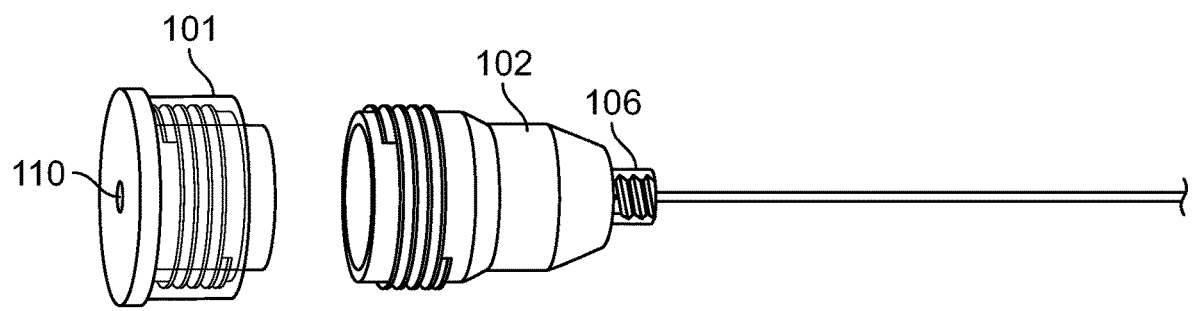
FIG. 14A illustrates another embodiment of a cap and a trocar needle.
Figure 14B:
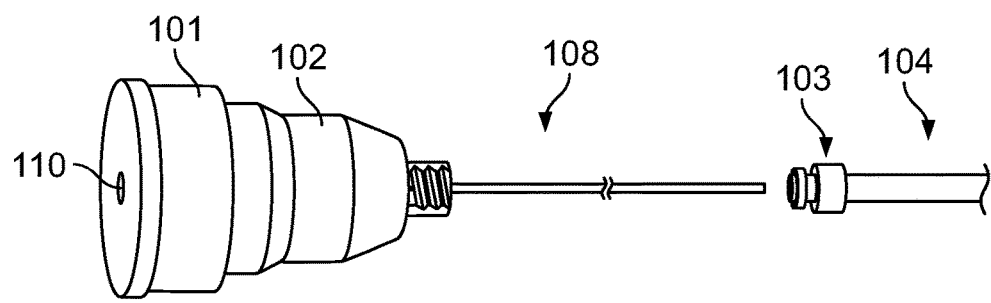
FIG. 14B illustrates a perspective view of a needle access assembly having the trocar needle shown in FIG. 14A and a cannula in accordance with an embodiment of the present specification.
Figure 14C:
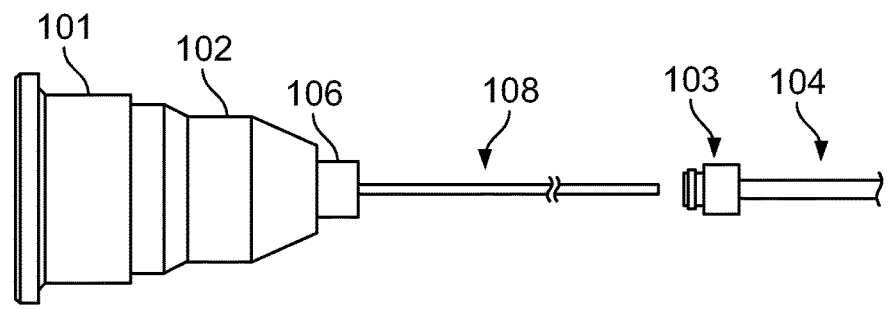
FIG. 14C illustrates a side view of the needle access assembly shown in FIG. 14B in accordance with an embodiment of the present specification.
Figure 15A:
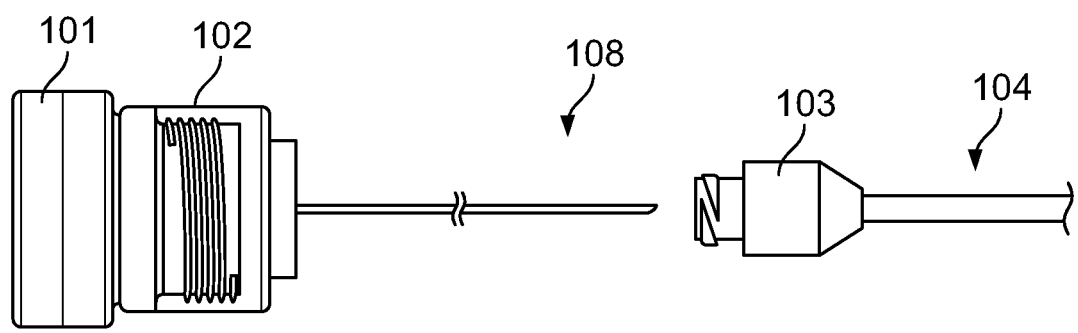
FIG. 15A illustrates a side view of another embodiment of a needle access assembly having a trocar needle and a cannula.
Figure 15B:
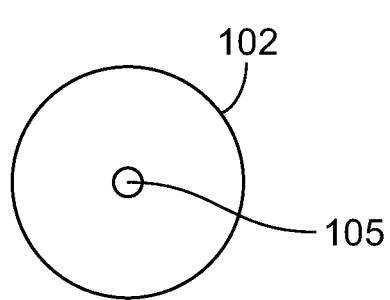
FIG. 15B illustrates a distal end view of the trocar needle shown in FIG. 15A in accordance with an embodiment of the present specification.
Figure 15C:
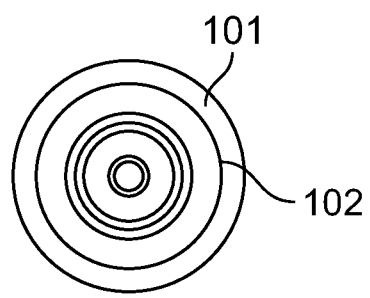
FIG. 15C illustrates a proximal end view of the trocar needle shown in FIG. 15A in accordance with an embodiment of the present specification.

In some embodiments, the cap 101 is removably engaged with the main body 102. For example, in an embodiment, the cap 101 threadably engages the main body 102 wherein the cap 101 fits into (as shown in FIG. 12) and/or surrounds (as shown in FIG. 14A-14C) the main body 102. In another embodiment, the cap 101 engages the main body 102 using a snap fit (not shown) wherein the cap 101 fits into and/or surrounds the main body 102. Alternatively, in some embodiments, as shown in FIGS. 15A-15D, the cap 101 and main body 102 are integrally formed.

As shown in FIG. 13A and FIG. 13B, the main body 102 of the trocar 108 can optionally include a light enhancement feature for propagating light. In some embodiments, as shown in FIG. 13A, a reflective plate or reflecting coating or otherwise reflective surface 111 is provided within an interior space of the main body 102. In some embodiments, as shown in FIG. 13B, a dome reflector 112 is positioned within the main housing 102. In some embodiments, two mirrors are provided that face each other. Of the two mirrors, a lower mirror may have a slightly convex surface and is positioned at the needle end of the hub, opposite the side of the hub where the light first comes in to the hub. The other mirror may be positioned on the inner surface of the top of the hub. An incoming light bounces back and forth between the top and bottom surfaces of the hub, thus illuminating the hub. In alternative embodiments, different types of light enhancement features are used. In one embodiment, one or more half and small disco balls are placed inside the cylindrical side surface of the main body 102, which reflects with the entire side and therefore lights up and is easier to see in the dark. Similar reflection characteristics are obtained by other embodiments, including, but not limited to, using an upside down cone covered with one or more reflective glasses, or four mirrors reflecting towards the opening 110. In various embodiments, the inner surface of the main body 102 is clear (transparent) plastic or opaque plastic to make it glow better with the reflective balls. Clear plastic may allow the light to pass outside the hub and might be easier to see. The opaque hub would glow but not allow the laser light to pass out the hub unfiltered and into the eye of the surgeon. In another embodiment, multiple reflective balls or small hemispheres are placed along the inner surface of the main body 102 in a polka dot pattern. Alternately, the needle could be held with four sites all on the same quadrant. When the needle is partly aligned, two sites would glow, but when perfectly aligned, all four sites would light up. In another embodiment, the internal surface of the main body 102 is a prism, made from glass, plastic, Plexiglas, or any other material, that changes the color of light to indicate correct alignment. In some embodiments, a fiber optic channel travels from the opening 110 to four different areas on the four sides of the needle to allow an area on the side to glow when the needle is lined up correctly. In embodiments, the fiber optic cable has a diameter ranging from 0.01 mm to 5 mm. The fiber optic cables may be positioned to four sides on the hub in each of the four quadrants. In an example, the cables could go to the base of the hub at 0 degrees, 90 degrees, 180 degrees and 270 degrees. In another embodiment, the fiber optic cables could go to 0 degrees, 120 degrees, and 240 degrees. In some embodiments, the fiber optic cables are positioned at the middle of the hub or the top of the hub or anywhere in between.

In some embodiments, the needle has four angled mirrors attached to it that direct the light to four different sides of the needle. In different embodiments, the mirrors are placed at any angle that aids directing the light to four different sides of the needle. In one embodiment, the mirrors are placed at 45 degrees. In some embodiments, the mirrors have dimensions in a range of 0.1 mm×0.1 mm to 10 mm×10 mm. In other embodiments, the mirrors are triangles, rectangles, circles, or any other shape. Glowing of all four sides of the needle along the external length of the needle indicates that the needle is correctly aligned.

In some embodiments, one or more sensors placed within the main body 102 sense the amount of light or laser light it is receiving, and activate a light when the received light reached a certain threshold. The activated light would indicate appropriate alignment.

Figure 17:
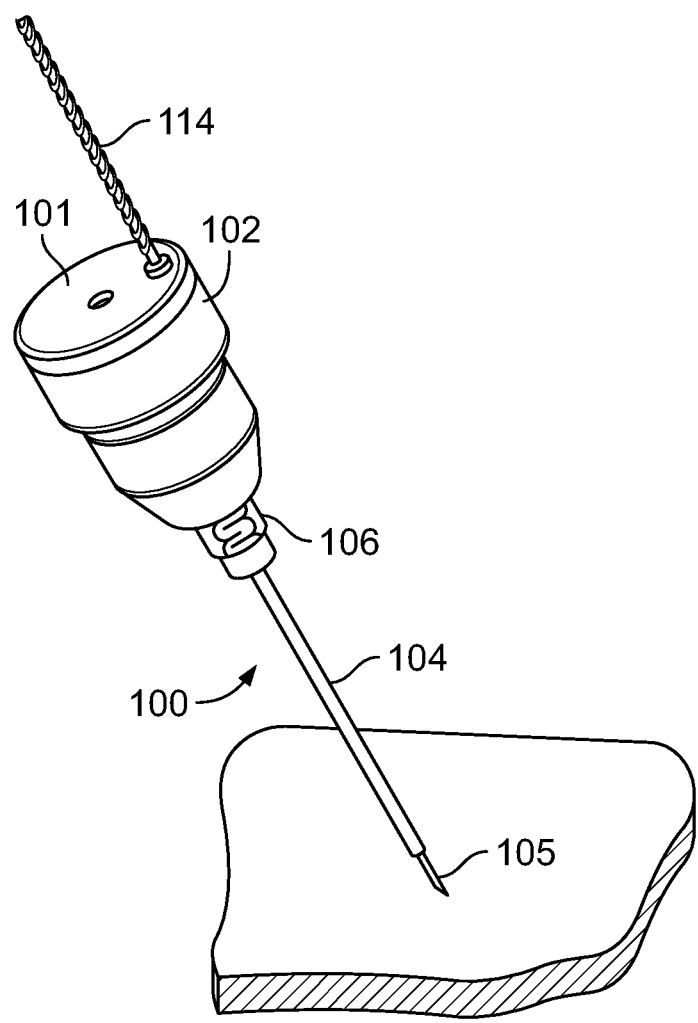
FIG. 17 illustrates a perspective view of the assembly shown in FIG. 16 indicating that the assembly is not properly aligned in accordance with an embodiment of the present specification.

As shown in FIG. 16, in an embodiment, when the needle access assembly 100 is aligned with the light source 114, the light enhancement feature propagate light 116 and there is clear visual indication of proper alignment. In contrast, as shown in FIG. 17, when the needle access assembly 100 is not properly aligned with the light source 114, little or no light is visible from the main housing 102.

Although not shown, in some embodiments, the needle access assembly 100 includes a camera to provide direct visualization during insertion. In some embodiments, the needle access assembly 100 includes sensors in a 3D array to provide real time data on 3D movement of the needle access assembly 100.

Training Model

Figure 5:
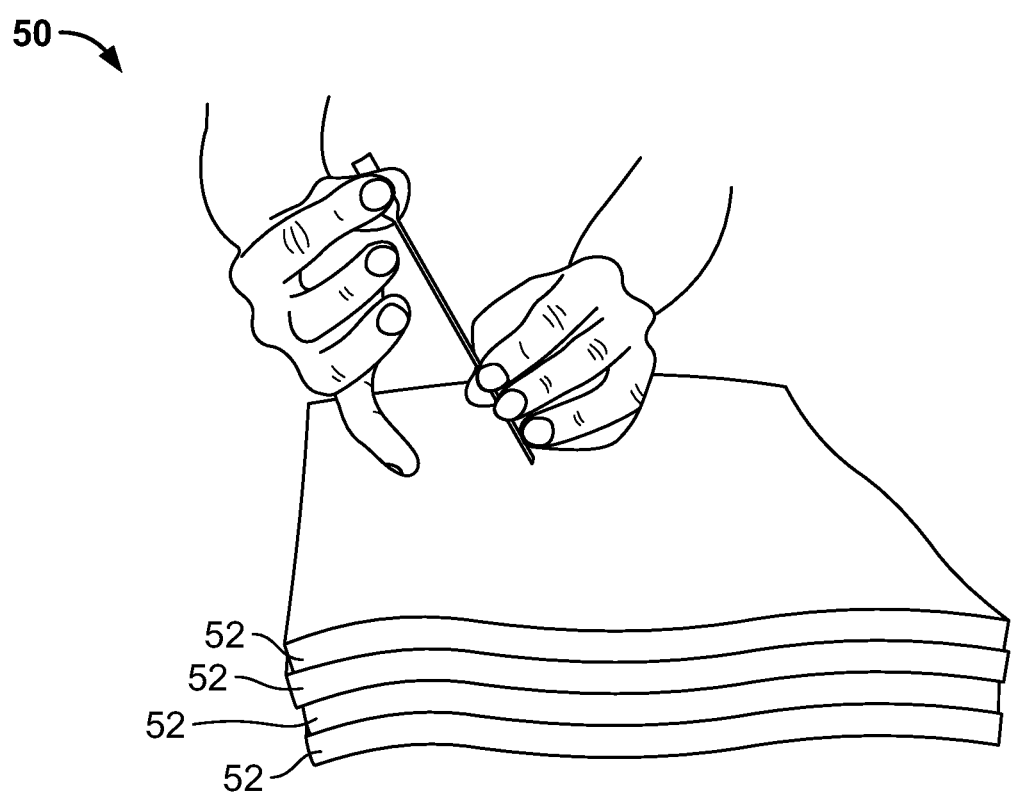
FIG. 5 illustrates a training model for percutaneous surgical access training in accordance with an embodiment of the present specification.
Figure 6:
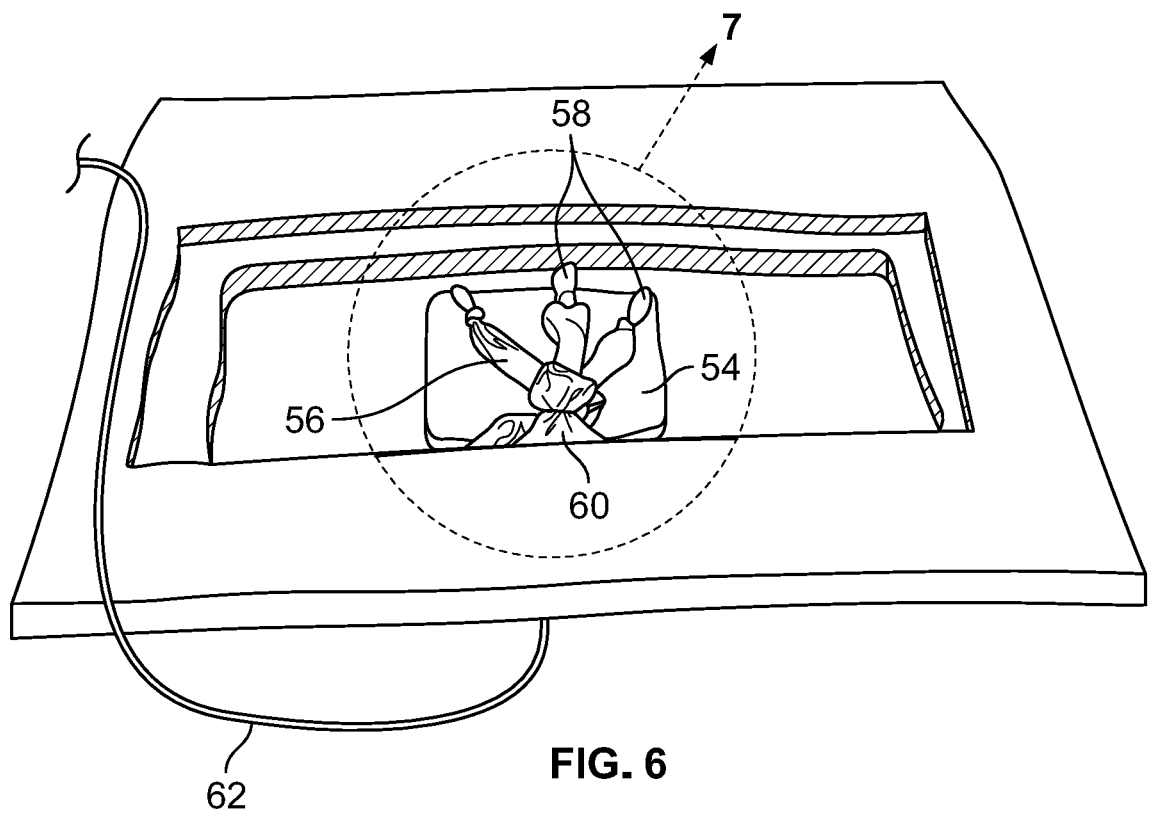
FIG. 6 illustrates a training model for percutaneous surgical access training in accordance with an embodiment of the present specification.
Figure 7:
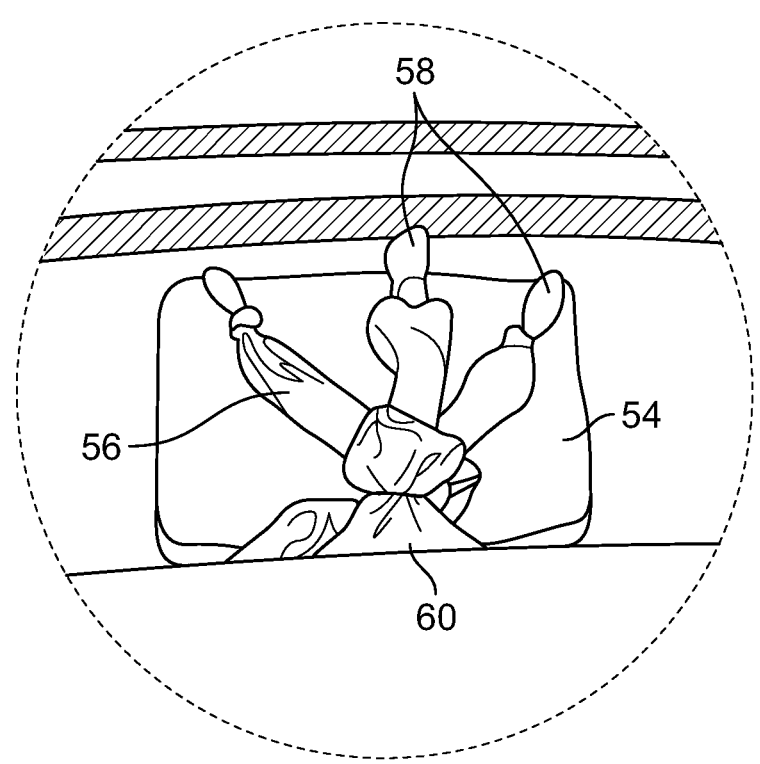
FIG. 7 illustrates a training model for percutaneous surgical access training in accordance with an embodiment of the present specification.

FIG. 5 through FIG. 7 illustrate a training model 50 for training users on obtaining percutaneous access using the above-described technique. In an embodiment, the model 50 includes one or more layers 52 designed to replicate the organs, muscle, fat, and skin. FIGS. 5-7 specifically illustrates a model 50 for a kidney collecting system, but similar materials can be used to construct a model for other areas of the body.

In an embodiment, the model 50 includes one or more layers designed to replicate the skin. In embodiments, the skin layers include, but are not limited to, carpet padding, plastic, or silicone. In an embodiment, deep muscles and perinephric fat are replicated using gelatin, silicone, or any polymer or substance that permits shaping into the desired shape. In an embodiment, the model collecting system 56 is replicated using latex or any type of glove. The fingers 58 are tied off to create the calices, and tape is applied to the innermost portions of the fingers to create the narrowing of the infundibula. The palm of the glove 60 is narrowed by tying or using tape to create a renal pelvis. In an embodiment, the palm of the glove 60 is connected to a penrose drain 62 to establish a ureter. The model kidney 54 is replicated by forming reniform shape from a gelatin, soft plastic, silicone, or other soft material. In embodiments, the kidney material is made of clear material to allow an observer to determine if the trainee had placed the needle into the appropriate calix by visual inspection from underneath a glass surface. In some embodiments, the model 50 includes a small camera on the inside to simulate the image provided by the ureteroscope and to allow the trainee to learn how the internal image may assist in correct placement of the needle.

In embodiments, the layers 52 are mounted on a surface constructed from a clear material, for example, Plexiglas. In embodiments, one or more holes are formed in the clear surface and each of the holes is configured to receive a bolt or other structure to secure and align each of the layers to the clear surface.

In embodiments, the model is configured to be positioned on a cut out portion of the fluoroscopy table, so that the observer can easily view if the needle has been placed into the appropriate calix by direct observation. In an embodiment, an open-ended catheter is used to create a contrast used for injection if the training is focused on learning the fluoroscopy guided laser DARRT technique.

Reduced Radiation Kit

In an embodiment, the present specification provides a reduced radiation kit comprising all or many of the instruments needed to perform a reduced radiation percutaneous procedure. In an embodiment, the reduced radiation kit comprises items selected by a user. The user may select the kit items based on the physiologic measurements of a patient, the technique to be practiced by a surgeon, or the resources available in the operating theatre.

In embodiments, the reduced radiation kit comprises the items packaged in a sterile manner ready for immediate use by the user. Having the items packed into a kit significantly reduces turnover times for operating room cases as the nurses do not need to open each item separately. Packaging items together is cheaper and simpler than opening up a separate package individually for each item. In addition, the reduced radiation kits reduce medical waste and the costs of disposal of this medical waste. In an embodiment, the user is required to attend a course where the individual items are demonstrated, allowing the user to design one or more of the kits by selecting items of choice.

The reduced radiation kit of the present specification is used for different procedures requiring percutaneous access to different structures, lumens, organs, and spaces in the body, such as, but not limited to, the kidneys. Although the kit embodiments discussed herein are described with respect to removing kidney stones in a percutaneous nephrolithotomy (PCNL) procedure, the kit may be used for other procedures such as, but not limited to, placing probes into the kidney to treat a renal cancer, placing access into an infected fluid collection for drainage of an abscess, placing tubes into any space to serve as a drain, (i.e., pleural space, peritoneal drain, cholecystectomy drain, bladder drain, lymphocele drain, pericardial space, and such other procedures).

In an embodiment, the present specification provides a method of using a reduced radiation kit for performing percutaneous surgery such as, but not limited to, percutaneous needle access of an internal organ (e.g., kidney). For example, the methods, devices, and kits disclosed herein can be used to perform a percutaneous nephrolithotomy. In an embodiment, the present specification provides a method of obtaining percutaneous needle access by using the reduced radiation kit. The method comprises selecting a patient's calyx for percutaneous access; positioning a flexible ureteroscope in the selected calyx; directing a laser guide at a desired needle-insertion angle and in line with a tip of the ureteroscope; aligning a needle with the laser guide and the ureteroscope tip; and inserting the needle into the selected calyx. In an embodiment, if required, fluoroscopy is applied for less than ten seconds. In embodiments, method and reduced radiation kit of the present specification allows incremental reduction in radiation exposure of 5-10%. In an embodiment, this reduction ranges from 5% to 99%.

The method of obtaining percutaneous needle access also comprises delivering an instrument from the reduced radiation kit to the selected calyx. The instrument is configured to facilitate the insertion of the needle into the selected calyx. In an embodiment, the instrument is identifiable under ultrasound. In an embodiment, the instrument is one of a balloon catheter and a basket catheter.

In various embodiments, the items included in the reduced radiation kit are designed to facilitate reduced radiation percutaneous access. For example, as depicted in FIGS. 19A-19C, the kit comprises one or more glow-in-the-dark stickers 190 or other indicators (e.g., a drawing marker, non-adhesive indicator, and the like). The sticker 190 comprises an adhesive on a back surface 192 of the sticker 190 and a display surface 194 opposite the back surface. The sticker 190 is configured to adhere to the skin of a patient. The display surface 194 of the sticker 190 is configured to enhance visualization in low light. In an embodiment, sticker 190 is used to identify the location of a patient's kidney. In an embodiment, the kit comprises a sticker 190 to identify the location of the bladder or another organ of the patient. Once the kidney is localized, one sticker may be placed at the location of the kidney and one sticker may be placed at the location of the bladder. In an embodiment, stickers 190 allow a fluoroscopy technician to identify the location of each area in the patient's body to save the radiation exposure usually required to localize a C-arm head being used to carry out the percutaneous access procedure. A laser pointer on the head of an image intensifier of the C-arm is used to target placement of the sticker 190. For example, after using the C-arm to generate an X-ray image and identifying the target location based on the image, a surgeon can mark the target using the sticker 190. The surgeon can direct the laser guide at the desired target based on the X-rays or other imaging techniques like ultrasound.

In an embodiment, sticker 190 comprises one or more marks 196 configured to allow an X-ray technician to easily identify a location of a patient's kidney. The one or more marks 196 may be configured in the form of a target (e.g., concentric circles, or cross-hairs). The marks 196 may comprise metal or other types of circles or rings shaped like a target to facilitate correct positioning of the C-arm. Concentric rings may be held together on adjacent edges of each ring and have a 2 mm, 3 mm or 4 mm hole in the center to make determining the location for the needle deployment more easy to identify. The ring structure may have a handle to make it easier to place. In some embodiments, a sticky series of radio-opaque grids may be used in place of rings. The grids may comprise an adhesive on their back surface of the sticker and a display surface opposite the back surface, which would show up under fluoroscopy and allow the surgeon to determine the angle of entry into the kidney (or any other organ) using this sticky grid that was attached to the patient. In an embodiment, the mark 196 is coated with a glow-in-the-dark material to enhance visualization of the mark 196 in the dark. In an embodiment, all portions of the sticker 190 are made radiolucent except for some indicator that is dense such as a metal ring to allow easy visualization under fluoroscopy or metal crosshairs. In an embodiment, the sticker 190 comprises an opening 197 or recess 198 configured to allow a needle to penetrate the skin without penetrating the sticker 10. In an embodiment, sticker 190 is designed in the form of a ring, with the opening 197 being concentric with a surrounding portion of the sticker. The opening 197 may be off-center from the central portion of the sticker 190. In embodiments, the opening 197 may have a circular or non-circular shape.

In an embodiment, the surface of the sticker 190 comprises reflective material that, when properly configured, causes a laser beam to be reflected and to intensify when the laser is correctly aligned. In an embodiment, the sticker is made of a stainless steel material. Also, in an embodiment, the magnitude of laser reflection intensity is intensified by using batteries as an intensifying mechanism, along with ensuring precise alignment in order to provide a two-fold or four-fold increase in intensity.

The sticker 190 may be removed after positioning the C-arm to allow the needle to penetrate the skin without the needle penetrating through the sticker 190. In an embodiment, the sticker 190 comprises regions that are radiolucent. In another embodiment, the sticker 190 comprises circles that are radiodense to create a bulls-eye target when fluoroscopy is employed. In another embodiment, the sticker 190 is configured to have radiodense regions circumferentially surrounding radiolucent regions to create a target image when viewed under fluoroscopy. The glow-in-the-dark sticker and the mirrored sticker can be made radiolucent to allow X-ray beams to pass through the sticker 190 and thereby not interfere with visualization of the fluoroscopy image.

The reduced radiation kit described in the present specification comprises a needle 100 as illustrated in FIG. 10 in accordance with an embodiment of the present specification.

In an embodiment, the kit comprises a reduced radiation device such as a laser Direct Alignment Reduced Radiation Technique (DARRT) needle. The needle 100 comprises any of the features of the needle described in U.S. Pat. No. 9,095,361, entitled "METHODS AND APPARATUSES FOR FLUORO-LESS OR NEAR FLUORO-LESS PERCUTANEOUS SURGERY ACCESS," filed on Jun. 3, 2014, which is incorporated herein in its entirety. In an embodiment, the needle 100 comprises a connector 106 (e.g., luer connector) to engage a cannula 104. After the needle-cannula assembly is inserted into a patient's skin, the connector 106 is disconnected and removed from the patient, while the cannula 104 maintains access into the patient. A user of the reduced radiation kit may select the needle 100 to be included in the kit.

An exemplary embodiment of a needle assembly that may be configured for use with the reduced radiation kit of the present specification is illustrated in FIG. 3 and FIG. 4 as described above.

In an embodiment, the reduced radiation kit comprises a plurality of different needles of different lengths and gauges. In an embodiment, the kit comprises at least a 10 cm needle, a 15 cm needle, a 20 cm needle, or combinations thereof. In an embodiment, the kit comprises needles having diameters ranging from 18 gauge to 21 gauge for use in obtaining access for percutaneous kidney stone surgery and other such applications. In other embodiments, the kit comprises needles ranging from 1 cm to 40 cm in length and having diameters ranging from 14 gauge to 27 gauge, thereby allowing the kit to be used to access a variety of organs, structures, and sites in a patient's body.

In various embodiments, enhancing ultrasonic profile of a surgical instrument such as a guide wire or a needle is achieved by enhancing the echogenicity of the instrument, thereby making the instrument visible under ultrasound guidance. In an embodiment, ultrasound core biopsy needles for aspiration of breast tissues, prostate tissues, liver tissues, and the like comprise a polymeric coating wherein the coating is configured to enhance or increase echogenicity. In another embodiment, high purity alumina ($Al_2O_3$) powder dispersed in a matrix epoxy resin (a thermosetting polymer) is deposited on a metallic surface of an instrument using a spin coating process for increasing the instrument's visibility under ultrasound guidance. In another embodiment, etching or texturing a needle tip surface (creating a diffused, coarse surface) increases echogenic properties under ultrasound imaging, and aids in needle tip visualization under ultrasound guidance. In other embodiments, dimpling, scoring, roughening, and creating a serrated surface on the needle tip also aids in needle tip visualization under ultrasound guidance.

In various embodiments, techniques such as, but not limited to dip coating, spin coating, echogenic texturing, creating a roughened/diffused surface (via micro blasting, bead blasting), scoring, forming/bending, creating a pattern-embossed section, are used for increasing the ultrasonic profiles during an ultrasound-guided procedure of the guidewires and needles included in the reduced radiation kit. A roughened or diffused surface results in higher echogenicity because such a surface typically has many micro peaks and valleys, which, in turn, assist in increasing the surface's visibility during an ultra sound-guided procedure. Polymeric coating (dip coating or spin coating) enhances echogenicity of the coated surface (needles or guide wires) since such treatment with the appropriate coating material/compound creates a surface that is compatible with, and visible under ultrasound guidance at a molecular level. Collectively, such features which cause a surface to have an increased roughness relative to the remainder of the needle surface may be considered ultrasonic-profile-enhancing features.

Referring to FIGS. 20A, 20B and 20C, the kit comprises a plurality of guidewires 2000 with enhanced ultrasonic profiles. As is known, a guidewire is a thin, usually flexible wire that can be inserted into a confines or tortuous space to act as a guide for subsequent insertion of a stiffer or bulkier instrument. A guidewire may be used for entering obstructed vessels or channels in a human body, or may be used to assist in inserting, positioning and moving a catheter. Guidewires vary in size, length, stiffness, composition and shape of the tip. Various types of guidewires such as, but not limited to stiff wires, super stiff wires, wire comprising floppy portions/tips, wires coated for gliding smoothly, and wires having malleable tips are available and may be selected based on their application in a desired medical procedure.

Guidewires having a rounded cross section do not appear on ultrasound machines as the ultrasound waves go right past the rounded portions. However, guidewires having partial flat surfaces such as shown in FIG. 20A and 20C are detectable by using ultrasound technique, as ultrasound bounce of a flat edge and are detected. Hence, in various embodiments, any portion of a guidewire and/or a needle included in the reduced radiation kit may be flattened, in order to increase their ultrasonic profile, thereby making said guidewires/needles visible when using ultrasound machines.

In an embodiment, guidewire 2000 is a cylindrical wire having a circular cross-section as depicted in FIG. 20A. A guidewire 2000 comprises a distal end 2004, a proximal end 2005 and at least one flat surface 2002 in close proximity to the distal end 2004. The flat surface 2002 reflects the sound waves emanating from an ultrasonic transducer. The flat surface 2002 may be spaced away from the distal end 2004 by a distance ranging from 1 cm to 5 cm for allowing ultrasonic localization of the guidewire distal end 2004. In an embodiment, the length of the flat portion 2002 as shown in FIG. 20A is approximately 5 mm; while a portion 2003 that is flattened as shown in FIG. 20C does not exceed 10% of a total circumference of the guidewire. In an embodiment, guidewire 2000 has a circular transverse cross-section over at least part of, at least a majority of, or substantially the entire guidewire, as shown in FIG. 20B. Additionally or alternatively, the guidewire 2000 comprises an etching or a coating 2006, as shown in FIG. 20C that allows the guidewire 2000 to be easily seen under ultrasound, thereby facilitating ultrasound-guided placement, or placement at low mAs or kVp settings under fluoroscopy.

In an embodiment, the reduced radiation kit of the present specification may comprise a needle 100 (as shown in FIG. 10) having one or more features enhancing the ultrasonic profile of the needle 100. In an embodiment, similar to the guidewire 2000 described above, the needle 100 may comprise a flat surface or an etching or coating that allows the needle 100 to be easily seen under ultrasound, thereby facilitating ultra-sound guided placement of the needle 100, or enabling needle guidance at low mA or kVp settings under fluoroscopy. In an embodiment, length of a flat portion (not shown in FIG. 10) included in a needle 100 is approximately 5 mm; while the portion that is flattened does not exceed 10% of a total circumference of the needle. Also, in embodiments, the flat surface is spaced away from a distal tip of the needle 100 by a distance ranging from 1 cm to 5 cm for allowing ultrasonic localization of the needle tip.

In an embodiment, the guidewire 2000 or needle 100 can be detected using single pulse fluoroscopic images using the lowest mA and kVp that provides an acceptable picture using intentionally fixed and reduced fluoroscopy settings. In an embodiment, the guidewire 2000 is configured to be placed through the bore of a hollow needle 100. Additionally or alternatively, the guidewire 2000 is configured to be placed retrograde through a ureteroscope using ultrasound or fluoroscopic guidance. Referring to FIG. 20A, in order to facilitate placement with no image guidance, the guidewire 2000 comprises markings 2010 that help the surgeon determine the position of the guidewire 2000. In an embodiment, the guidewire 2000 comprises a first mark indicating a distance from a patient's kidney to the ureteral orifice. The guidewire 2000 may also comprise additional marks placed at regular intervals above and below the first mark enabling the surgeon to deduce the position of the wire with respect to the kidney. In an embodiment, the first mark is designed to be more prominent (e.g., wider, longer, differently colored) than the additional marks. Placement of the first mark may be based on standardized tables and physiologic measurements of each individual patient. In an embodiment, the standardized tables may be generated by measuring average distance of the kidney from the ureteral orifice for a predefined number of patients. The standardized tables may be correlated with other physiologic characteristics of a patient such as height, weight, sex, or a combination thereof.

Some reduced radiation procedures may require a dark or dim operating room. Accordingly, in an embodiment, the reduced radiation kit comprises a guidewire having marks 2010 that can be easily perceived in low light. For example, the marks may comprise a fluorescent material or include a portion that can be perceived by touch.

In an embodiment, the reduced radiation kit comprises a dual-lumen catheter for placement of a safety guidewire alongside a standard guidewire. As is known, a dual lumen catheter is a long, flexible medical device that consists of one hollow tube within another hollow tube, and enables two different actions to take place close together and with less tissue trauma. These actions could be the withdrawal of fluid or the insertion of fluid, air or small medical devices. These catheters can be used to drain blood, urine or unwanted liquid, such as from the lungs or abscesses. A double lumen catheter can be made from one of many flexible materials, such as silicone, latex, Teflon® or polyurethane. In an embodiment, the dual-lumen catheter included in the reduced radiation kit comprises a radio-opaque tip that can be easily visualized with much reduced current (mA) and voltage (kVp) settings on a fluoroscopy machine.

In an embodiment, the reduced radiation kit comprises an extra-stiff guidewire that may comprise a flexible or floppy region at one or both ends of the extra-stiff guidewire, with the flexible or floppy region(s) being more flexible (or less rigid) than an intermediate region. This is a standard component or can be designed as is known to those of skill in the art. Various medical procedures requiring a guidewires use both extra-stiff guidewires as well as standard guidewires. Usually, a soft/floppy guidewire is first inserted through a required body lumen. Then a catheter is positioned over the wire and safely placed in the body lumen. Next, the soft guidewire is removed and the stiff guidewire is threaded through the catheter, to act as a guide for using various medical instruments to perform a medical procedure. A soft guidewire cannot be used as a guide for the medical instruments, as it bends and takes the shape of the body lumen. Hence, the stiff portion of the guide wire provides pushability (due to its rigidity and column strength) while the flexible end(s) provide flexibility and maneuverability in an atraumatic way, minimizing the likelihood of organ puncture/perforation. In an embodiment, the guidewire comprises an angular tip that increases the steerability of the guide wire. In embodiments, a flexible region is placed within 3 to 5 cm from a distal end of the guidewire and the length of the flexible region ranges from 1 to 15 cm. In embodiments, a flexible region is placed within 1 to 2 cm from a proximal end (that is inserted into a body lumen) of the guidewire.

In an embodiment, the extra-stiff guidewire comprises a radio-dense core that allows visualization at extremely low radiation exposure. The extra-stiff guidewire can be configured to be detected at fixed, intentionally-reduced mA and kVp settings ranging from 1 to 8 pps. In an embodiment, the extra-stiff guidewire is configured to be detected at a mA setting ranging from approximately 1.5 mA to approximately 4 mA and at a kVp setting ranging from approximately 50 kVp to approximately 100 kVp. Depending on the size of a patient and on whether a small body part (e.g., finger) is being imaged with fluoroscopy, the extra-stiff guidewires may be detected at even lower mA and kVp settings. In an embodiment, the extra-stiff guidewire is wound with a coating that can be easily detected by ultrasound. Additionally or alternatively, the extra-stiff guidewire is etched with a substance that is easily detected by ultrasound. Additionally or alternatively, the extra-stiff guidewire is coated with a radio-dense coating that is easy to see under reduced fluoroscopy settings. In an embodiment, the extra-stiff guidewire comprises a standard guidewire and an angle-tipped guidewire with similar features. The angular tip increases the steerability of the guide wire, and minimizes trauma to a patient's organs.

In an embodiment, the reduced radiation kit comprises an ultrasound contrast material that is injected through an endhole catheter to help identify the location of the renal pelvis and calices without any radiation exposure. In embodiments, the contrast material comprises air bubbles, such as but not limited to microbubbles, trapped in a biologically safe coating to keep the bubbles in suspension. In an embodiment, bubbles are obtained by having a skilled person inject air into a kidney's collection system. The bubbles aid in increasing the echogenicity of the contrast material, and since, air bubbles tend to rise up, they aid with determining and conveying an orientation of the patient. Additionally or alternatively, the kit comprises a standard ultrasound contrast. In embodiments, the kit comprises an ultrasound contrast already approved for use for injecting into a collecting system.

Figure 21:
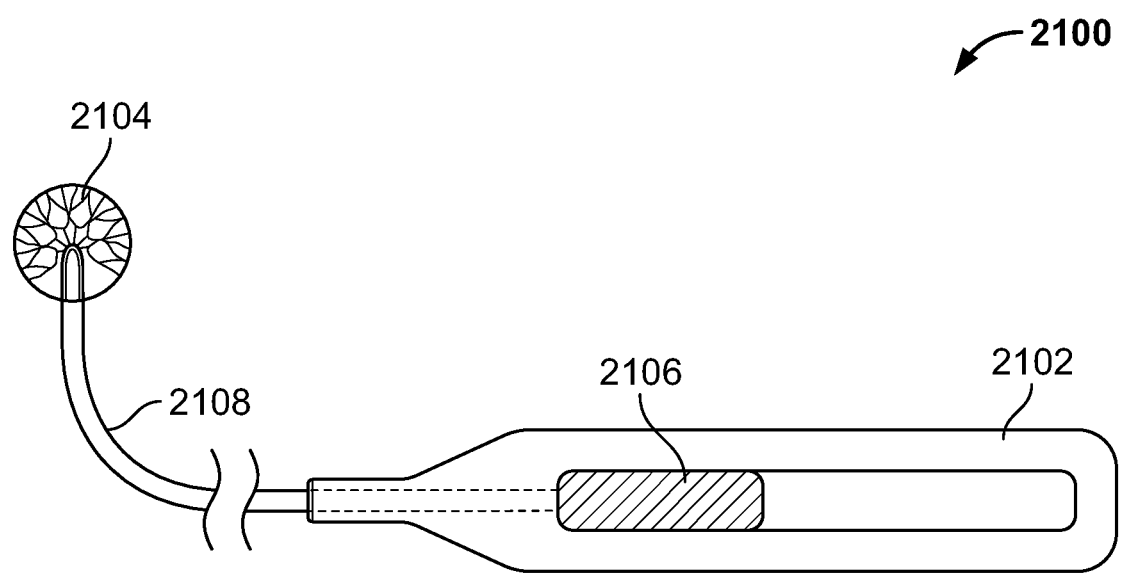
FIG. 21 illustrates an exemplary basket catheter provided in the reduced radiation kit, in accordance with an embodiment of the present specification.

Referring to FIG. 21, in an embodiment, the reduced radiation kit comprises a basket catheter 2100 (similar to the basket catheter shown in FIG. 2). The basket catheter 2100 comprises a handle 2102 at a proximal end and a basket 2104 at a distal end. The basket catheter 2100 comprises an actuation member 2106 configured to advance and retract the basket 2104 relative to an outer sheath 2108. The basket 2104 is in an open configuration, when advanced distally beyond the outer sheath 2108. The open configuration of the basket 2104 facilitates insertion of a guidewire into the basket 2104. The basket 2104 is retracted back into the outer sheath 2108 after insertion of the guidewire, thereby closing the open configuration of the basket 2104 and capturing the inserted guidewire.

In an embodiment, the basket catheter 2100 comprises a 2.2 Fr basket 2104 for snaring a small wire ureteroscopically and pulling the wire down into the ureter. In embodiments, the reduced radiation kit comprises a basket 2104 such as the 2.2 or 2.4 Fr N-circle basket. Additionally or alternatively, the reduced radiation kit comprises a basket catheter 2100 including any of the features disclosed in U.S. Pat. No.

9,095,361, entitled "METHODS AND APPARATUSES FOR FLUORO-LESS OR NEAR FLUORO-LESS PERCUTANEOUS SURGERY ACCESS," filed on Jun. 3, 2014, which is included herein in its entirety. In an embodiment, the basket catheter 2100 is used to capture a guidewire with an enhanced ultrasonic profile, such as the guidewire 2000 described with reference to FIGS. 20A-20C. In some aspects of the reduced radiation percutaneous method disclosed herein, the basket catheter 2100 is inserted into the patient and opened, making the basket 2104 easily seen under ultrasound. A needle 100 (as shown in FIG. 10) is then inserted into the center of the basket 2104 under ultrasound. In an embodiment, the needle 100 comprises one or more feature that enhances the ultrasonic profile of the needle 100, thereby facilitating placement of the needle 100 within the basket. A guidewire 2000 is then advanced through the needle 100 and into the basket 2104. The basket 2104 is then closed, thereby capturing the guidewire 2000.

Figure 22:
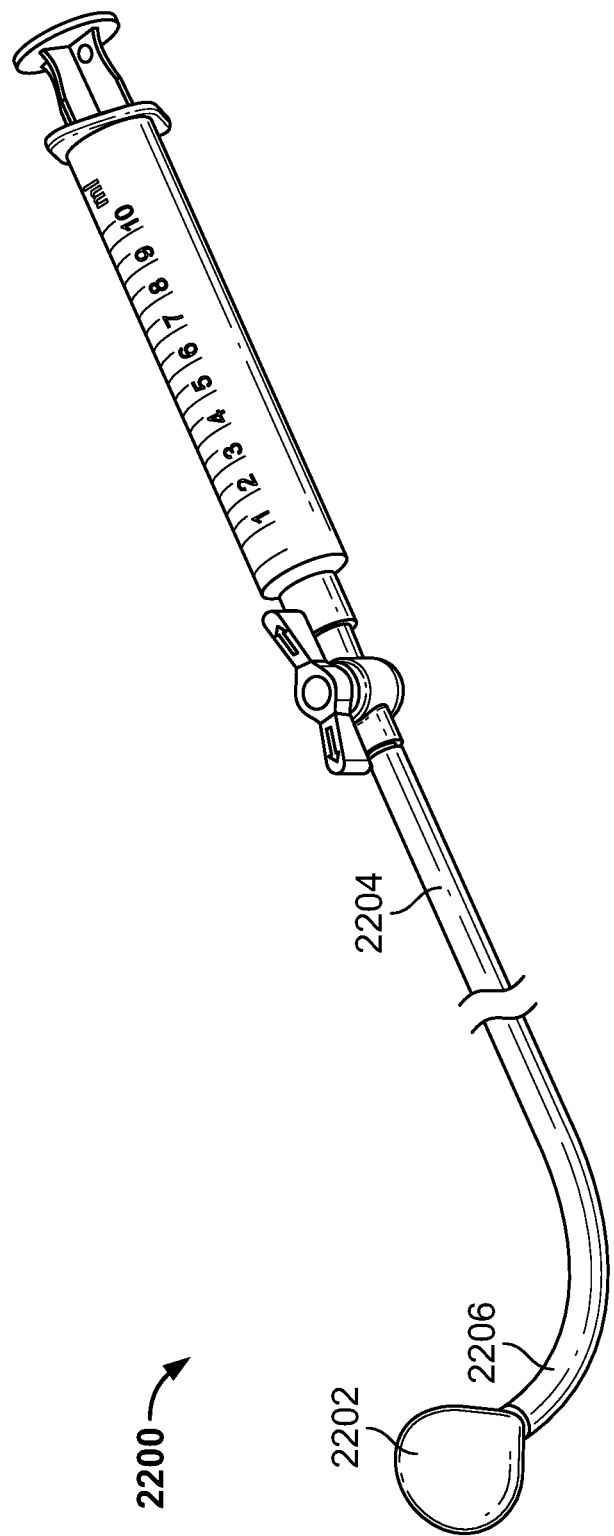
FIG. 22 illustrates an exemplary balloon catheter provided in the reduced radiation kit, in accordance with an embodiment of the present specification.

Referring to FIG. 22, in an embodiment, the reduced radiation kit comprises a balloon catheter 2200 (similar to the balloon catheter shown in FIG. 1). In an embodiment, the balloon catheter 2200 is a latex-free 22 Fr balloon catheter. In another embodiment, balloon catheter 2200 comprises a balloon 2202 having diameter ranging from 4 Fr to 24 Fr and made of materials such as, but not limited to latex, silicone, or a radiodense material, thereby facilitating visualization of the balloon 2202 under reduced radiation settings. In other embodiments, the diameter of the balloon catheter 2200 varies, depending on the body site being accessed. In an embodiment, the balloon catheter 2200 is configured to be placed over a guidewire. In an embodiment, the balloon catheter 2200 comprises marks (not shown in FIG. 22) along its shaft 2204 to facilitate placement of a distal end 2206 of the balloon catheter 2200 in the calyx of a patient. In some embodiments, the marks extend from a proximal end to a distal end of the shaft and are spaced at 1 cm distance from one another. Additionally or alternatively, the balloon catheter 2200 comprises a material that is acoustically dense to facilitate placement of the catheter in the patient's kidney using ultrasound.

In an embodiment, the reduced radiation kit comprises a nephrostomy tube having a diameter ranging from 6 to 10 French that is etched to allow placement of the tube under ultrasound guidance. This is a standard component or can be designed as is known to those of skill in the art. In another embodiment, the reduced radiation kit comprises a nephrostomy tube having a diameter ranging from 4 to 24 Fr for placement in a patient's kidney. Additionally or alternatively, the nephrostomy tube comprises a coating that allows it to be seen under ultrasound. In an embodiment, the nephrostomy tube comprises a tip that includes a radio-dense material, making the tip easily visualized under minimal radiation settings.

In an embodiment, the reduced radiation kit comprises a nephrostomy tube sheath having centimeter marks on the outside of the nephrostomy tube sheath, thereby facilitating placement of a corresponding nephrostomy tube at an appropriate depth. This is a standard component or can be designed as is known to those of skill in the art. In an embodiment, the nephrostomy tube sheath comprises a tip that includes a radio-dense material, allowing the internal tip of the sheath to be more easily seen under ultrasound guidance to allow placement of the nephrostomy tube at the appropriate depth.

In an embodiment, the reduced radiation kit comprises a balloon dilator that has radio-opaque marks along its side. The balloon dilator is configured for establishing a tract into a patient's kidney during PCNL or for dilating a patient's ureter during ureteroscopy. In an embodiment, a diameter of the balloon dilator used for dilating the ureter ranges from 12 to 18 Fr and that used for dilating the kidney tract ranges from to 16 to 34 Fr. The balloon catheter 2200 comprises a readily visible mark so that a surgeon can perceive the mark under ureteroscopy, thereby facilitating placement of the balloon catheter 2200 at the appropriate depth to achieve dilation of the kidney tract.

In an embodiment, the reduced radiation kit comprises a 6 Fr open-ended stent that has marks placed on its external surface. In an embodiment, the kit comprises an acoustically dense JJ ureteral stent that can easily be seen under ultrasound. Additionally and alternatively, the ends of the JJ stent comprise one or more radio-dense materials so that the stent tip can be localized with an adhesive marker placed over the kidney to allow the stent to be positioned with extremely low current (mA) and voltage (kVp) fluoroscopy settings (e.g., settings that enable visualization at fixed intentionally reduced radiation settings at one pulse per second pulsed fluoroscopy). In an embodiment, the stent comprises a mark at the probable location of the ureteral orifice, thereby simplifying placement of the stent with minimal radiation.

Additionally or alternatively, the kit comprises a 5 Fr endhole catheter. In an embodiment, the catheter and the stent described above are acoustically dense and visible under reduced fluoroscopy settings.

In an embodiment, the kit comprises a glide catheter configured to be advanced beyond impacted stones in a kidney during a PCNL procedure. A glide catheter (or "glidecath") provides the enhanced lubricity needed to facilitate smooth atraumatic passage through tortuous anatomy. In an embodiment, a standard glide catheter is modified to allow for facile insertion and placement of the glide catheter using reduced fluoroscopy and ultrasound.

In an embodiment, the kit comprises an advancer for advancing the stent. In an embodiment, the advancer comprises marks along its surface enabling the surgeon to know how far into a urethra the advancer has progressed, thereby allowing placement of a stent using external cues. For example, the distance from the external meatus to the position of the bladder neck is measured on a cystoscope at the start of a procedure. The cystoscope comprises marks to indicate the length of the urethra. Then the stent is placed from outside the urethra over the wire and the advancer used to advance the stent to the correct distance.

In various embodiments, users can tailor the reduced radiation kit based upon individual needs. For example, a user may select the kit items for allowing insertion of an 18 gauge needle followed by insertion of an angle-tipped lubricious wire. Alternatively, a user may select the kit items for insertion of a 19 to 21 gauge needle followed by a small 0.018 inch or 0.025 inch guidewire, which is subsequently upsized over a sheath to a size that can allow placement of a 0.038 inch wire once correct positioning of the needle is confirmed. As discussed above, these wires comprise features such as markings indicating how far the wire has progressed inside the patient.

In an embodiment, the reduced radiation kit of the present specification is used to perform a reduced radiation percutaneous needle access procedure (e.g., percutaneous nephrolithotomy) similar to the procedure described in FIG. 8A through FIG. 8D.

In some embodiments, a ureteral stent (e.g., a multi-length stent having a length ranging from 22 cm to 32 cm and/or a diameter of approximately 6 Fr) is passed over a guidewire 2000 that was placed into the bladder using an angle tipped guidewire 2000 and a 4 Fr glide catheter. In another configuration, the 0.038 guidewire is used to insert the stent. In an embodiment, the length of the stent is calculated using a novel technique determining the ureteral length using the Pythagorean Theorem where ureter length is calculated by measuring the known coronal ureter length, left to right length, and anterior/posterior length. Alternatively, the length is estimated by counting the number of axial slices on a CT scan and multiplying by the slice reconstruction and adding 20%. In this technique, the fixed length stent is placed into the ureter from above and the stent is advanced until the markings showing the location for the UPJ are identified. The distal stent coil in the bladder is confirmed when the ureteroscope is pulled down into the bladder.

In an embodiment, an end-hole catheter is placed cystoscopically into the ureter and used to inject diluted contrast into the collecting system of the kidney ranging from 1-99% dilution depending upon the desired density of the contrast. The desired calyx is selected using fluoroscopy and any of the previously described techniques mentioned in the preceding description could be used for establishing access into the kidney. For example, in an embodiment, the C-arm 801 is rotated laterally between 20 and 30 degrees. The C-arm 801, sticker 190, and desired calyx are aligned, and the laser guide 806 is placed in the center of the needle hub 818 and used to insert the needle 820 in a steady controlled fashion. Using this technique, the surgeon can use his hands with no concern of radiation exposure since the laser guide 806 is used to direct the needle 820. Aspiration of fluid or air is used to confirm appropriate positioning in the calyx. Thereafter, a lubricious wire is fed down the ureter using minimal use of low-dose pulsed or conventional fluoroscopy.

In an embodiment, an ultrasound machine is used to select percutaneously the appropriate desired posterior calyx for access. The laser guide 806 is positioned in line with the access of the ultrasound guide. Alternatively, a separate laser guide is lined up with the axis of the ultrasound guide for insertion of the probe.

In an embodiment, a laser guide 806 is placed on a CT scanner or a CT fluoroscopy machine and the axis of the needle tract is positioned in line with the laser guide 806 as directed by the CT scanner.

In another embodiment, the laser guide 806 is placed on a CT scanner and a special non-ferromagnetic needle is used for placement using CT fluoroscopy.

At various points of the procedure, fluoroscopy is performed either with a single pulse or a pulse rate of one pulse per second to visualize the tip of the ureteroscope, needle 820, and/or guidewire 2000. This pulse rate is lower than the conventional pulse rate, which ranges from 25 to 30 pulses per second. The method of the present specification enables a surgeon to reduce the fluoroscopy time from an average of approximately 6 to 7 minutes per procedure to less than about one minute per procedure. In certain aspects, the total fluoroscopy time is less than or equal to ten seconds, less than or equal to three seconds, or less than or equal to 1 second, thus reducing the risk of cancer for the patient, surgeon and staff by reducing the radiation exposure.

Figure 23:
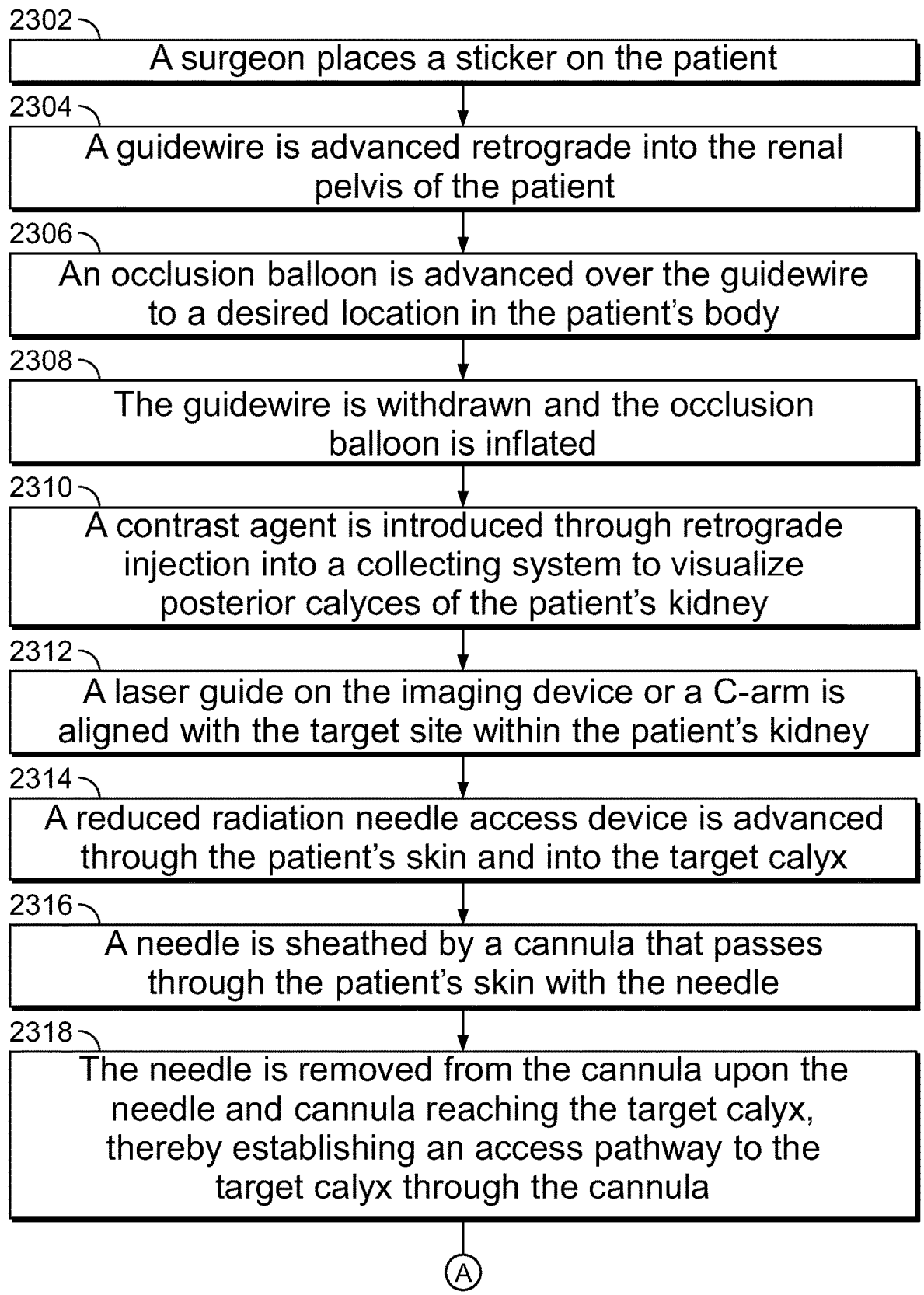
FIG. 23 is a flowchart illustrating an exemplary method of performing a reduced radiation percutaneous needle access procedure by using the reduced radiation kit, in accordance with an embodiment of the present specification.
Figure 23:
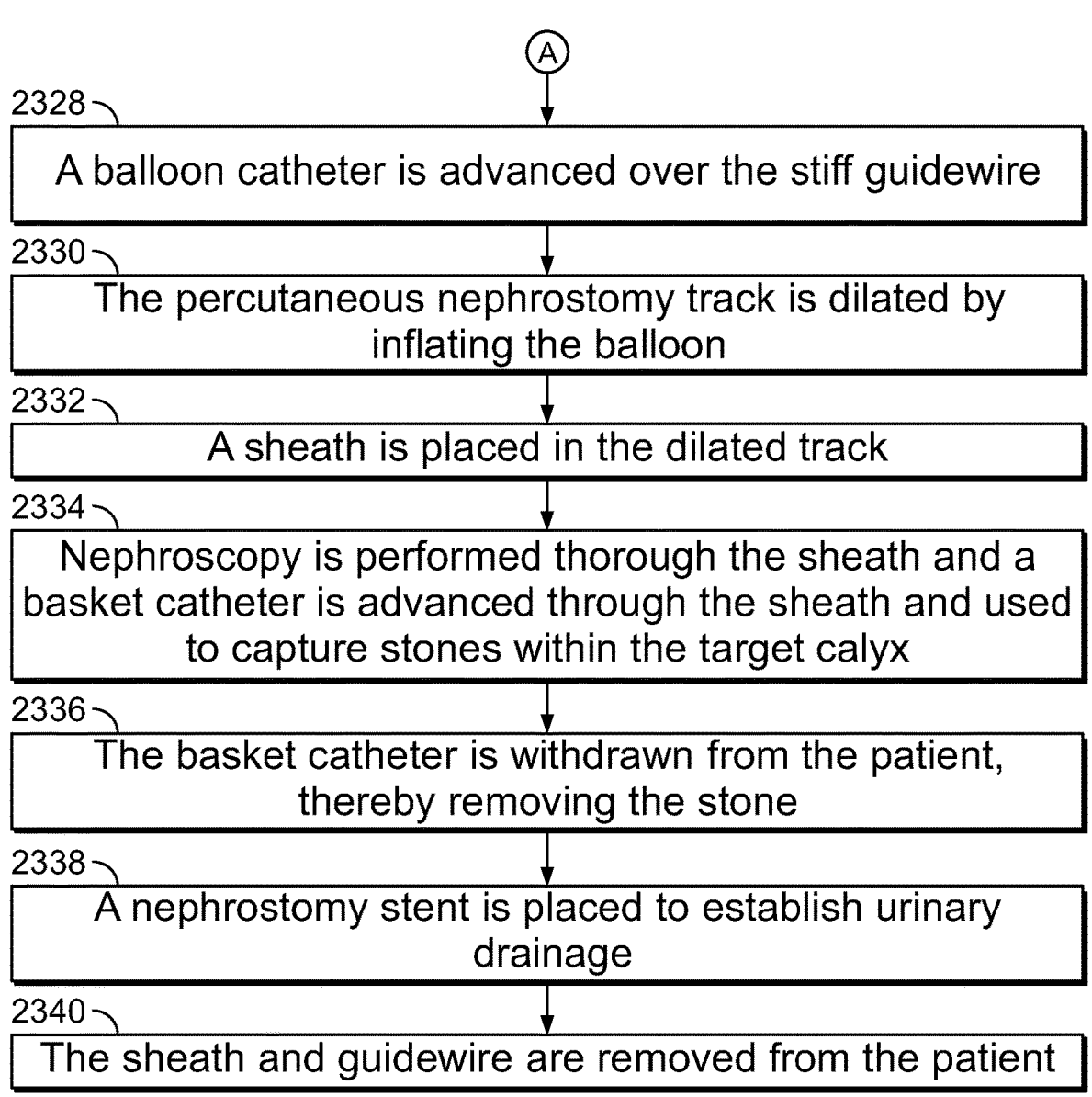

FIG. 23 is a flowchart illustrating an exemplary method of performing a reduced radiation percutaneous needle access procedure on a patient by using the reduced radiation kit, in accordance with an embodiment of the present specification. In an embodiment, a reduced radiation percutaneous needle access procedure is a percutaneous nephrolithotomy (PCNL) procedure involving placement of a needle through the patient's skin into the kidney for access into one of the calices of the kidney for removing kidney stones.

At step 2302 a surgeon places a sticker on the patient either directly on the skin of the patient prior to placing drapes over the patient, or after the drapes has been placed by palpating physiologic landmarks on the patient's body. Additional stickers may be placed on the patient's skin to identify the location of other internal organs. At step 2304, a guidewire is advanced retrograde into the renal pelvis of the patient. At step 2306, an occlusion balloon is advanced over the guidewire to a desired location in the patient's body (e.g., within the ureter near the renal pelvis). At step 2308, the guidewire is withdrawn and the occlusion balloon is inflated. At step 2310, a contrast agent is introduced through retrograde injection into a collecting system to visualize posterior calyces of the patient's kidney. In an embodiment, the contrast agent is an ultrasound contrast agent and the calyces are visualized using ultrasound technique. At step 2312, a laser guide on the imaging device or a C-arm is aligned with the target site within the patient's kidney. At step 2314, a reduced radiation needle access device is advanced through the patient's skin and into the target calyx. In an embodiment, the sticker comprises a recess or opening to accommodate passage of the needle. Additionally or alternatively, the sticker comprises a radiopaque circle having a hollow center that the surgeon can target the needle through.

In an embodiment, at step 2316 a needle is sheathed by a cannula that passes through the patient's skin with the needle. The laser guide is used to maintain alignment of the needle as the needle is advanced into the target calyx. At step 2318 the needle is removed from the cannula upon the needle and cannula reaching the target calyx, thereby establishing an access pathway to the target calyx through the cannula. At step 2320, a guidewire is passed through the cannula and into the target calyx. At step 2322, a basket catheter is used to snare the guidewire ureteroscopically. At step 2324, the guidewire is captured ureteroscopically and drawn through the ureter. At step 2326, after successful access is established, the guidewire is exchanged for another guidewire having a greater stiffness and having a safety guidewire placed alongside the stiff guidewire. In an embodiment, the needle is inserted into the calyx and then advanced past a stone in the patient's kidney into the ureter using fluoroscopy or ultrasound guidance.

At step 2328, a balloon catheter is advanced over the stiff guidewire. At step 2330 the percutaneous nephrostomy track is dilated by inflating the balloon. At step 2332 a sheath is placed in the dilated track. At step 2334, nephroscopy is performed thorough the sheath and a basket catheter is advanced through the sheath and used to capture stones within the target calyx. At step 2336, the basket catheter is withdrawn from the patient, thereby removing the stone. At step 2338, a nephrostomy stent is placed to establish urinary drainage. At step 2338, the sheath and guidewire are removed from the patient.

Figure 24:
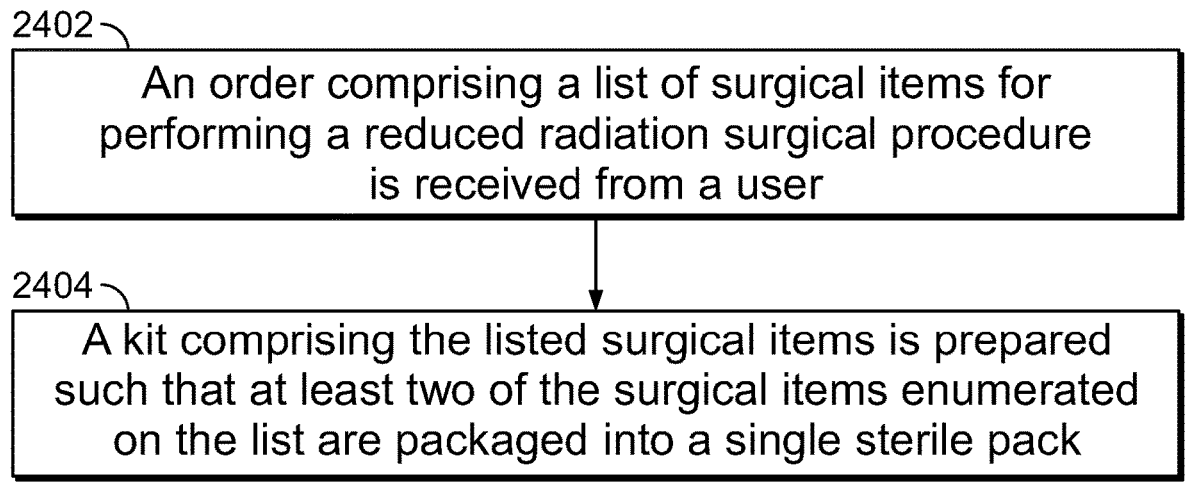
FIG. 24 is a flowchart illustrating a method of making a reduced radiation kit for performing a reduced radiation percutaneous procedure, in accordance with an embodiment of the present specification.

FIG. 24 is a flowchart illustrating a method of making a reduced radiation kit for performing a reduced radiation percutaneous procedure, in accordance with an embodiment of the present specification. At step 2402 an order comprising a list of surgical items for performing a reduced radiation surgical procedure is received from a user. In an embodiment, the surgical items are selected from a group consisting of a guidewire, a needle, a sticker, a balloon catheter, a stent, a sheath, a contrast agent, and a basket catheter. At step 2404 a kit comprising the listed surgical items is prepared such that at least two of the surgical items enumerated on the list are packaged into a single sterile pack. The surgical items are "reduced radiation surgical items" because the surgical items are adapted for use in a reduced radiation application.

During surgical procedures, aspiration or withdrawal of fluids is used to drain an area of a body that is being operated upon to keep it clear of excess blood and other fluids, thus facilitating visualization of the surgical field. According to aspects of the present specification, an aspiration port is used to confirm the correct location or position of a needle within a structure, for example aspiration of urine confirms a correct position of the needle within the renal collecting system, while aspiration of bile may confirm correct placement of the needle within the gallbladder. In accordance with various embodiments, the present specification describes a needle assembly comprising a system to withdraw excess fluid from a body during a surgical process. In an embodiment, a needle assembly is disclosed which comprises an aspiration port coupled to a proximal portion of a needle through which the excess fluids can be drained. In another embodiment the needle functions as a sheath to direct a needle for biopsy. In embodiments, the present specification is directed towards a needle that allows for facile orientation and direction of a trajectory when used in conjunction with reduced fluoroscopy settings.

Figure 25A:
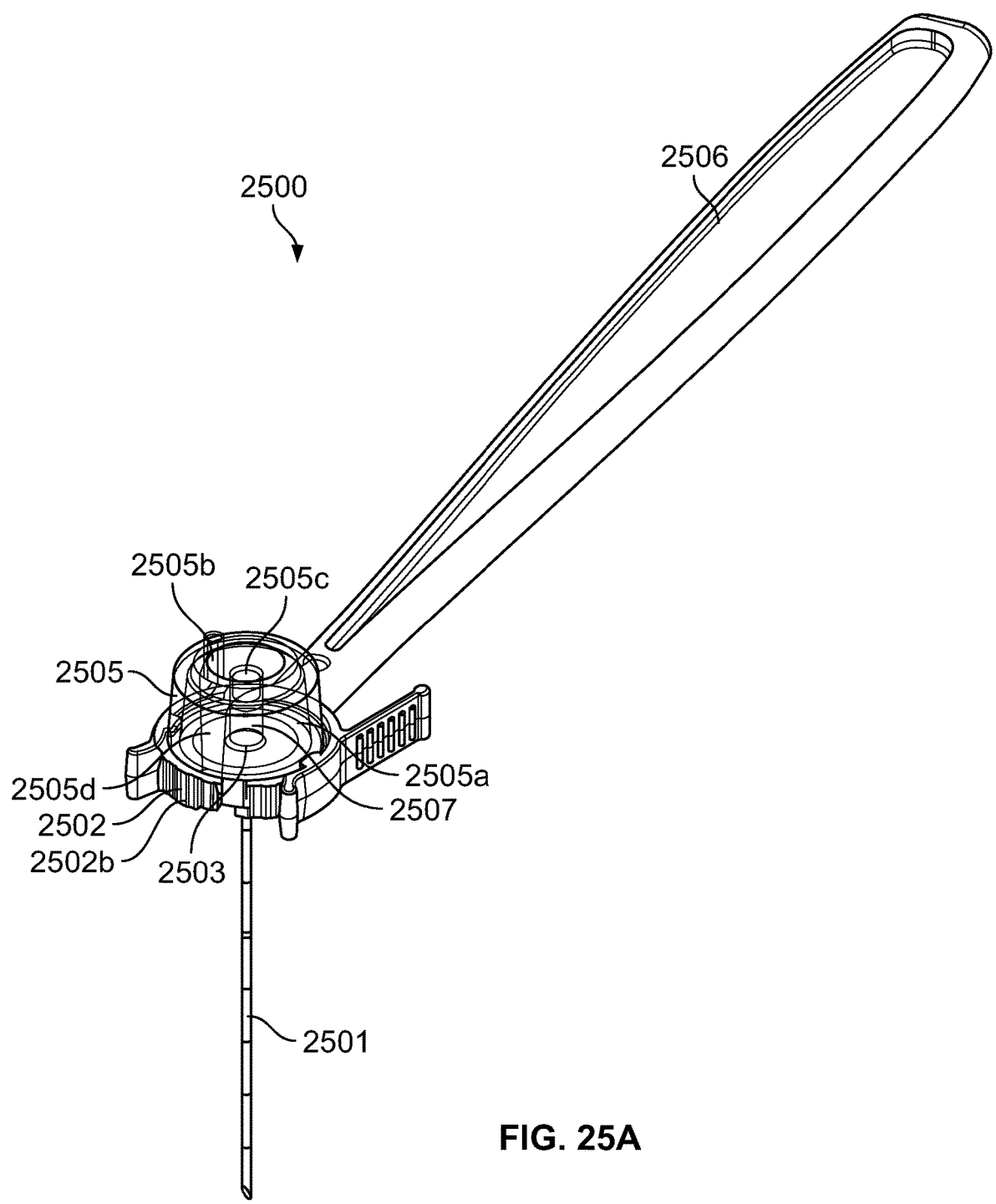
FIG. 25A illustrates an embodiment of a needle assembly, in accordance with some embodiments of the present specification.

FIG. 25A illustrates an embodiment of a needle assembly 2500 in accordance with an embodiment of the present specification. In the embodiment shown in FIG. 25A, needle assembly 2500 comprises a needle 2501, which is coupled to a needle hub 2502. In an embodiment, the needle hub 2502 is shaped to enable atraumatic introduction of the needle 2501. In an embodiment, the hub 2502 is disc-shaped although in alternate embodiments the hub 2502 may have other suitable shapes such as, but not limited to, cubic or pyramidal. The needle hub 2502 is coupled to an aspiration port 2503 that protrudes from the disc shaped hub 2502 and facilitates the withdrawal of any fluids from any area of the body into which the needle 2501 is placed. In embodiments, the fluids are drained through a syringe which is introduced through the aspiration port 2503. In another embodiment, the aspiration port 2503 is coupled with an inlet of a surgical drain/tube and the fluids are withdrawn through the surgical drain. In an embodiment, the fluids are withdrawn by creating a negative pressure at an outlet of the surgical drain. In an embodiment, the aspiration port 2503 is cylindrical in shape and comprises a threaded portion on its outer surface 2507, which facilitates connection between the aspiration port 2503 and a surgical drain/tube for draining out the fluids. In one embodiment, the internal portion of the cylindrical aspiration port 2503 has a smooth surface that allows for attachment of the aspiration port 2503 with a smooth tip syringe, a slip tip syringe, or a tubing system for aspiration. In embodiments, the aspiration port 2503 is coupled to an aspiration tube or lumen, which is placed inside the needle 2501. When fluids are drained from the body, the fluids pass through the aspiration tube or lumen and are then drained out from the aspiration port 2503.

Figure 25B:
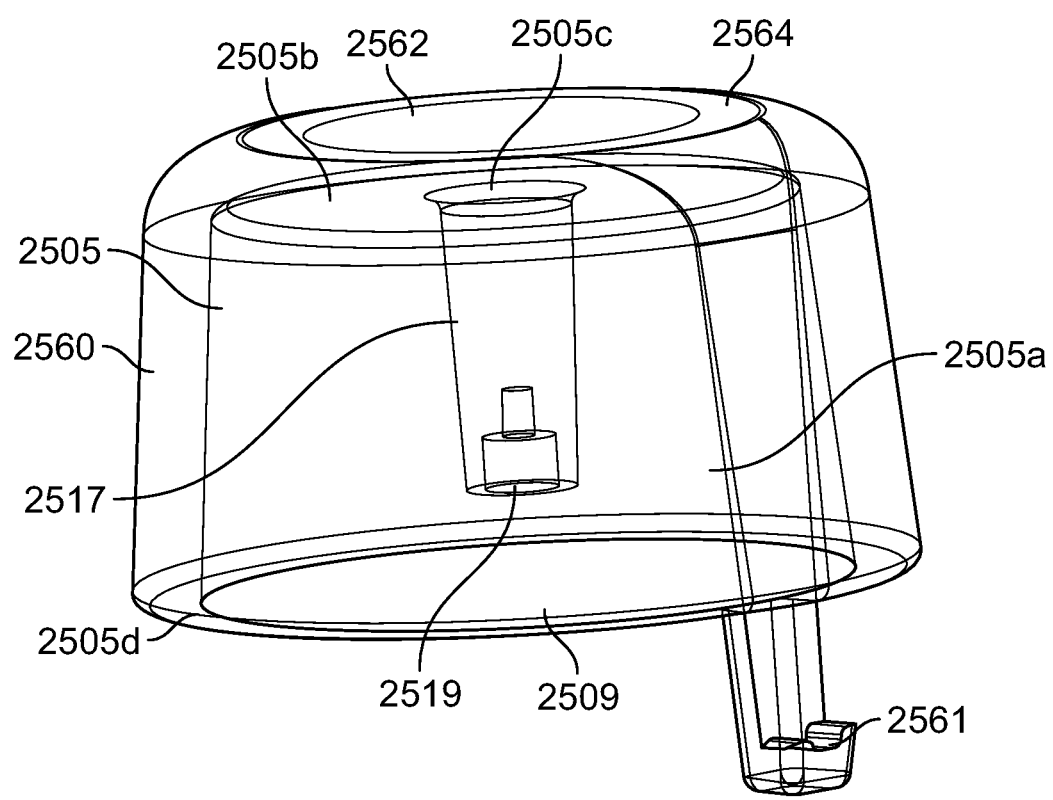
FIG. 25B illustrates an isometric view of a hub housing, in accordance with some embodiments of the present specification.

FIG. 25B illustrates an isometric view of a hub housing 2505, in accordance with some embodiments of the present specification. Referring simultaneously to FIG. 25A and FIG. 25B, in an embodiment, the needle assembly 2500 comprises a hub housing 2505 coupled to the needle hub 2502 wherein the hub housing 2505 is positioned over a portion 2502b of the needle hub 2502. In embodiments, a main body 2505a of the hub housing 2505 is translucent or transparent and glows when light enters the main body 2505a. A cap or top portion 2505b of the hub housing 2505 may be transparent, translucent, or opaque. A light ray, when aligned with an opening or channel 2505c positioned at the center of the cap or top portion 2505b, lights up the entire main body 2505a. The opening or channel 2505c allows for the passage of light from the light source through the cap or top portion 2505b. The dimensions of various portions are such that a maximum angle by which the needle 2501 deviates from the axis of the light source and still produces the illumination of the glowing main body 2505a of the needle 2501 is a very small angle. In an embodiment, the maximum angle of deviation ranges between 0.1 and 10 degrees. In an embodiment, the maximum angle of deviation is 2 degrees. In an embodiment, the maximum angle of deviation is less than 1 degree.

In an embodiment, a base 2505d of the hub housing 2505 comprises a cavity at its center, to receive the aspiration port 2503. In embodiments, the aspiration port 2503 is cylindrical in shape and comprises the threaded portion on its outer surface 2507 and correspondingly the cavity configured in the base 2505d of the illumination hub 2505 is also cylindrical and comprises a threaded surface to receive the aspiration port 2503. This cylindrical cavity in one embodiment is used to attach the hub housing 2505 to the needle hub 2502 during needle insertion. In an embodiment, cap or top portion 2505b includes an elongate member 2517 extending therefrom and into the cavity 2509. The elongate member is configured to rest within the aspiration port 2503 when the hub housing 2505 and needle hub 2502 are coupled. In an embodiment, the elongate member 2517 includes an opening 2519 for passage of a needle. In another embodiment, the hub housing 2505 just has a cylindrical space within it to allow a space for the cylindrical aspiration port 2503 to be positioned but the hub housing 2505 is not attached to the needle hub 2502. Once proper alignment is achieved, the hub housing 2505 is removed and the aspiration port 2503 is revealed.

Referring to FIG. 25B, in embodiments, a hub cover 2560 is removably attached to the hub housing 2505 in order to cover the hub housing 2505. In some embodiments, hub housing 2505 includes latching member 2561 to attach the housing to needle hub 2502. Hub cover 2560 is shaped similar to the hub housing 2505, and is large enough to hold the hub housing 2505 centrally within. A circular opening 2562 through a central top portion of the hub cover 2560 may be provided to allow light rays to travel through towards the opening 2505c of the hub housing 2505. The opening 2562 may be encircled by an opaque ring 2564 to aid the surgeon to accurately position or target a light guide source (e.g. laser). The ring 2564 is opaque which prevents the light from entering into the main body 2505a unless the light ray is aligned with the opening 2505c positioned on the top surface 2505b. The opening 2505c allows for the passage of light from the light source through the top portion 2505b. In embodiments, the top portion 2505b of the hub housing 2505 is circular in shape and the distance between the central axis/opening 2505c and any point on the boundary of the top portion (that is, the radius of the top portion 2505b) ranges between 0.5 mm and 5.0 mm, or between 1.0 mm and 2.0 mm. In some embodiments, the radius of the top portion 2505b is one of 2 mm, and 1.5 mm.

In an embodiment, the hub housing 2505 is also coupled with an extension arm 2506 (similar to an extension arm 2706a or arm 2706b shown and described with respect to FIGS. 27A and 27B below) which allows a surgeon to hold and direct the needle assembly 2500 from a distance without placing the surgeon's hands within the direct collimated beam of fluoroscopic radiation emanating from a C-arm, CT scanner, or other radiation source. In one embodiment, the extension arm 2506 is a single arm. In another embodiment, the extension arm 2506 comprises two stabilization arms. In yet another embodiment, the extension arm 2506 comprises a plurality of stabilization arms ranging from 1-10. In one embodiment the extension arm 2506 has, at the proximal end, a male screw which will mate with a female screw attachment on the side of the hub housing 2505. In another embodiment, the extension arm 2506 has, at the proximal end, a male screw, which will mate with a female screw attachment on the side of the needle hub portion 2502b so that the surgeon can hold the needle using the extension arm even when the hub housing 2505 has been removed to allow for aspiration of fluids. In another embodiment the extension arm 2506 attaches to the needle via a snapping mechanism. In another embodiment the extension arm 2506 is preformed and already attached to the needle.

Figure 26B:
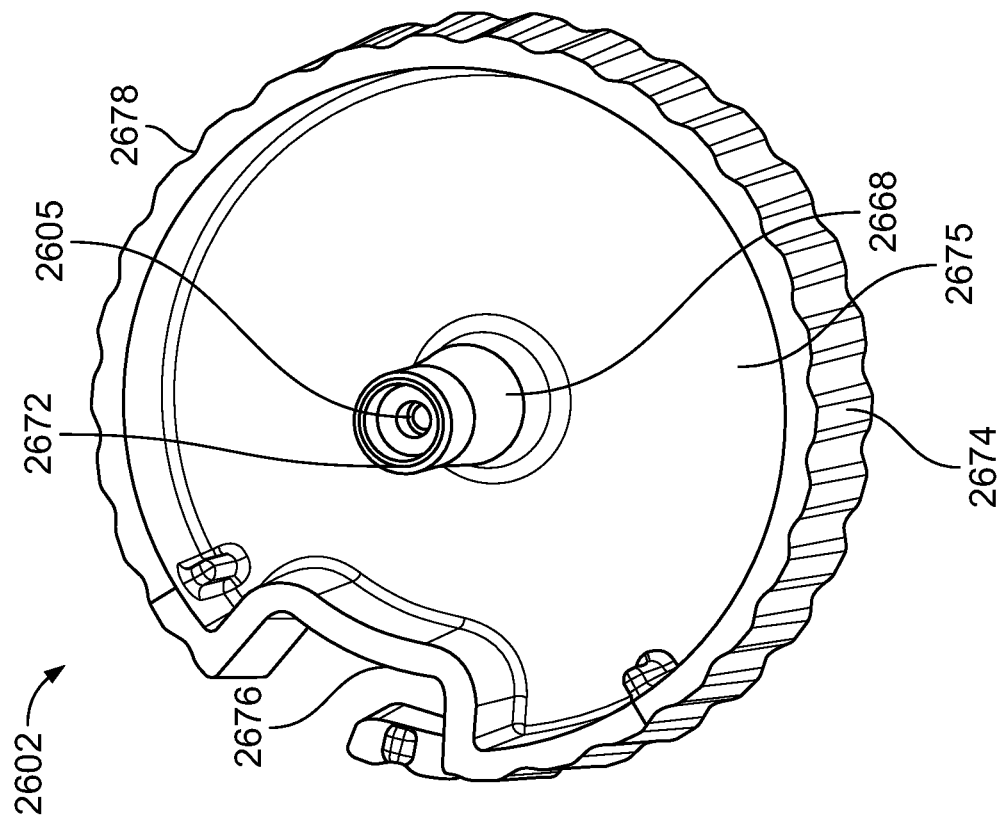
FIG. 26B illustrates a bottom perspective view of the needle hub shown in FIG. 26A.
Figure 26A:
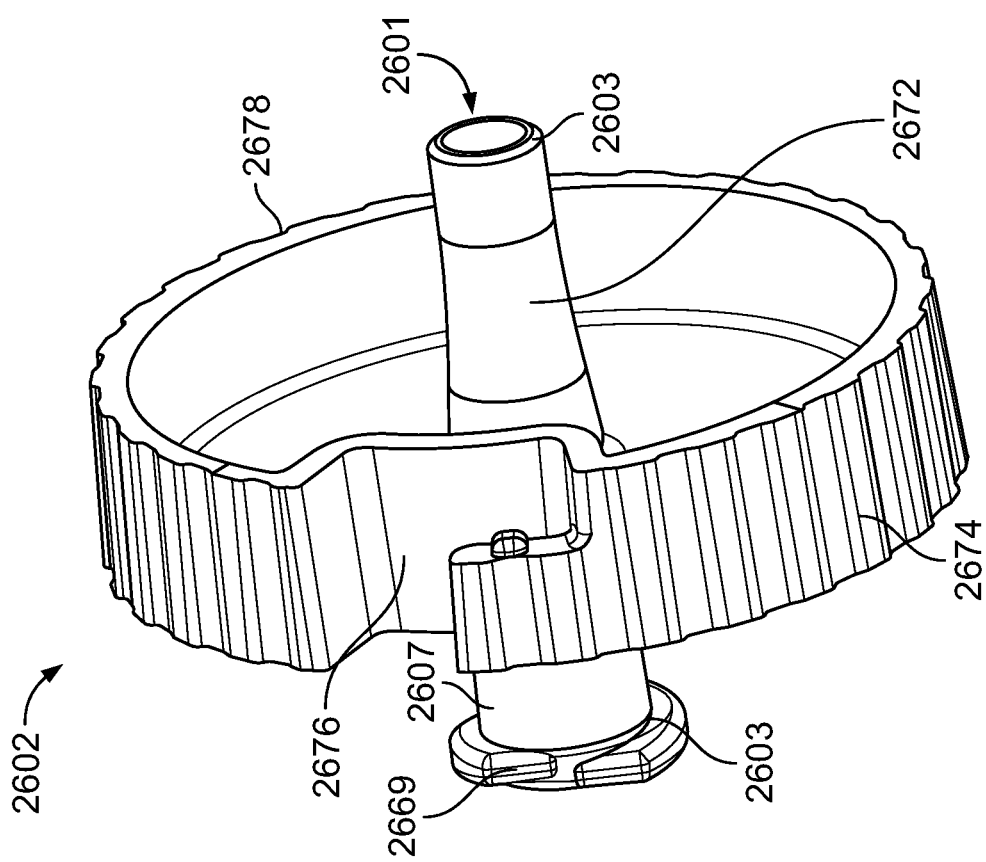
FIG. 26A illustrates a side perspective view of a disc-shaped needle hub similar to the hub shown in FIG. 25A.

FIG. 26A illustrates a side perspective view of a disc-shaped needle hub 2602 similar to the hub shown in FIG. 25A. FIG. 26B illustrates a bottom perspective view of the needle hub 2602 shown in FIG. 26A. FIG. 26C illustrates a top perspective view of the needle hub 2602 shown in FIG. 26A. Referring simultaneously to FIGS. 26A, 26B, and 26C, the needle hub 2602 is defined by a planar structure shaped to enable atraumatic introduction of a needle through a needle port 2672. A first channel 2601 extends through the planar structure of the needle hub 2602. The needle port 2672 is provided in a form of a protruding hollow cylindrical or conical configuration or shape attached to a first bottom surface or side 2675 of the hub 2602. In an embodiment, the needle port 2672 comprises a first exterior housing or outer surface 2668. The needle port 2672 includes a first lumen 2605 in fluid communication with the first channel 2601. In an embodiment, the hub 2602 is disc-shaped although in alternate embodiments the hub 2602 may have other suitable shapes such as, but not limited to, cubic or pyramidal. A circumference 2674 of the hub 2602 may be corrugated to enable a handle, such as extension arm 2506 shown in FIG. 25A, to grip the hub 2602. In some embodiments, a recess 2676 is configured within a portion of the circumference 2674 of the needle hub 2602. In an embodiment, the recess 2676 enables hub housing 2505, shown in FIG. 25B, to removably attach to the needle hub 2602 via latching member 2561, wherein recess 2676 in configured to receive the latching member 2561. FIG. 26D illustrates a side view of a needle hub 2602 engaged with a hub housing 2505. The latching member 2561 of the hub housing 2505 is received within the recess 2676 of the needle hub 2602, removably attaching the hub housing 2505 to the needle hub 2602 in a locked position. The aspiration port 2603 extends into the hub housing 2505 and the needle port 2672 extends in an opposite direction. An obturator 2613 of a needle access system is disposed within the needle port 2672. Referring again to FIGS. 26A-26C, in some embodiments, edge 2678 is marked with a color and a second top surface or side 2673 includes a ring 2671, which in combination with ring 2564 (shown in FIG. 25B) may aid the surgeon to accurately position or target a light guide source.

On second top surface or side 2673 opposite the side of the needle port 2672, the needle hub 2602 is coupled to an aspiration port 2603 that protrudes from the disc shaped hub 2602 and facilitates the withdrawal of any fluids from any area of the body into which the needle is placed. In embodiments, after a needle has been passed through the needle hub 2602 and proper alignment has been achieved using a laser light, the needle is passed into a target tissue in a patient. The hub housing 2505 is then removed to reveal the aspiration port 2603. In embodiments, the fluids are drained through a syringe which is introduced through the aspiration port 2603. In another embodiment, the aspiration port 2603 is coupled with an inlet of a surgical drain/tube and the fluids are withdrawn through the surgical drain. In an embodiment, the fluids are withdrawn by creating a negative pressure at an outlet of the surgical drain. In an embodiment, the aspiration port 2603 is cylindrical in shape and comprises a threaded portion or luer lock 2669 on a second exterior housing or outer surface 2607, which facilitates connection between the aspiration port 2603 and a surgical drain/tube for draining out the fluids. The aspiration port includes a second lumen 2609 in fluid communication with the first channel 2601. In one embodiment, the internal portion of the cylindrical aspiration port 2603 has a smooth surface that allows for attachment of the aspiration port 2603 with a smooth tip syringe, a slip tip syringe, or a tubing system for aspiration. In embodiments, the aspiration port 2603 is coupled to an aspiration tube or lumen, which is placed inside the needle. When fluids are drained from the body, the fluids pass through the aspiration tube or lumen and are then drained out from the aspiration port 2603.

Figure 27B:
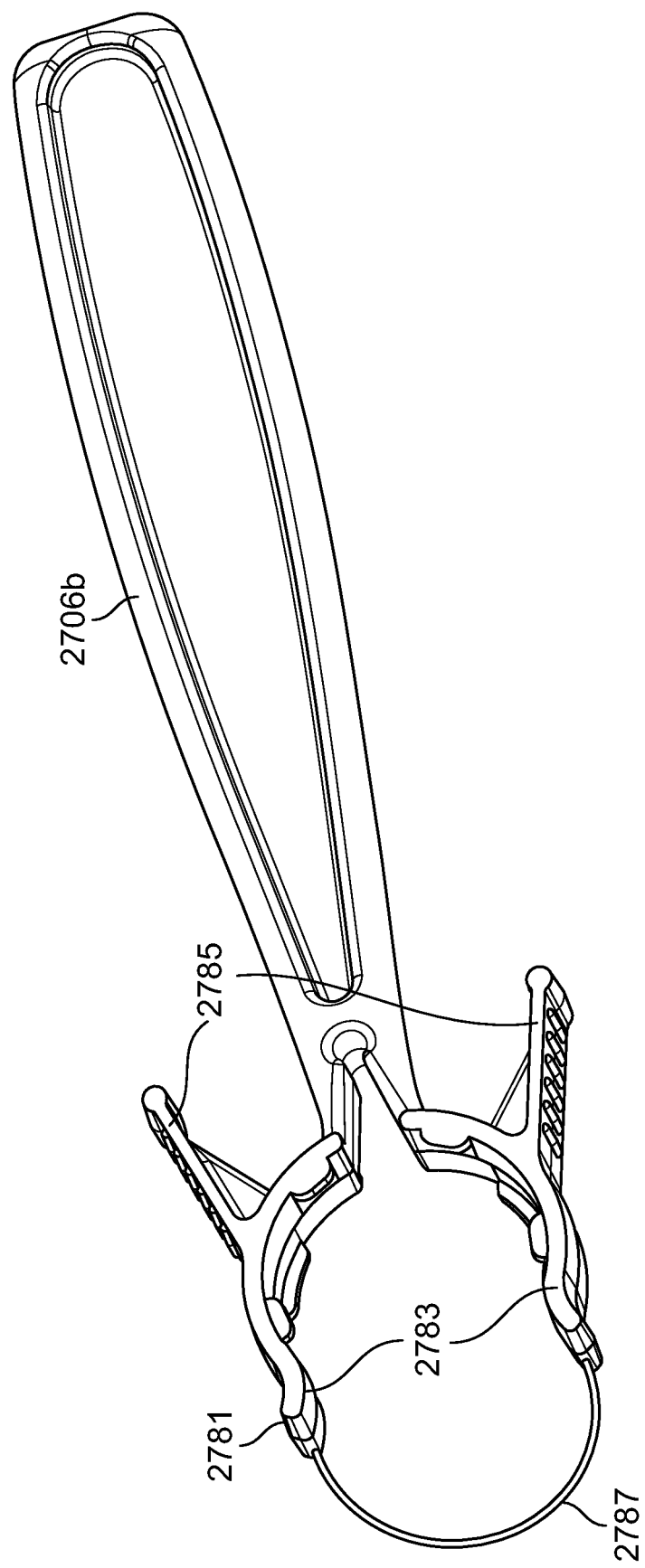
FIG. 27B illustrates an extension arm for handling a needle assembly in accordance with another embodiment of the present specification.

FIG. 27A illustrates an extension arm 2706a for handling a needle assembly in accordance with an embodiment of the present specification. FIG. 27B illustrates an extension arm 2706b for handling a needle assembly in accordance with another embodiment of the present specification. As shown in FIGS. 27A and 27B, extension arms 2706a and 2706b allow a surgeon to operate a needle assembly from a distance without placing their hands within the radiation beam. Arm 2706a has a length greater than the length of arm 2706b, which is relatively shorter and wider than arm 2706a. FIG. 25A illustrates an embodiment of an arm 2506, similar to arms 2706a and 2706b, attached to a needle hub. Usually, surgeons are required to grasp a needle using their hands leading to direct fluoroscopic radiation exposure. As fluoroscopy exposure is also known to be very harmful and have a cumulative effect over time, it is important to decrease the radiation exposure of medical personnel during percutaneous access or needle insertion. Surgeons can therefore reduce their fluoroscopy exposure by grasping the arm 2706a or 2706b and controlling the position and placement of the needle hub. In some embodiments, the arms 2706a or 2706b are attached to a pliers-like configuration 2780, 2781 at one end, which comprises a pair of levers joined to the arm 2706a or 2706b at one end. The levers include a pair of jaws 2782, 2783 that are curved to enable them to provide a firm grip around a disc-shaped needle hub, and a pair of handles 2784, 2785. Handles 2784, 2785 may be pinched or compressed towards each other to open the jaws 2782, 2783 while positioning the needle hub within the jaws 2782, 2783. Once positioned, the handles 2784, 2785 may be released as the jaws 2782, 2783 compress and firmly grip the circumference of the needle hub. In some embodiments, extension arms 2706a and 2706b further include locking bands 2786, 2787 which are configured to lock the jaws 2782, 2783 together around a needle hub to keep the needle hub firmly in place.

Operating the needle assembly through the extension arms 2706a and 2706b reduces the exposure to fluoroscopic radiation and enhances the safety of the person conducting the procedure. In an embodiment, the extension arm 2706a or 2706b is coupled to the illumination hub instead of the needle hub. In another embodiment, the extension arm 2706a or 2706b is coupled to a needle in the needle assembly instead of the illumination hub or the needle hub. In an embodiment, the extension arm 2706a or 2706b snap fits around any portion such as illumination hub, needle hub or the needle. In another embodiment, an extension arm is magnetically coupled to a portion of the needle assembly. In another embodiment, an extension arm comprises a threaded surface on one of its ends, which is received into a corresponding cavity provided in a portion of the needle assembly. One of ordinary skill in the art would appreciate that the extension arm can be coupled to the needle assembly in multiple other ways without departing from the core spirit and scope of the present specification. In an embodiment, the extension arm is cylindrical in shape. In embodiments, a diameter of the extension arm ranges from 3 to 7 mm. In an embodiment the diameter of the extension arm is 5 mm. In an embodiment, a length of the cylindrical extension arm ranges between 5 cm and 15 cm. In one embodiment, the extension arm is constructed of extremely lightweight but strong materials to prevent the needle from bending during targeting. In another embodiment the arm could be made of lightweight plastic, polymers, lightweight metal (titanium or other alloy).

Figure 27C:
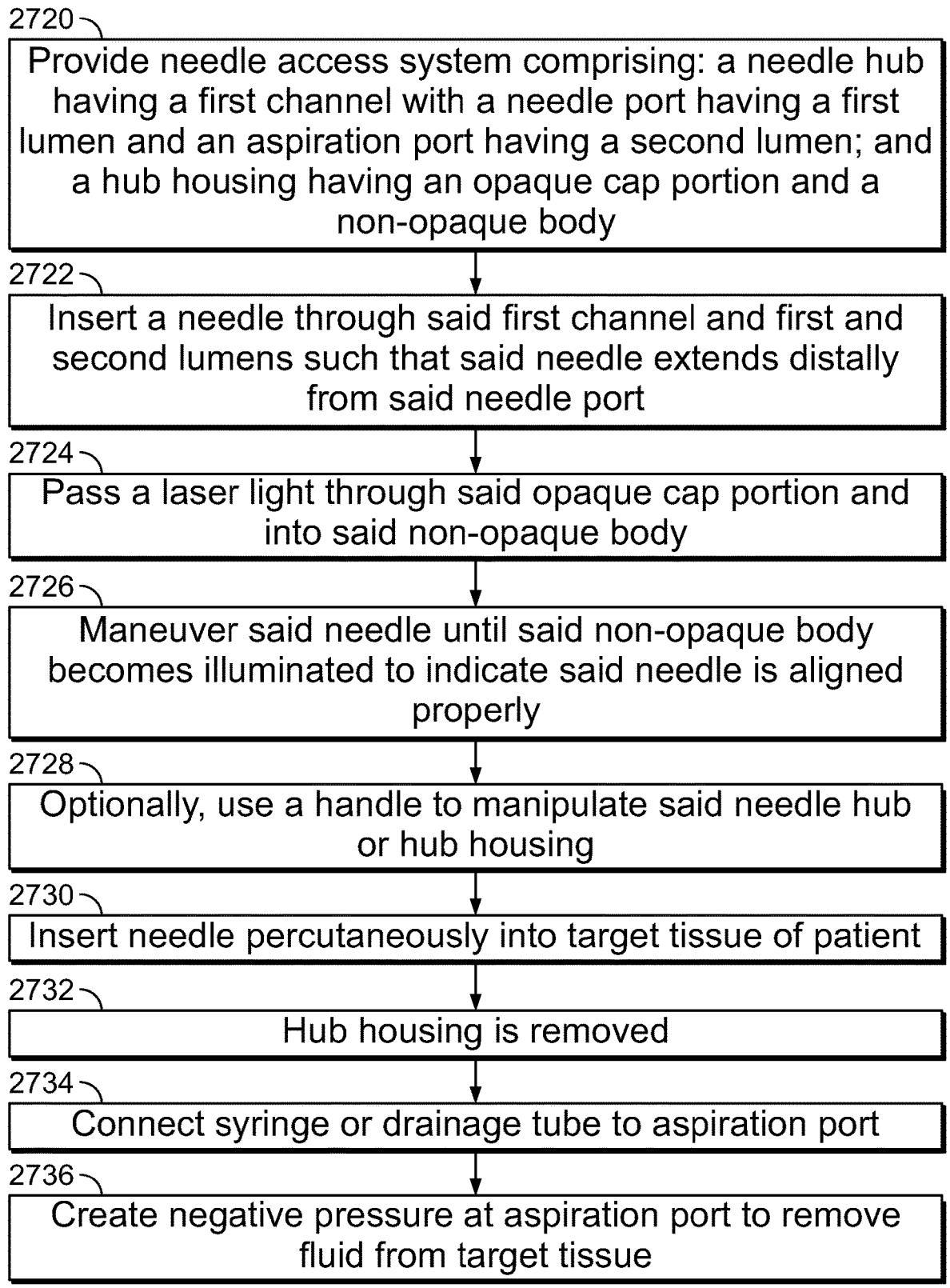
FIG. 27C is a flowchart illustrating a method of using a needle access system in accordance with an embodiment of the present specification.

FIG. 27C is a flowchart illustrating a method of using a needle access system in accordance with an embodiment of the present specification. At step 2720, a needle access system comprising: a needle hub having a first channel with a needle port having a first lumen and an aspiration port having a second lumen; and a hub housing having an opaque cap portion and a non-opaque body, is provided. A needle is inserted through said first channel and said first and second lumens such that said needle extends distally from said needle port at step 2722. At step 2724, a laser light is passed through said opaque cap portion and into said non-opaque body. The needle is maneuvered at step 2726 until the non-opaque body becomes illuminated, indicating that the needle is properly aligned. Optionally, at step 2728, a handle, such as the extension arms described with reference to FIGS. 27A and 27B, is used to manipulate the needle hub or hub housing. The needle is inserted into a target tissue of a patient at step 2730. The hub housing is removed at step 2732 to reveal the aspiration port. At step 2734, a syringe or drainage tube is connected to the aspiration port. Then, at step 2736, negative pressure is created at the aspiration port to remove fluid from the target tissue.

In an embodiment, the present specification describes a system and method that involves visualizing an accurate position of a needle inside the body with the assistance of reduced levels of fluoroscopic radiation. In an embodiment, radiopaque markers such as metal rings are coupled to a needle assembly that enhance its visualization on a display screen during a procedure when using extremely low levels of radiation exposure and therefore helps in ascertaining an exact location of a needle inside a body.

FIG. 28A illustrates a needle assembly comprising radiopaque markers for needle alignment in accordance with an embodiment of the present specification. As shown in FIG. 28A, needle assembly 2800 comprises a central lumen or cannula 2805 through which a needle is inserted. The central lumen 2805 is coupled to a main body or hub 2802. The main body or hub 2802 comprises two radiopaque markers structured in the form of radiodense rings 2803 and 2804 that encircle a circumference of the hub 2802 at two different positions respectively. In alternative embodiments, radiodense rings 2803 are replaced by squares, rectangles, or any other shape that is radio-opaque and easy to see under low dose fluoroscopy. Additionally, in some embodiments, a single ring or any other shape is used as a radiopaque marker. These one or more radiodense rings could be made of metal or any other radiodense material. During fluoroscopic radiation, the two metal rings 2803, 2804 and the central lumen 2805 can be seen by a surgeon on a display screen which helps in understanding a precise location of the central lumen 2805 and ensuring that it is properly aligned with respect to the needle assembly. In another embodiment there could be only one ring. The radius of the ring is variable and could be small to help facilitate precise positioning ranging from 1-5 mm. In another embodiment the ring could be 2 cm in diameter. In another embodiment the diameter of the ring could be between 5 mm and 10 cm. In the configuration with two rings the rings could vary in diameter by 10-300%. In another configuration there could be a plurality of rings ranging between 2-10 in number. In one embodiment the two rings are both on the surface at location 2804. In another embodiment the two or plurality of rings could be at different levels on the hub 2802 with one ring at position 2804 while a second ring was located at position 2803 such that the rings could be easily aligned even if the needle tip was difficult to see due to the low levels of radiation being employed.

FIG. 28B illustrates a central lumen and metal rings of a needle assembly observed under fluoroscopic radiation when the needle assembly is properly aligned in accordance with an embodiment of the present specification. As shown in FIG. 28B, when the needle assembly is properly aligned, the metal rings 2803 and 2804 are visible as two concentric circles and the central lumen 2805 is visible as a dot on the display screen immediately in the center of the ring.

FIG. 28C illustrates a central lumen and metal rings of a needle assembly observed under fluoroscopic radiation when the needle assembly is not properly aligned in accordance with an embodiment of the present specification. As shown in FIG. 28C, when the needle assembly is not properly aligned, the metal rings 2803 and 2804 are visible as two non-concentric circles on the display screen and the central lumen 2805 represented as a dot is also displaced. If the needle assembly is misaligned as shown in FIG. 28C, the surgeon can move the needle assembly to align the same until the position of metal rings and central lumen are displayed as concentric circles as shown in FIG. 28B. Upon perfect alignment, the central lumen appears as the exact geometric center of the two concentric circles.

In an embodiment, the circumference of the metal ring 2804 is larger than the circumference of the metal ring 2803. In embodiments, the metal ring 2803 and metal ring 2804 need to have an appropriate thickness because in case the thickness of rings is too thin, they may not be detected under very low dose fluoroscopic radiation settings and in case the rings are too thick, they might obscure vision of other elements. In one embodiment the rings are 2 mm thick. In another embodiment the rings are 1 mm thick. In another embodiment the rings are between 0.1 and 3 mm thick. In one embodiment both rings are of the same thickness. In another embodiment the inner ring is less thick than the outer ring by 50%. In another embodiment the inner ring is between 1 and 99% thinner than the outer ring.

In an embodiment, the main body 2802 comprises a needle hub (such as 2502 shown in FIG. 25B and does not comprise any illumination hub (such as hub housing 2505 shown in FIG. 25B). The needle hub comprises a plurality of metal rings encircling its circumference that assist in alignment of needle through fluoroscopic radiation as described above. In an embodiment, the needle hub comprising a plurality of metal rings is fixed with the needle and is a part of a full needle assembly. In another embodiment, the needle hub comprising a plurality of metal rings is a detachable component which can be detached from the needle. In embodiments, the needle and the needle hub comprising the metal ring are commercially sold as separate independent components.

In an alternative embodiment, the main body 2802 comprises a needle hub (such as 2502 shown in FIG. 25B and also comprises an illumination hub (such as hub housing 2505 shown in FIG. 25B). However, in this embodiment, the illumination hub does not comprise any of the internal components (e.g. foam, lens, shaft, and mask) and hence cannot be used for alignment through laser guidance. In this embodiment, the illumination hub comprises a plurality of metal rings encircling its outer circumference that assist in alignment of needle through fluoroscopic radiation as described in above embodiments. The above described needle solution is a very cost competitive solution as it comprises a hollow hub without laser features (e.g. obturator, adaptor, mask) which means that the overall cost of manufacturing this needle assembly is relatively lower as compared to a laser assembly having a functional illumination hub. Further, this device requires little or no regulatory clearance time as it will fall under Class I device classification as per the US FDA norms.

The above examples are merely illustrative of the many applications of the system of present specification. Although only a few embodiments of the present specification have been described herein, it should be understood that the present specification might be embodied in many other specific forms without departing from the spirit or scope of the specification. Therefore, the present examples and embodiments are to be considered as illustrative and not restrictive, and the specification may be modified within the scope of the appended claims.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments, whether these features, elements, and/or steps are included or are to be performed in any particular embodiment.

The terms "approximately," "about," and "substantially" as used herein represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

Although certain embodiments and examples have been described herein, it will be understood by those skilled in the art that many aspects of the methods and devices shown and described in the present disclosure may be differently combined and/or modified to form still further embodiments or acceptable examples. All such modifications and variations are intended to be included herein within the scope of this disclosure. A wide variety of designs and approaches are possible. No feature, structure, or step disclosed herein is essential or indispensable.

Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Moreover, while illustrative embodiments have been described herein, the scope of any and all embodiments having equivalent elements, modifications, omissions, combinations (e.g., of aspects across various embodiments), adaptations and/or alterations as would be appreciated by those in the art based on the present disclosure. The limitations in the claims are to be interpreted broadly based on the language employed in the claims and not limited to the examples described in the present specification or during the prosecution of the application, which examples are to be construed as non-exclusive. Further, the actions of the disclosed processes and methods may be modified in any manner, including by reordering actions and/or inserting additional actions and/or deleting actions. It is intended, therefore, that the specification and examples be considered as illustrative only, with a true scope and spirit being indicated by the claims and their full scope of equivalents.

Any methods disclosed herein need not be performed in the order recited. The methods disclosed herein include certain actions taken by a practitioner; however, they can also include any third-party instruction of those actions, either expressly or by implication. For example, actions such as "aligning a needle with a light source" include "instructing alignment of a needle and a light source."

The ranges disclosed herein also encompass any and all overlap, sub-ranges, and combinations thereof. Language such as "up to," "at least," "greater than," "less than," "between" and the like includes the number recited. Numbers preceded by a term such as "about" or "approximately" include the recited numbers. For example, "about 3 mm" includes "3 mm."

We claim:

1. A needle access system comprising:
    a needle hub defined by a disc-shaped structure having a first channel therein and two opposing sides, wherein the needle hub further comprises a needle port attached to a first of the two opposing sides and having a first exterior housing and a first lumen positioned within the first exterior housing in fluid communication with the first channel and a first radiopaque ring defined by a first diameter attached to at least one of the two opposing sides; and
    a hub housing configured to be attached to the needle hub, wherein the hub housing comprises a cap portion, and a second radiopaque ring positioned on the cap portion, wherein the second radiopaque ring has a second diameter that is different than the first diameter.

2. The needle access system of claim 1, wherein the disc-shaped structure comprises a circumferential periphery and wherein a recess is positioned in the circumferential periphery.

3. The needle access system of claim 2, wherein said hub housing comprises a latching member configured to detachably mate with the recess.

4. The needle access system of claim 1, wherein said hub housing is non-opaque.

5. The needle access system of claim 1, wherein a circumferential periphery of the disc-shaped structure comprises a plurality of grooves.

6. The needle access system of claim 1, wherein the first diameter is smaller than the second diameter.

7. The needle access system of claim 1, wherein said needle port has a hollow cylindrical or conical shape and extends in a direction opposite said hub housing.

8. The needle access system of claim 1, wherein a base portion of the hub housing is configured to be removably engaged with the needle hub and configured to receive the port in a cavity defined by the cap portion.

9. The needle access system of claim 1, further comprising a port attached to a second of the two opposing sides and having a second exterior housing and a second lumen positioned within the second exterior housing in fluid communication with the first channel.

10. The needle access system of claim 1, wherein the needle hub further comprises a luer connector.

11. The needle access system of claim 1, wherein the cap portion is opaque and removably secured to a non-opaque body portion.

12. The needle access system of claim 11, wherein an inner diameter of the non-opaque body portion is larger than a diameter of the first channel.

13. A method of using a needle access system comprising:
    providing a needle access system comprising;
        a needle hub defined by a disc-shaped structure having a first channel therein and two opposing sides, wherein the needle hub further comprises a needle port attached to a first of the two opposing sides and having a first exterior housing and a first lumen positioned within the first exterior housing in fluid communication with the first channel and a first radiopaque ring defined by a first diameter attached to at least one of the two opposing sides; and
        a hub housing configured to be attached to the needle hub, wherein the hub housing comprises a cap portion and a second radiopaque ring positioned on the cap portion, wherein the second radiopaque ring has a second diameter that is different than the first diameter,
    inserting a needle through said first channel and first lumen such that said needle extends distally from said needle port;
    applying a beam of fluoroscopic radiation toward the needle access system; and
    maneuvering said needle until first radiopaque ring is centered within the second radiopaque ring.

14. The method of claim 13, wherein the disc-shaped structure comprises a circumferential periphery and wherein a recess is positioned in the circumferential periphery and wherein said hub housing comprises a latching member configured to detachably mate with the recess.

15. The method of claim 13, wherein said needle access system further includes a handle configured to be coupled to said needle hub or said hub housing and said method further includes using said handle to maneuver said needle hub or hub housing.

16. The method of claim 15, wherein said handle comprises an extension arm having a pair of jaws at one end for grasping said needle hub or said hub housing.

17. The method of claim 13, further comprising:
    inserting said needle percutaneously into a target tissue of a patient;
    removing said hub housing to reveal an aspiration port integrated into said needle hub; and
    connecting a syringe or drainage tube to said aspiration port.

18. The method of claim 17, further comprising creating negative pressure at said aspiration port to remove fluid from said target tissue.

* * * * *